United States Patent
Shi

(10) Patent No.: US 9,676,870 B2
(45) Date of Patent: Jun. 13, 2017

(54) METHODS OF TREATING ATHEROSCLEROSIS AND ANEURYSM

(75) Inventor: Guo-Ping Shi, Newton, MA (US)

(73) Assignee: The Brigham and Women's Hospital, Inc., Boston, MA (US)

(*) Notice: Subject to any disclaimer, the term of this patent is extended or adjusted under 35 U.S.C. 154(b) by 583 days.

(21) Appl. No.: 14/236,544

(22) PCT Filed: Aug. 6, 2012

(86) PCT No.: PCT/US2012/049746
§ 371 (c)(1),
(2), (4) Date: Jun. 10, 2014

(87) PCT Pub. No.: WO2013/020132
PCT Pub. Date: Feb. 7, 2013

(65) Prior Publication Data
US 2014/0322199 A1    Oct. 30, 2014

Related U.S. Application Data

(60) Provisional application No. 61/514,992, filed on Aug. 4, 2011.

(51) Int. Cl.
*A61K 39/395* (2006.01)
*C07K 16/42* (2006.01)
*A61K 39/00* (2006.01)

(52) U.S. Cl.
CPC .... *C07K 16/4291* (2013.01); *A61K 2039/505* (2013.01)

(58) Field of Classification Search
None
See application file for complete search history.

(56) References Cited

U.S. PATENT DOCUMENTS

| | | | | |
|---|---|---|---|---|
| 6,723,833 B1* | 4/2004 | Lowman | .......... | A61K 39/39566 435/69.6 |
| 8,618,095 B2* | 12/2013 | Yu | ........................ | C07D 498/04 514/230.5 |
| 2003/0229030 A1* | 12/2003 | Theoharides | ........ | A61K 31/353 514/27 |
| 2004/0086942 A1* | 5/2004 | Lowman | .................. | C07K 7/06 435/7.1 |
| 2008/0081788 A1* | 4/2008 | Lipps | ..................... | A61K 38/04 435/7.1 |
| 2010/0316649 A1* | 12/2010 | Zhang | .................. | C07D 487/04 424/145.1 |
| 2013/0243750 A1* | 9/2013 | Scheerens | ........ | A61K 39/39566 424/131.1 |

OTHER PUBLICATIONS

Takagi et al., J Exp Med. Jul. 1, 1989;170(1):233-44.*
Wang et al., J Clin Invest. Sep. 2011;121(9):3564-77. doi: 10.1172/JCI46028.*
Omalizumab: "Instructions, usage and formula", http://www.rlset.ru/mnn_index_id_3748.htm, pp. 1-6 (Oct. 23, 2012).
Stryuk et al., "Internal Diseases", Vnutrennie bolezni. M., GEOTAR-Media, pp. 66-67 (2008).
Mairon D. Dzh et al., Sovremennye perspektivy primeneniya statinov. Mezhdunarodnyi Meditsinskiy Zhurnal, 2000, . No. 6, [retrieved on Oct. 25, 2012] Retrieved from the Internet<URL:http://www.medi.ru>doc/7700605.htm>.
Inouye et al., "An Immune Response Network Associated with Blood Lipid Levels" PLoS Genetics 6(9):e1001l3 (2010).
Omalizumab: instruktsiya, primenenie i formula. Spravochnik lekarstv RLS,2009, [retrieved on Oct. 23, 2012] Retrieved from the Internet<URL:http://www.rlsnet.ru/ mnn_index_id_3748.htm>,pp. 1-6.
Stryuk et al., Vnutrennie bolezni. M., "GEOTAR-Media", p. 67 (2008).
Denner M. "Diabet i vospalenie". V mire nauki, 2010, No. 3, pp. 9-10, abstract, 6-12 [retrieved on Oct. 25, 2012] Retrieved from the Internet<URL:http://fesmu.ru>elibi Article.aspx?id=217615>.
Chang, "The pharmacological basis of anti-IgE therapy." Nature Biotechnology 18(2):157-162 (2000).
Rudolf et al., "Epitope-specific antibody response to IgE by mimotope immunization." The Journal of Immunology 160(7)3315-3321 (1998).

* cited by examiner

*Primary Examiner* — MIchael Szperka
(74) *Attorney, Agent, or Firm* — Nixon Peabody LLP

(57) ABSTRACT

The technology described herein is directed to methods of treating cardiovascular and metabolic disorders.

4 Claims, 24 Drawing Sheets

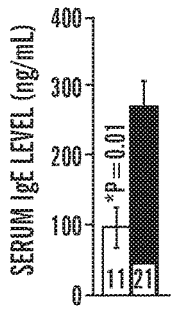 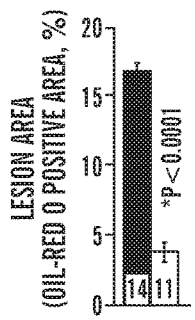 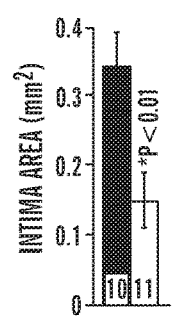 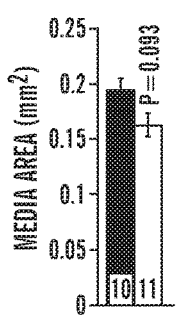
FIG. 2A  FIG. 2B  FIG. 2C  FIG. 2D
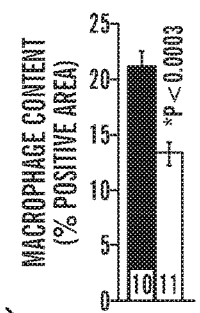 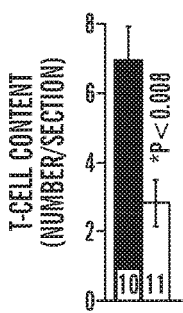 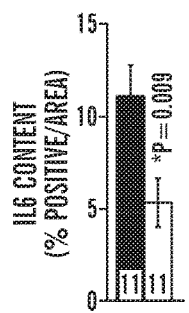 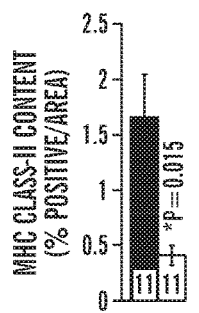
FIG. 2E
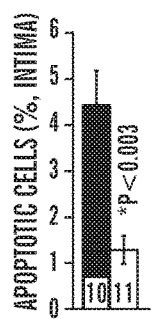 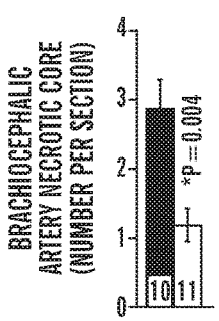 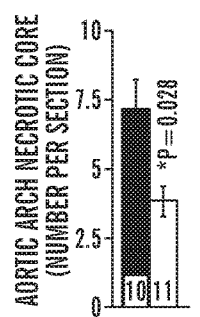
FIG. 2F  FIG. 2G

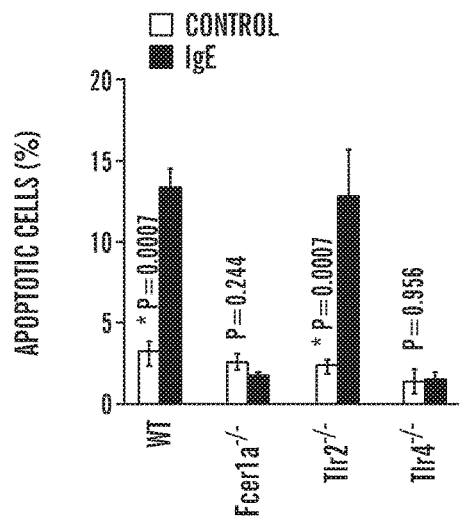
*FIG. 3I*
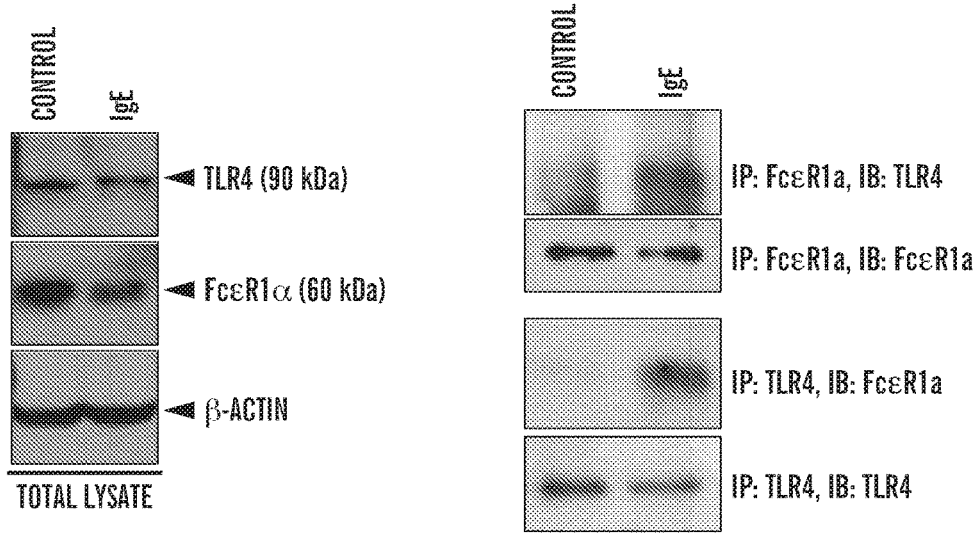
*FIG. 3J*  *FIG. 3K*

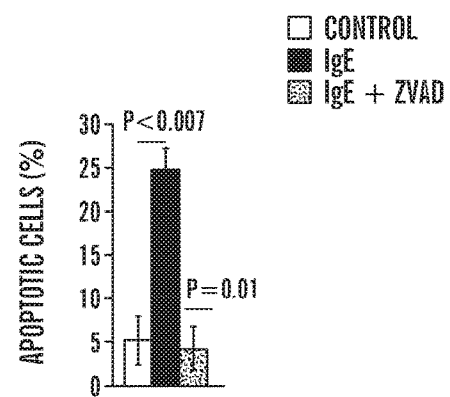
FIG. 4A
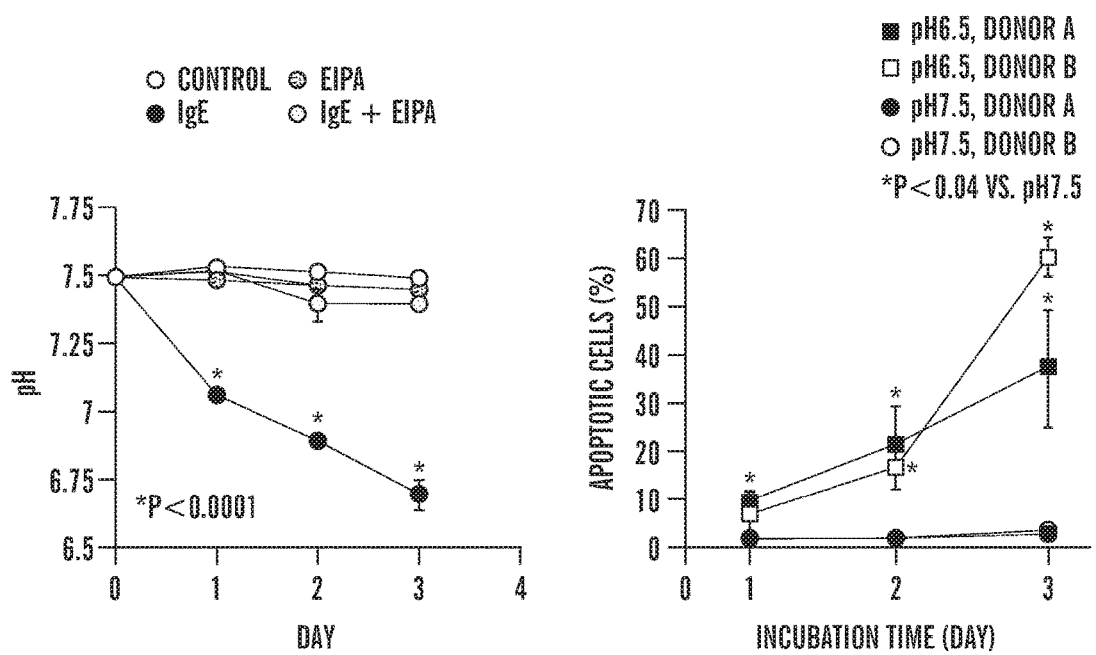
FIG. 4B
FIG. 4C

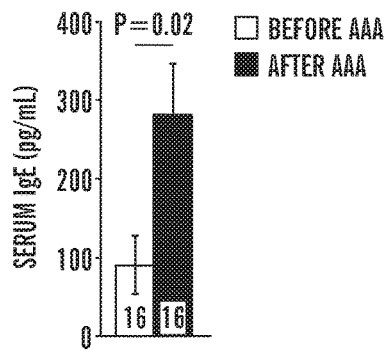
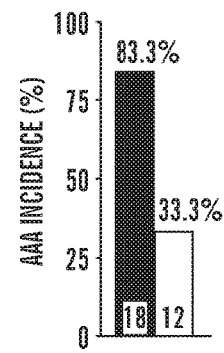
FIG. 12A  FIG. 12B
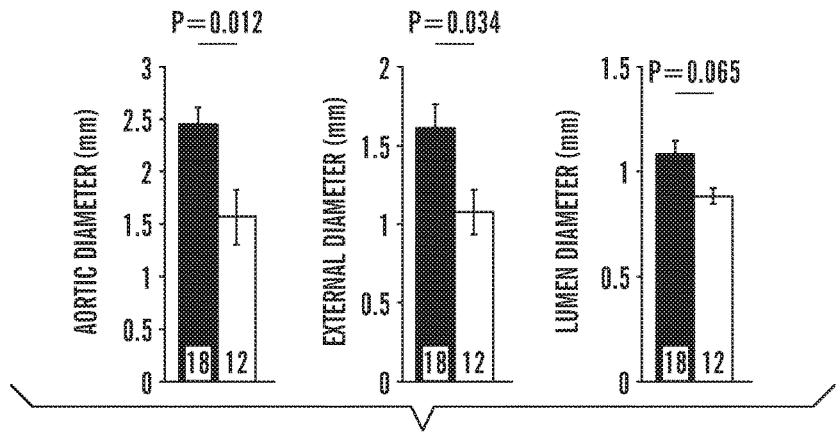
FIG. 12C
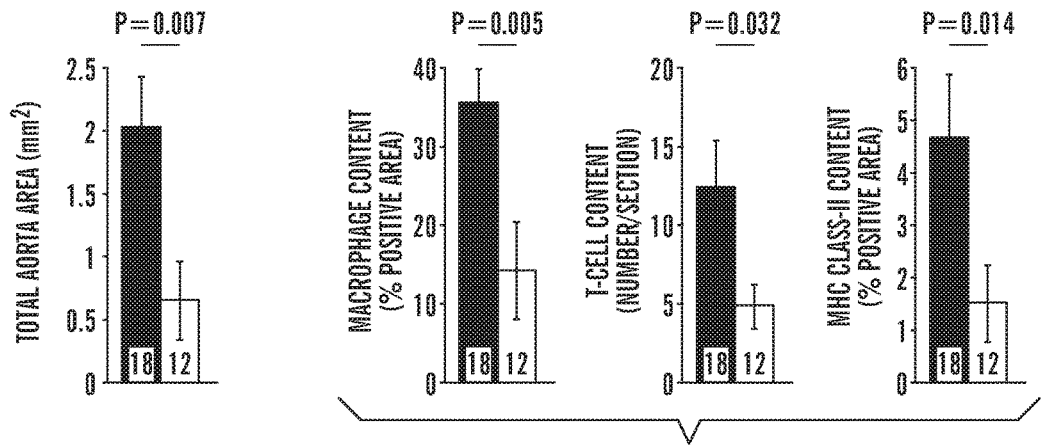
FIG. 12D  FIG. 12E

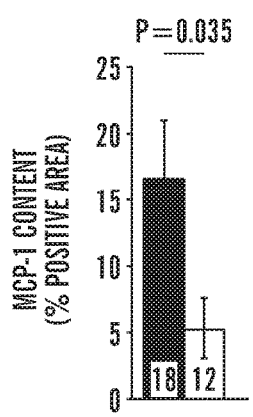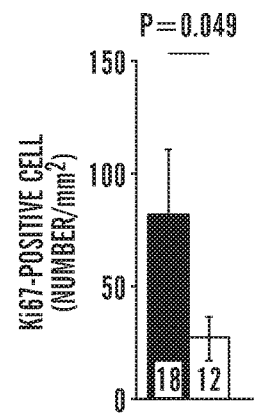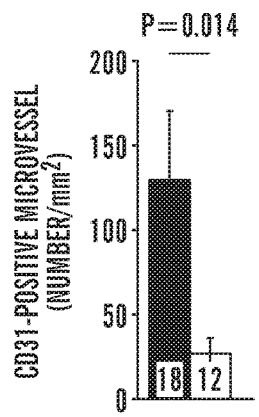
FIG. 12F     FIG. 12G     FIG. 12H
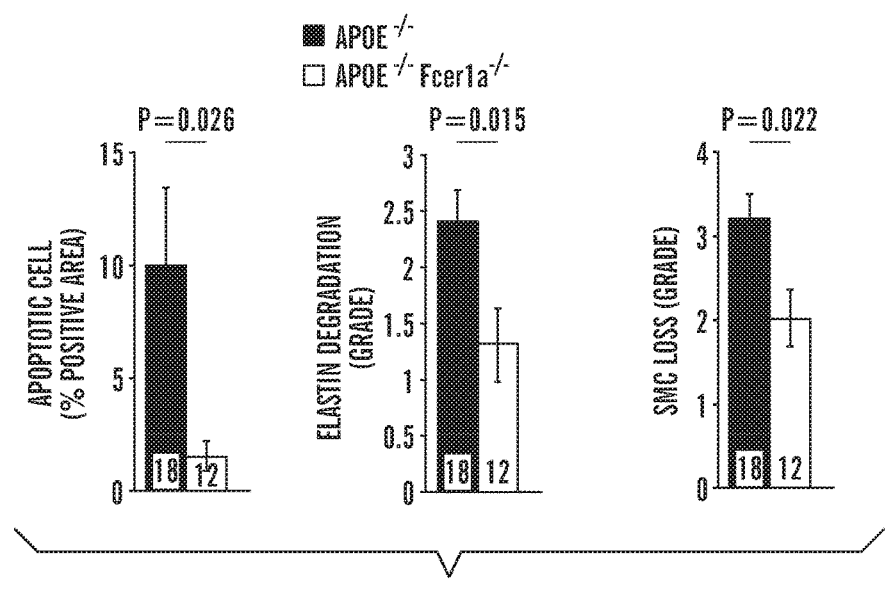
FIG. 12I

METHODS OF TREATING ATHEROSCLEROSIS AND ANEURYSM

CROSS REFERENCE TO RELATED APPLICATIONS

This application is a 35 U.S.C. 371 National Phase Entry Application of International Application No. PCT/US2012/049746, filed Aug. 6, 2012, which designates the United States, and which claims the benefit under 35 U.S.C. 119(e) of U.S. Provisional Patent Application Ser. No. 61/514,992, filed Aug. 4, 2011, the contents of which are herein incorporated by reference in its entirety.

GOVERNMENT SUPPORT

This invention was made with federal funding under Grant Nos. HL60942, HL81090, HL88547 awarded by the National Institutes of Health. The U.S. government has certain rights in the invention.

SEQUENCE LISTING

The instant application contains a Sequence Listing which has been submitted in ASCII format via EFS-Web and is hereby incorporated by reference in its entirety. Said ASCII copy, created on Jan. 30, 2014, is named 4321475PC.txt and is 3,331,786 bytes in size.

TECHNICAL FIELD

The technology described herein relates to treatments for cardiovascular and metabolic diseases.

BACKGROUND

Immunoglobulin E (IgE) is an important regulator of allergic reactions, in which it activates mast cells (MCs) by binding to its high-affinity receptor FcεR1 (Kinet J P. Annu Rev Immunol. 1999; 17:931-972). IgE is the least abundant antibody isotype in humans, and its role in human immunology (other than its effects on allergy and parasitic infection) has long been unclear. In addition to MCs, lymphocytes, dendritic cells, eosinophils, platelets, monocytes, and macrophages also bear FcεR1 on their surfaces, albeit in different assemblages. For example, FcεR1 on MCs is a heterotetramer ($\alpha\beta\gamma_2$), whereas FcεR1 on macrophages or eosinophils is a heterotrimer ($\alpha\gamma_2$). In dendritic cells, the expression of FcεR1 affects IFN-γ-mediated pro-inflammatory (tumor necrosis factor-α [INF-α]) and anti-inflammatory (IL-10) cytokine production, as well as the efficiency of antigen uptake and presentation.

SUMMARY

The technology described herein is directed to methods of treating cardiovascular and metabolic diseases by administering an inhibitor of IgE signaling.

In one aspect, the technology described herein relates to the use of an IgE signaling inhibitor to treat a subject in need of treatment for a condition selected from the group consisting of: atherosclerosis; aneurysm; aortic aneurysm; aortic aneurysm; diabetes; and obesity. In one aspect, the technology described herein relates to a method comprising, administering a therapeutically effective amount of an IgE signaling inhibitor to a subject in need of a treatment for atherosclerosis. In one aspect the technology described herein relates to a method comprising, administering a therapeutically effective amount of an IgE signaling inhibitor to a subject in need of a treatment for aortic aneurysm. In one aspect, the technology described herein relates to a method comprising, administering a therapeutically effective amount of an IgE signaling inhibitor to a subject in need of a treatment for diabetes. In one aspect, the technology described herein relates to a method comprising, administering a therapeutically effective amount of an IgE signaling inhibitor to a subject in need of a treatment for obesity.

In some embodiments, the IgE signaling inhibitor can be an IgE inhibitor. In some embodiments, the IgE inhibitor can be selected from the group consisting of; an anti-IgE monoclonal antibody; omalizumab; and talizumab. In some embodiments, the IgE signaling inhibitor can be an IgE receptor inhibitor.

BRIEF DESCRIPTION OF THE DRAWINGS

FIG. 1A depicts localization of IgE and FcεR1α in CD68$^+$ macrophage-rich areas in human atherosclerotic lesions. Magnifications: top panels: 40×, bottom panels: 100×. FIG. 1B depicts localization of IgE and FcεR1α in α-actin-positive SMC-rich fibrous cap (top panels, 100×) and media (bottom panels, 100×). FIG. 1C depicts localization of IgE (100×) and FcεR1α (400×) in luminal ECs (100×) (arrows). Antibody isotype control was used as a negative control (100×). FIG. 1D depicts FcεR1α immunoblot analysis in human monocyte-derived macrophages and in HuSMCs and HuECs treated without (−) and with (+) inflammatory cytokine IFN-γ. Each lane contains 20 μg cell lysate (top panel). Actin immunoblot ensured equal protein loading. Bottom panel, 2 μg of human macrophage (Mac) lysate and 50 μg of HuEC and HuSMC lysates to enhance the detection of FcεR1α in SMCs and ECs. IFN-γ (20 ng/mL) induced FcεR1α expression in SMCs (lanes 2 and 3) and ECs (lanes 5 and 6).

FIGS. 2A-2G demonstrate that deficiency of FcεR1α reduced atherogenesis in Apoe$^{-/-}$ mice. FIG. 2A depicts serum IgE levels in Apoe$^{-/-}$ mice before (−HFD) and after (+HFD) consuming a high-fat diet (HFD) for 12 weeks. FIG. 2B depicts thoracic-abdominal aorta lipid deposition (oil-red O staining). FIG. 2C depicts a graph of Intima area. FIG. 2D depicts a graph of Media area. FIG. 2E depicts a graph of Aortic arch atherosclerotic lesion macrophage content, CD3$^+$ T-cell content, IL6-positive area, and MHC class-II content. FIG. 2F depicts a graph of lesion TUNEL-positive apoptosis cells. FIG. 2G depicts brachiocephalic artery and aortic arch necrotic core (#) numbers. The number of mice per group is indicated in each bar. Data are mean±SEM. $P<0.05$ is considered statistically significant; Mann-Whitney U test.

FIGS. 3A-3K depict mouse peritoneal macrophage IgE (SPE-7) responses. Immunoblots to detect signaling molecule activation in IgE-treated macrophages at different times (50 μg/mL IgE) (FIG. 3A) or with different doses of IgE (15 minutes) (FIG. 3B). FIG. 3C depicts immunoblots to detect signaling molecule activation in IgE-treated macrophages from WT and Fcer1a$^{-/-}$ mice. FIG. 3D depicts macrophage lysate JPM labeling to detect active cathepsins (arrowheads) in macrophages treated without (−) or with (+) IgE for 2 days. FIG. 3E depicts WT macrophage phospho-p65 and phospho-JNK expression after 15 minutes of treatment with IgE, heated IgE, and LPS (100 ng/mL). FIG. 3F depicts IgE-stimulated phospho-p65 and phospho-JNK expression in macrophages from different mice. FIGS. 3G and 3H. IgE-induced IL-6 and MCP-1 mRNA (RT-PCR; FIG. 3G) and media protein (ELISA; FIG. 3H) levels in macrophages from different mice. FIG. 3I depicts quantification of the immunofluorescent TUNEL staining of IgE-induced apoptosis (3 days) in macrophages from different mice. FIG. 3J depicts immunoblots to detect TLR4 and FcεR1α in macrophage total lysates before and after IgE stimulation (15 minutes). FIG. 3K depicts immunoprecipitation (IP) results for FcεR1α or TLR4 followed by immunoblot (IB) analysis for TLR4 or FcεR1α in macrophages treated with and without IgE (15 minutes). The same IP antibody was used for IB to ensure equal antibody precipitation. Except where indicated, 50 μg/mL of IgE or heated IgE were used for all macrophage stimulations. Total p38, p65, or β-actin immunoblots were used for protein loading controls. Data in panels 3G-3I are mean±SEM of six to ten experiments. $P<0.05$ is considered statistically significant; Mann-Whitney U test.

FIGS. 4A-4E depict IgE-induced human macrophage apoptosis and cytokine production. FIG. 4A demonstrates that fluorescent TUNEL staining detected human monocyte-derived macrophage apoptosis (fluorescent cells) after 3 days of stimulation with or without human IgE (50 μg/mL) or caspase inhibitor ZVAD (20 μM). Data are mean±SEM from six experiments using macrophages from the same donor. FIG. 4B depicts IgE-induced macrophage RPMI medium pH reduction. Inhibition with NHE1 inhibitor EIPA (10 μM) blocked IgE-induced pH reduction. EIPA alone was used as experimental control. Data are mean±SEM from four donors. *$P<0.05$ was considered statistically significant compared with untreated cells. FIG. 4C depicts pH-dependent apoptosis (by TUNEL staining) of human macrophages from different donors. Each treatment used macrophages from two donors (A and B). *$P<0.05$ was considered statistically significant for the comparison between pH 6.5 and pH 7.5. FIGS. 4D-4E depicts IgE-induced cell death (by MTT assay; FIG. 4D) and IL16 production (FIG. 4E) from macrophages from four donors (A, B, C, and D). Data are mean±SEM from four experiments in panels. In FIGS. 4C-4E a final concentration of 50 μg/mL purified human IgE was used for all experiments.

FIG. 5A depicts culture medium IL-6 in macrophages treated with and without IgE and different concentrations of NHE1 inhibitor EIPA. FIG. 5B depicts IgE-induced macrophage apoptosis (TUNEL staining) and inhibition with different concentrations of EIPA. Data are mean±SEM from six experiments. $P<0.05$ is considered statistically significant. FIG. 5C depicts immunoblot analysis to detect IgE-treated macrophage mitochondria cytochrome C and cytosol Bax. X denotes a cross-reacting protein with the cytochrome C antibody. FIG. 5D depicts macrophage cell death under difference conditions. FIG. 5E depicts NHE1 immunoblot in macrophages treated with IgE for different times. FIG. 5F depicts RT-PCR to detect NHE-1 mRNA levels in atherosclerotic lesions from different mice. FIG. 5G depicts pH change, IL6 production, and cell death of macrophages from $Nhe1^{+/+}$ mice and $Nhe1^{+/-}$ mice after 3 days of treatment without (Control) or with IgE. All experiments used 50 μg/mL mouse IgE (SPE-7). Actin immunoblot was used for protein loading control. Cell death was determined with a MTT assay on a 96-well plate with $5 \times 10^4$ macrophages per well.

FIG. 6D depicts the synergistic effect of SPE-7 (50 μg/mL) with LPS (100 ng/mL) or ox-LDL (50 μg/mL) in macrophage IL6 production. Cell death and media IL6 were determined by MTT assay and ELISA, respectively.

FIG. 7A depicts IgE and TUNEL reactivity in adventitial microvessels (V, left two panels) and TUNEL activity in luminal ECs and fibrous cap SMCs (right two panels, corresponding to FIGS. 1B and 1C, top panels) in human atherosclerotic lesions. Magnifications: 100×, inserts: 400×. FIG. 7B depicts Phospho-p38 and phospho-JNK immunoblots in HuECs stimulated with IgE (15 minutes). FIG. 7C depicts cleaved caspase-3 immunoblot in HuECs treated without (−) and with (+) IgE. FIG. 7D depicts HuEC cell death induced with different concentrations of human IgE. FIG. 7E depicts IgE-induced cell death of different numbers of HuECs. FIG. 7F depicts phospho-p38 and phospho-JNK immunoblots in HuSMCs after IgE stimulation at different time points. FIG. 7G depicts BAX expression in HuSMCs treated with or without IgE. FIG. 7H depicts HuSMC cell death after IgE treatment. Representative images are shown to the left. FIG. 7I depicts HuSMC cell death after treatment with different concentrations of IgE. FIG. 7J depicts phospho-p65 and phospho-ERK1/2 immunoblots in HuSMCs, treated with or without IgE for different times. FIG. 7K depicts Culture medium IFN-γ, TNF-β, and IL6 in HuSMCs, treated with or without IgE for 2 days. FIG. 7L depicts sathepsin JPM labeling of HuSMCs before and after IgE stimulation. Arrowheads indicate different active cathepsins. Except where indicated, 100 μg/mL human IgE was used for all HuEC and HuSMC experiments. Data in FIGS. 7D, 7E, 7H, 7I, and 7K are mean±SEM from 6~10 experiments. Cell death from FIGS. 7D, 7H, and 7I used MTT assays, and FIG. 7E used CyQUANT cell proliferation assay. $P<0.05$ is considered statistically significant; Mann-Whitney U test.

FIG. 11A depicts the results of RT-PCR to detect mRNA levels. FIG. 11B depicts the results of immunoblot analysis to detect protein levels. TNF-α was used as a positive control, and actin blot was used to ensure equal protein loading.

FIGS. 12A-12I demonstrate that in mice, serum IgE levels are increased after Apoe$^{-/-}$ mice develop AAA (FIG. 12A). For FIG. 12A, the white bar represents measurements made before AAA; the black bar represents measurements made before AAA. Absence of IgE receptor FcεR1 protected Apoe$^{-/-}$ mice from AAA formation (FIGS. 12B-12I). For FIGS. 12B-12I, the white bar represents measurements made from Apoe$^{-/-}$ mice; the black bar represents measurements made from Apoe-/-Fcε1a-/- mice.

DETAILED DESCRIPTION

Figure 1B:
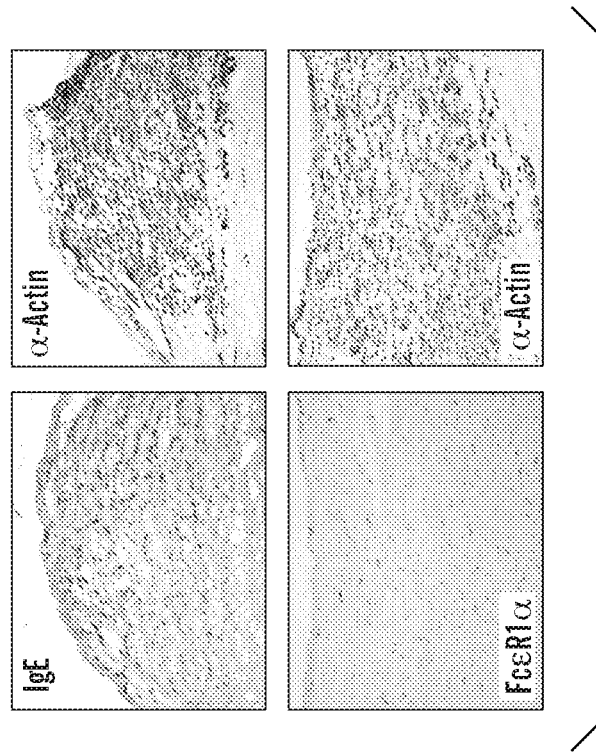
FIGS. 1A-1D depict IgE and FcεR1α expression in human atherosclerotic lesions and in human macrophages, SMCs, and ECs.

Embodiments of the technology described herein relate to methods of treatment comprising administering an inhibitor of IgE signaling to a subject in need of treatment for a cardiovascular or metabolic disease. In some embodiments, the inhibitor can be an IgE inhibitor. In some embodiments, the inhibitor can be an IgE receptor inhibitor.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein generally to mean a decrease by a statistically significant amount. However, for avoidance of doubt, "reduced", "reduction", "decrease", or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level or non-detectable level as compared to a reference level), or any decrease between 10-100% as compared to a reference level. In the context of a marker or symptom is meant a statistically significant decrease in such level. The decrease can be, for example, at least 10%, at least 20%, at least 30%, at least 40% or more, and is preferably down to a level accepted as within the range of normal for an individual without such disorder.

The terms "increased", "increase", "enhance", or "activate" are all used herein to generally mean an increase by a statically significant amount; for the avoidance of doubt, the terms "increased", "increase", "enhance", or "activate" mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, or canine species, e.g., dog, fox, wolf. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of cardiovascular or metabolic disease. A subject can be male or female.

A subject can be one who has been previously diagnosed with or identified as suffering from or having a condition in need of treatment (e.g. atherosclerosis) or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

As used herein, the term "proteins" and "polypeptides" are used interchangeably herein to designate a series of amino acid residues connected to the other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the template nucleic acid is DNA. In another aspect, the template is RNA. Suitable nucleic acid molecules are DNA, including genomic DNA or cDNA. Other suitable nucleic acid molecules are RNA, including mRNA.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. atherosclerosis. The term "treating" includes reducing or alleviating at least one adverse effect or symptom of a condition, disease or disorder associated with a condition described herein, e.g. atherosclerosis. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutical composition" refers to the active agent in combination with a pharmaceutically acceptable carrier e.g. a carrier commonly used in the pharmaceutical industry.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The terms "compound" and "agent" refer to any entity which is normally not present or not present at the levels being administered to a cell, tissue or subject. An agent can be selected from a group comprising: chemicals; small organic or inorganic molecules; nucleic acid sequences; nucleic acid analogues; proteins; peptides; aptamers; peptidomimetic, peptide derivative, peptide analogs, antibodies; intrabodies; biological macromolecules, extracts made from biological materials such as bacteria, plants, fungi, or animal cells or tissues; naturally occurring or synthetic compositions or functional fragments thereof. In some embodiments, the agent is any chemical, entity or moiety, including without limitation synthetic and naturally-occurring non-proteinaceous entities. In certain embodiments the agent is a small molecule having a chemical moiety. For example, chemical moieties include unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

The term "statistically significant" or "significantly" refers to statistical significance and generally means a two standard deviation (2SD) below normal, or lower, concentration of the marker.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and the include plural referents unless context clearly indicates otherwise. Similarly, the word or is intended to include and unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); The ELISA guidebook (Methods in molecular biology 149) by Crowther J. R. (2000). Definitions of common terms in molecular biology can also be found in Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

In one aspect, the technology described herein relates to a method comprising, administering a therapeutically effective amount of an IgE signaling inhibitor to a subject in need of a treatment for a cardiovascular or metabolic disease. In one aspect, the technology described herein relates to the use of an IgE signaling inhibitor to treat a subject in need of treatment for a cardiovascular or metabolic disease. In some embodiments, the cardiovascular or metabolic disease can be selected from the group consisting of: atherosclerosis, abdominal aortic aneurysm, diabetes, and obesity. In some embodiments, the methods described herein further comprise selected a subject in need of treatment for a condition selected from the group consisting of: atherosclerosis, abdominal aortic aneurysm, diabetes, and obesity. As described herein, IgE levels can correlate with plaque instability, diabetes status, and blood glucose levels and inhibiting IgE itself, or signaling events induced by IgE, can inhibit the progression of cardiovascular and metabolic diseases.

As used herein, the term "atherosclerosis" refers to a disease of the arterial blood vessels resulting in the hardening of arteries caused by the formation of multiple atheromatous plaques within the arteries. Atherosclerosis can be associated with other disease conditions, including but not limited to, coronary heart disease events, cerebrovascular events, acute coronary syndrome, and intermittent claudication. For example, atherosclerosis of the coronary arteries commonly causes coronary artery disease, myocardial infarction, coronary thrombosis, and angina pectoris. Atherosclerosis of the arteries supplying the central nervous system frequently provokes strokes and transient cerebral ischemia. In the peripheral circulation, atherosclerosis causes intermittent claudication and gangrene and can jeopardize limb viability. Atherosclerosis of an artery of the splanchnic circulation can cause mesenteric ischemia. Atherosclerosis can also affect the kidneys directly (e.g., renal artery stenosis). Also, persons who have previously experienced one or more non-fatal atherosclerotic disease events are those for whom the potential for recurrence of such an event exists.

As used herein, the term "aneurysm" refers to a localized, blood-filled dilation (balloon-like bulge) of a blood vessel caused by disease or weakening of the vessel wall. Aneurysms most commonly occur in arteries at the base of the brain (the circle of Willis) and in the aorta (the main artery coming out of the heart, an aortic aneurysm). As the size of an aneurysm increases, there is an increased risk of rupture, which can result in severe hemorrhage, other complications or even death. "Aneurysm" further means not only conventional vascular aneurysms, but also refers to any abnormal localized dilatations of blood vessels. In some embodiments, an aneurysm can be a thoracic aneurysm, an intracranial aneurysm, a microvessel aneurysm, or an aortic aneurysm. As used herein, the term "aortic aneurysm" refers to a dilatation of the aorta. In certain instances, the rupture of an aortic aneurysm results in bleeding, leading to hypovolemic shock with hypotension, tachycardia, cyanosis, and altered mental status. In some embodiments, an aortic aneurysm can be an abdominal aortic aneurysm, a descending aortic aneurysm, an ascending aortic aneurysm, and/or a stress aneurysm. As used herein, the term "abdominal aortic aneurysm" or "AAA" refers to a localized dilatation of the abdominal aorta.

As used herein, the term "diabetes" refers to diabetes mellitus, a metabolic disease characterized by a deficiency or absence of insulin secretion by the pancreas. As used throughout, "diabetes" includes Type 1, Type 2, Type 3, and Type 4 diabetes mellitus unless otherwise specified herein. As used herein, the term "diabetes" refers a syndrome of disordered metabolism, usually due to a combination of hereditary and environmental causes, resulting in abnormally high blood sugar levels (hyperglycemia). The two most common forms of diabetes are due to either a diminished production of insulin (in type 1), or diminished response by the body to insulin (in type 2 and gestational). Both lead to hyperglycemia, which largely causes the acute signs of diabetes: excessive urine production, resulting compensatory thirst and increased fluid intake, blurred vision, unexplained weight loss, lethargy, and changes in energy metabolism. Diabetes can cause many complications. Acute complications (hypoglycemia, ketoacidosis, or nonketotic hyperosmolar coma) may occur if the disease is not adequately controlled. Serious long-term complications (i.e. chronic side effects) include cardiovascular disease (doubled risk), chronic renal failure, retinal damage (which can lead to blindness), nerve damage (of several kinds), and microvascular damage, which may cause impotence and poor wound healing. Poor healing of wounds, particularly of the feet, can lead to gangrene, and possibly to amputation. In some embodiments, the diabetes can be Type 2 diabetes. Type 2 diabetes (non-insulin-dependent diabetes mellitus (NIDDM), or adult-onset diabetes) is a metabolic disorder that is primarily characterized by insulin resistance (diminished response by the body to insulin), relative insulin deficiency, and hyperglycemia. In some embodiments, a subject can be pre-diabetic, which can be characterized, for example, as having elevated fasting blood sugar or elevated post-prandial blood sugar.

As used herein, the term "obesity" refers to a condition characterized by an excess of body fat. The operational definition of obesity is based on the Body Mass Index (BMI), which is calculated as body weight per height in meter squared (kg/m2). Obesity refers to a condition whereby an otherwise healthy subject has a BMI greater than or equal to 30 kg/m2, or a condition whereby a subject with at least one co-morbidity has a BMI greater than or equal to 27 kg/m2. An "obese subject" is an otherwise healthy subject with a BMI greater than or equal to 30 kg/m2 or a subject with at least one co-morbidity with a BMI greater than or equal 27 kg/m2. A "subject at risk of obesity" is an otherwise healthy subject with a BMI of 25 kg/m2 to less than 30 kg/m2 or a subject with at least one co-morbidity with a BMI of 25 kg/m2 to less than 27 kg/m2. An "overweight subject" is an otherwise healthy subject with a BMI of 25 kg/m2 to less than 30 kg/m2 or a subject with at least one co-morbidity with a BMI of 25 kg/m2 to less than 27 kg/m2.

In some embodiments, the methods described herein relate to inhibitor of IgE signaling. As used herein, the term "IgE" refers to an isotype class of antibodies found in mammals which is the least abundant antibody isotype. IgE is comprised of a light chain (e.g. NCBI Gene ID: 50802 or 3535) and a heavy chain (e.g. NCBI Gene ID: 3497). The sequences of IgE nucleic acids and polypeptides in a number of species are known in the art (see, e.g. Schwarzbaum et al. Eur J Immunol 1989 19:1015-1023; Bjorklund et al. Mol Immunol 2000 37:169-177; Garman et al. Nature 2000 406:259-266; which are incorporated by reference herein in their entireties). It is noted that the sequence of each monoclonal IgE molecule will vary, but the Fc region of the heavy chains will be constant and are the section which interact with receptor molecule on the cell surface. The interaction between IgE and the high affinity FcReRI receptor can involve the Cε3 domain of the IgE Fc region of the heavy chain. As used herein, the term "IgE signaling inhibitor" refers to an agent which reduces the level of IgE polypeptide and/or mRNA or which reduces the level of a signal or activity induced by IgE. IgE signaling inhibitors can inhibit IgE signaling via any known mechanism, including, e.g., binding of a competitive inhibitor, binding of a non-competitive inhibitor, increasing the rate of degradation of IgE signaling pathway polypeptides, blocking the biosynthesis, transcription, and/or translation of a component of IgE signaling and blocking the binding of IgE to a receptor molecule. IgE signaling inhibition can be determined by methods well known in the art, e.g. by detecting the level of IgE-induced apoptosis as described herein. In certain embodiments, an agent can increase or decrease the expression of a component of the targeted signaling pathway. Components of the IgE signaling pathway include, but are not limited to SYK, LYN, FcεRI, LAT, SOS, Ras, Vav, PLC, MEK, and ERK. The IgE signaling pathways have been described in the art, e.g. Gilfillan and Tkaczyk. Nature Reviews Immunology 2006 6:218-230 and Falcone et al. Blood 2000 96:4028-4038; which are incorporated by reference herein in their entireties. Transcriptional assays are well known to those of skill in the art (see e.g. U.S. Pat. Nos. 7,319,933, 6,913,880 which is incorporated herein by reference in its entirety). In some embodiments, an IgE signaling inhibitor can be an IgE inhibitor. In some embodiments, an IgE signaling inhibitor can be an IgE receptor inhibitor.

As used herein, the term "IgE inhibitor" refers to an agent which inhibits the biological activity of IgE by interacting with IgE or which inhibits the expression of IgE, e.g. an agent which reduces the level of IgE polypeptide or which reduces the ability of IgE to bind one or more of its receptors. In some embodiments, an IgE inhibitor can reduce the expression level of IgE mRNA. In some embodiments, an IgE inhibitor can reduce the expression level of IgE polypeptide. In some embodiments, an IgE inhibitor can bind to IgE and inhibit binding of IgE with a receptor molecule.

Non-limiting examples of IgE inhibitors can include omalizumab (Xolair); talizumab (TNX-901); oligonucleotides as described in Wiegand et al. J Immunol 1996 157:221-230; peptides as described in Buku et al. J Pept Res 2005 66:132-137 and inhibitors described in, e.g. U.S. Pat. Nos. 5,543,144, 5,656,273, 5,449,760, 7,384656; 7,759,357 and US Patent Publications US 2002/0132808

As used herein, the term "IgE receptor inhibitor" refers to an agent which inhibits the biological activity of an IgE receptor by interacting with the receptor or which inhibits the expression of an IgE receptor. In some embodiments, an IgE receptor inhibitor can reduce the expression level of an IgE receptor mRNA. In some embodiments, an IgE receptor inhibitor can reduce the expression level of an IgE receptor polypeptide. In some embodiments, an IgE receptor inhibitor can bind to an IgE receptor and inhibit binding of IgE with the receptor molecule. As used herein, the term "IgE receptor" refers to cell surface Fc receptors which recognize and bind to IgE, thereby inducing a signaling cascade. In some embodiments, the IgE receptor can be FcεRI (the high-affinity IgE receptor). In some embodiments, the IgE receptor can be FcεRII (also referred to as CD23; the low-affinity IgE receptor; NCBI Gene ID: 2208). FcεRI molecule can be comprised of one or more alpha chains (FcεRIα; NCBI Gene ID: 2205), one or more beta chains (FcεRIβ; NCBI Gene ID: 2206), and/or one or more gamma chains (FcεRIγ; NCBI Gene ID: 2207). The sequence of FcεRI nucleic acids and polypeptides in a number of species are known in the art (e.g. human FcεRIα nucleic acid (NCBI Ref Seq: NM_002001 (SEQ ID NO: 7) and polypeptide (NCBI Ref Seq: NP_001992 (SEQ ID NO: 8); human FcεRIβ nucleic acid (NCBI Ref Seq: NM_000139 (SEQ ID NO:9) and NCBI Ref Seq: NM_001256916 (SEQ ID NO:10)); and polypeptide (NCBI Ref Seq: NP_000130 (SEQ ID NO:11) and NCBI Ref Seq: NP_001243845 (SEQ ID NO:12); and human FcεRIγ nucleic acid (NCBI Ref Seq:NM_004106 (SEQ ID NO: 13)); and polypeptide (NCBI Ref Seq: NP_004097 (SEQ ID NO: 14). The sequence of FcεRII nucleic acids and polypeptides in a number of species are known in the art (e.g. human FcεRII nucleic acid (NCBI Ref Seq:NM_001207019 (SEQ ID NO:1); NCBI Ref Seq: NM_001220500 (SEQ ID NO: 2); NCBI Ref Seq: NM_002002 (SEQ ID NO:3)) and human amino acid (NCBI Ref Seq: NP_001193948 (SEQ ID NO: 4); NCBI Ref Seq: NP_001207429 (SEQ ID NO: 5); NCBI Ref Seq: NP_001993 (SEQ ID NO:6)).

In some embodiments, gene silencing or RNAi can be used to inhibit IgE signaling. In certain embodiments, contacting a cell with the IgE signaling inhibitor results in a decrease in the mRNA level in a cell for a target gene (e.g. IgE) by at least about 10%, e.g., at least about 20%, about 30%, about 40%, about 50%, about 60%, about 70%, about 80%, about 90%, about 95%, about 99%, or more of the mRNA level found in the cell without the presence of the miRNA or RNA interference (RNAi) molecule. In one embodiment, the mRNA levels are decreased by at least about 30%, about 40%, about 50%, about 60%, about 70%, about 80%, about 90%, about 95%, about 99%, or more, i.e., no detectable target mRNA. In certain embodiments, the agent comprises an expression vector or viral vector comprising the RNAi molecule. Methods of assaying the ability of an agent to inhibit translation of a gene, e.g. IgE, are known to those of ordinary skill in the art. Gene translation can be measured by quantitation of protein expressed from a gene, for example by Western blotting, by an immunological detection of the protein, ELISA (enzyme-linked immunosorbent assay), Western blotting, radioimmunoassay (RIA) or other immunoassays and fluorescence-activated cell analysis (FACS) to detect protein.

As used herein, the term "RNAi" refers to any type of interfering RNA, including but are not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein). The term "RNAi" and "RNA interfering" with respect to an IgE signaling inhibitor are used interchangeably herein.

As used herein a "siRNA" refers to a nucleic acid that forms a double stranded RNA, which double stranded RNA has the ability to reduce or inhibit expression of a gene or target gene when the siRNA is present or expressed in the same cell as the target gene, e.g. IgE. The double stranded RNA siRNA can be formed by the complementary strands. In one embodiment, a siRNA refers to a nucleic acid that can form a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA" are used interchangeably herein are endogenous RNAs, some of which are known to regulate the expression of protein-coding genes at the posttranscriptional level. Endogenous microRNA are small RNAs naturally present in the genome which are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 116:281-297), comprises a dsRNA molecule.

As used herein, the term "complementary" or "complementary base pair" refers to A:T and G:C in DNA and A:U in RNA. Most DNA consists of sequences of nucleotide only four nitrogenous bases: base or base adenine (A), thymine (T), guanine (G), and cytosine (C). Together these bases form the genetic alphabet, and long ordered sequences of them contain, in coded form, much of the information present in genes. Most RNA also consists of sequences of only four bases. However, in RNA, thymine is replaced by uridine (U).

In some embodiments, in order to increase nuclease resistance of an IgE signaling inhibitor comprising a nucleic acid as disclosed herein, one can incorporate non-phosphodiester backbone linkages, as for example methylphosphonate, phosphorothioate or phosphorodithioate linkages or mixtures thereof. Other functional groups may also be joined to the oligonucleoside sequence to instill a variety of desirable properties, such as to enhance uptake of the oligonucleoside sequence through cellular membranes, to enhance stability or to enhance the formation of hybrids with the target nucleic acid, or to promote cross-linking with the target (as with a psoralen photo-cross-linking substituent). See, for example, PCT Publication No. WO 92/02532 which is incorporated herein in by reference.

An IgE signaling inhibitor can comprise a vector. Many vectors useful for transferring exogenous genes into target mammalian cells are available, e.g. the vectors may be episomal, e.g., plasmids, virus derived vectors such cytomegalovirus, adenovirus, etc., or may be integrated into the target cell genome, through homologous recombination or random integration, e.g., retrovirus derived vectors such MMLV, HIV-1, ALV, etc. Many viral vectors are known in the art and can be used as carriers of a nucleic acid modulatory compound into the cell. For example, constructs containing the modulatory compound may be integrated and packaged into non-replicating, defective viral genomes like Adenovirus, Adeno-associated virus (AAV), or Herpes simplex virus (HSV) or others, including retroviral and lentiviral vectors, for infection or transduction into cells. Alternatively, the construct may be incorporated into vectors capable of episomal replication, e.g. EPV and EBV vectors. The nucleic acid incorporated into the vector can be operatively linked to an expression control sequence when the expression control sequence controls and regulates the transcription and translation of that polynucleotide sequence.

In certain embodiments, the IgE signaling inhibitor can be a protein or peptide. A peptide agent can be a fragment of a naturally occurring protein, or a mimic or peptidomimetic. Agents in the form of a protein and/or peptide or fragment thereof can be designed to decrease the level and/or activity of IgE as described herein, i.e. decrease IgE gene expression or decrease the encoded protein IgE activity. Such agents are intended to encompass proteins which are normally absent as well as proteins normally endogenously expressed within a cell, e.g. expressed at low levels. Examples of useful proteins are mutated proteins, genetically engineered proteins, peptides, synthetic peptides, recombinant proteins, chimeric proteins, modified proteins and fragments thereof. A decrease in IgE gene expression or protein IgE activity can be direct or indirect. In one embodiment, a protein/peptide agent directly binds to a protein which is a component of the targeted polypeptide, or directly binds to a nucleic acid which encodes such a protein.

In one embodiment, protein/peptide agents (including antibodies or fragments thereof) can be assessed for their ability to bind an encoded protein in vitro. Examples of direct binding assays include, but are not limited to, labeled in vitro protein-protein binding assays, electrophoretic mobility shift assays, immunoassays for protein binding, ELISA assays, co-immunoprecipitation assays, competition assays (e.g. with a known binder), and the like. See, e.g., U.S. Pat. Nos. 4,366,241; 4,376,110; 4,517,288; and 4,837, 168; and also Bevan et al., Trends in Biotechnology 13:115-122, 1995; Ecker et al., Bio/Technology 13:351-360, 1995; and Hodgson, Bio/Technology 10:973-980, 1992. The agent can also be assayed or identified by detecting a signal that indicates that the agent binds to a protein of interest e.g., fluorescence quenching or FRET. Polypeptides can also be monitored for their ability to bind nucleic acid in vitro, e.g. ELISA-format assays can be a convenient alternative to gel mobility shift assays (EMSA) for analysis of protein binding to nucleic acid. Binding of an agent to an encoded protein provides an indication the agent may increase or decrease protein activity.

In certain embodiments, the IgE signaling inhibitor can be an antibody, e.g. a neutralizing antibody (See, generally, Hood et al., Immunology, Benjamin, N.Y., 2ND ed. (1984), Harlow and Lane, Antibodies. A Laboratory Manual, Cold Spring Harbor Laboratory (1988) and Hunkapiller and Hood, Nature, 323, 15-16 (1986), which are incorporated herein by reference). Monoclonal antibodies can be prepared using methods well known to those of skill in the art. Methods for intrabody production are well known to those of skill in the art, e.g. as described in WO 2002/086096; which is incorporated herein by reference in its entirety. Antibodies that specifically bind to a target polypeptide, (e.g. an IgE polypeptide) will usually bind with at least a KD of about 30 µM, preferably at least about 10 µM, and more preferably at least about 3 µM or better, e.g., 100 µM, 50 µM, 1 µM or better.

An IgE signaling inhibitor can be a naturally occurring protein or a fragment thereof, e.g. a decoy protein. Such agents can be obtained from a natural source, e.g., a cell or tissue lysate. The agents can also be peptides, e.g., peptides of from about 5 to about 30 amino acids, with from about 5 to about 20 amino acids being preferred and from about 7 to about 15 being particularly preferred. The peptides can be digests of naturally occurring proteins, random peptides, "biased" random peptides, decoy proteins, dominant negative proteins, etc. In some methods, the agents are polypeptides or proteins.

An IgE signaling inhibitor can function directly in the form in which it is administered. Alternatively, the agent can be modified or utilized intracellularly to produce something which is an inhibitor of IgE signaling as described herein, e.g. introduction of a nucleic acid sequence into the cell and its transcription resulting in the production of an inhibitor of IgE gene expression or protein activity.

Agents can be produced recombinantly using methods well known to those of skill in the art (see Sambrook et al., Molecular Cloning: A Laboratory Manual (3 ed.), Cold Spring Harbor Laboratory Press, Cold Spring Harbor, N.Y., USA (2001)).

IgE signaling inhibitors can be synthesized and/or isolated according to methods well known in the art and are available commercially, e.g. omalizumab (available as XOLAIR™ from Genentech, San Francisco, Calif.).

In some embodiments, the methods described herein relate to treating a subject having or diagnosed as having a cardiovascular or metabolic disease as described herein, e.g. atheroscleoris. Subjects having a cardiovascular or metabolic disease as described herein can be identified by a physician using current methods of diagnosing such conditions. By way of non-limiting example, symptoms and/or complications of atheroscleorsis which characterize these conditions and aid in diagnosis are well known in the art and include but are not limited to, bruit and weak or absent pulses. Tests that may aid in a diagnosis of, e.g. atherosclerosis include, but are not limited to, blood tests, EKG, chest x-ray, echocardiograms, CT scan, stress test, and angiography. A family history of coronary artery disease, or exposure to risk factors for atherosclerosis (e.g. smoking) can also aid in determining if a subject is likely to have atherosclerosis or in making a diagnosis of atherosclerosis.

The compositions and methods described herein can be administered to a subject having or diagnosed as having a cardiovascular or metabolic disease as described herein. In some embodiments, the methods described herein comprise administering an effective amount of compositions described herein, e.g. an IgE signaling inhibitor to a subject in order to alleviate a symptom of a cardiovascular or metabolic disease as described herein. As used herein, "alleviating a symptom of" is ameliorating any condition or symptom associated with the condition. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, or by injection. Administration can be local or systemic.

In some embodiments, the methods and uses described herein relate to administering a therapeutically effective amount of an IgE signaling inhibitor to a subject. The term "effective amount" as used herein refers to the amount of an IgE signaling inhibitor needed to alleviate at least one or more symptom of the disease or disorder, and relates to a sufficient amount of pharmacological composition to provide the desired effect. The term "therapeutically effective amount" therefore refers to an amount of an IgE signaling inhibitor that is sufficient to effect a particular effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of an IgE signaling inhibitor, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for an IgE signaling inhibitor, among others. The dosage can be determined by a physician and adjusted, as necessary, to suit observed effects of the treatment.

In some embodiments, the technology described herein relates to a pharmaceutical composition comprising an IgE signaling inhibitor as described herein, and optionally a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. an IgE signaling inhibitor as described herein.

In some embodiments, the pharmaceutical composition comprising an IgE signaling inhibitor as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, administration DUROS®-type dosage forms, and dose-dumping.

Suitable vehicles that can be used to provide parenteral dosage forms of an IgE signaling inhibitor as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of an IgE signaling inhibitor as disclosed herein can also be incorporated into the parenteral dosage forms of the disclosure, including conventional and controlled-release parenteral dosage forms.

Pharmaceutical compositions comprising an IgE signaling inhibitor can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the IgE signaling inhibitor can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

The methods described herein can further comprise administering a second agent and/or treatment to the subject, e.g. as part of a combinatorial therapy. Agents for the treatment of cardiovascular and metabolic disease are well known in the art, (see e.g. "Physicians Desk Reference" $24^{th}$ Ed. Thomson PDR: 2003 and Sweetman, Sean C. (Ed) "Martindale: The Complete Drug Reference" $37^{th}$ Ed. Pharmaceutical Press: 2011). For example, a second agent and/or treatment for atherosclerosis can include, but is not limited to cholesterol medications (e.g. statins, fibrates, nictotinic acid, and cholestyramine); anti-platelet medications (e.g. aspririn; adenosine diphosphate receptor inhibitors, phosphodiesterase inhibitors, glycoprotein IIB/IIIA inhibitors, adenosine reuptake inhibitors; thromboxane inhibitors); beta blockers (e.g. alprenolol; bucindolol; carteolol; carvedilol; labetalol; nadolol; oxprenolol; penbutolol; pindolol; propranolol; sotalol; timolol; acebutolol; atenolol; betaxolol; bisoprolol; celiprolol; esmolol; metoprolol; and nebivolol); angiotensin-converting enzyme (ACE) inhibitors (e.g. captopril; zofenopril; enalapril; ramipril; quinapril; perindopril; lisinopril; benazepril; imidapril; trandolapril; and fosinopril) and calcium channel blockers (e.g. verapamil; amlodipine; aranidipine; azelnidipine; barnidipine; benidipine; clinidipine; clevidipine; isradipine; efonidipine; felodipine; lacidipine; lercandipine; manidipine; nicardipine; nifedpine; nilvadipine; nimodipine; nisoldipine; nitrendipine; pranidipine; and diltiazem)

In certain embodiments, an effective dose of a composition comprising an IgE signaling inhibitor as described herein can be administered to a patient once. In certain embodiments, an effective dose of a composition comprising an IgE signaling inhibitor can be administered to a patient repeatedly. For systemic administration, subjects can be administered a therapeutic amount of a composition comprising an IgE signaling inhibitor, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more. A composition comprising an IgE signaling inhibitor can be administered over a period of time, such as over a 5 minute, 10 minute, 15 minute, 20 minute, or 25 minute period. The administration can be repeated, for example, on a regular basis, such as hourly for 3 hours, 6 hours, 12 hours or longer or such as biweekly (i.e., every two weeks) for one month, two months, three months, four months or longer.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to an IgE signaling inhibitor. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more.

The dosage ranges for the administration of an IgE signaling inhibitor, according to the methods described herein depend upon, for example, the form of an IgE signaling inhibitor, its potency, and the extent to which symptoms, markers, or indicators of a condition described herein are desired to be reduced, for example the percentage reduction desired for plaque instability or the extent to which, for example, changes in blood glucose levels are desired to be induced. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of an IgE signaling inhibitor in, e.g. the treatment of a condition described herein, can be determined by the skilled clinician. However, a treatment is considered "effective treatment," as the term is used herein, if any one or all of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. plaque levels, plaque instability, or blood glucose levels. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. inflammation); or (2) relieving the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. blood pressure, plaque levels, or blood glucose). It is well within the ability of one skilled in the art to monitor efficacy of administration and/or treatment by measuring any one of such parameters, or any combination of parameters. Efficacy can be assessed in animal models of a condition described herein, for example treatment of atherosclerosis. When using an experimental animal model, efficacy of treatment is evidenced when a statistically significant change in a marker is observed, e.g. lesion characteristics as described herein.

In vitro and animal model assays are provided herein which allow the assessment of a given dose of an IgE signaling inhibitor. By way of non-limiting example, the effects of a dose of an IgE signaling inhibitor can be assessed by determining the level of IgE-induced cell death in cell culture. A non-limiting example of a protocol for such an assay is as follows: human or mouse macrophages or HuSMC can be cultured on 8-well chamber slides, 96-well plates, or 6-well plate pre-coated with 1% gelatin. After overnight starvation, cells can be stimulated with IgE (50 µg/mL for macrophages and 100 µg/mL for HuSMC) for 3~4 days before detecting apoptotic cells using TUNEL staining (IN SITU CELL DEATH DETECTION KIT™, Roche Diagnostics Corp., Indianapolis, Ind.), MTT cell proliferation assay (Millipore), or CyQUANT™ cell proliferation assay (Invitrogen, Carlsbad, Calif.).

The efficacy of a given dosage combination can also be assessed in an animal model, e.g. a mouse model of atherosclerosis as described in the Examples herein. For example, 10-week-old males can be fed a Western diet (Research Diets, Inc., New Brunswick, N.J.) for 12 weeks. The development of atherosclerosis, and efficacy for treatments thereof, can be determined by lesion characterizations, including thoracic-abdominal aorta oil-red O staining, aortic arch lesion intima and media areas, immunocytological or immunohistochemical examination of lesion macrophages (Mac-3), T cells (CD4 and CD3), IL6 (Abcam), MHC class-II-positive cells, and TUNEL-positive apoptotic cells (ApopTag® Plus Peroxidase In Situ Apoptosis Kit; Millipore).

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. The use of an IgE signaling inhibitor to treat a subject in need of treatment for a condition selected from the group consisting of:
    atherosclerosis; aneurysm; aortic aneurysm; abdominal aoritic aneurysm; diabetes; and obesity.
2. The use of paragraph 1, wherein the IgE signaling inhibitor is an IgE inhibitor.
3. The use of paragraph 2, wherein the IgE inhibitor is selected from the group consisting of;
    an anti-IgE monoclonal antibody; omalizumab; and talizumab.
4. The use of paragraph 1, wherein the IgE signaling inhibitor is an IgE receptor inhibitor.
5. A method comprising, administering a therapeutically effective amount of an IgE signaling inhibitor to a subject in need of a treatment for atherosclerosis.
6. A method comprising, administering a therapeutically effective amount of an IgE signaling inhibitor to a subject in need of a treatment for aneurysm.
7. The method of paragraph 6, wherein the aneurysm is selected from the group consisting of:
    aortic aneurysm and abdominal aortic aneurysm.
8. A method comprising, administering a therapeutically effective amount of an IgE signaling inhibitor to a subject in need of a treatment for diabetes.

9. A method comprising, administering a therapeutically effective amount of an IgE signaling inhibitor to a subject in need of a treatment for obesity.
10. The method of any of paragraphs 5-9, wherein the IgE signaling inhibitor is an IgE inhibitor.
11. The method of paragraph 10, wherein the IgE inhibitor is selected from the group consisting of;
    an anti-IgE monoclonal antibody; omalizumab; and talizumab.
12. The method of any of paragraphs 5-9, wherein the IgE signaling inhibitor is an IgE receptor inhibitor.

EXAMPLES

Example 1

Immunoglobulin E (IgE) associates with allergic responses and participates in the activation of mast cells, a cell type implicated in atherogenesis. It is demonstrated herein that serum IgE levels are elevated in patients with myocardial infarction or unstable angina pectoris. IgE and its receptor subunit FcER1α are present in human atherosclerotic lesions, and they localize particularly to areas rich in macrophages. In mice, absence of FcER1α reduces inflammation and apoptosis in atherosclerotic plaques. In cultured macrophages, the presence of Toll-like receptor 4 (TLR4) is required for FcεR1 activity. IgE stimulates interaction between FcεR1 and TLR4, thereby inducing macrophage signal transduction, inflammatory molecule expression, and apoptosis. These IgE activities are reduced in the absence of FcεR1 or of TLR4 (but not of TLR2). Furthermore, IgE activates macrophages by enhancing their $Na^+/H^+$ exchanger NHE1 activity, thus reducing extracellular pH. Inactivation of NHE1 blocks IgE-induced macrophage inflammatory molecule production and apoptosis. Cultured human aortic smooth-muscle cells (SMCs) and endothelial cells (ECs) also exhibit IgE-induced signal transduction, cytokine expression, and apoptosis, and in human atherosclerotic lesions, SMCs and ECs colocalize with IgE and TUNEL staining. The data presented herein reveals several previously unrecognized IgE activities that affect arterial cell biology and likely other IgE-associated pathologies in human diseases.

Immunoglobulin E (IgE) is an important regulator of allergic reactions, in which it activates mast cells (MCs) by binding to its high-affinity receptor FcεR1 (1). In addition to allergic responses (2), MCs participate in other inflammatory diseases, including atherosclerosis (3, 4). IgE is the least abundant antibody isotype in humans, and its role in human immunology (other than its effects on allergy and parasitic infection) long has been unclear. In addition to MCs, dendritic cells, eosinophils, platelets, monocytes, and macrophages also bear FcεR1 on their surfaces (5-9), albeit in different assemblages. For example, FcεR1 on MCs is a heterotetramer ($\alpha\beta\gamma_2$), whereas FcεR1 on macrophages or eosinophils is a heterotrimer ($\alpha\gamma_2$) (7). In dendritic cells, the expression of FcεR1 affects IFN-γ-mediated pro-inflammatory (tumor necrosis factor-α [TNF-α]) and anti-inflammatory (IL-10) cytokine production (6), as well as the efficiency of antigen uptake and presentation (10). Therefore, IgE's targets likely extend beyond MCs.

Macrophages are an important cell type in atherosclerotic lesions, the formation of macrophage foam cells being the hallmark of atherogenesis. Uptake of oxidized low-density lipoprotein (ox-LDL) particles by macrophages, mediated primarily by cell-surface scavenger receptors (SRs), is an important pathway of foam cell formation. Interruption of this pathway in cell culture and in animal models blocks foam cell formation, thereby reducing atherogenesis (11, 12). But alternative pathways of lipid uptake have also been proposed. Atherosclerosis-prone apolipoprotein E-deficient ($Apoe^{-/-}$) mice missing either CD36 or scavenger receptor-A develop abundant macrophage foam cells in aortic sinus lesions (13). Indeed, macrophage SRs also play atheroprotective roles in both early and late phases of atherogenesis. Expression of decoy SRs retards early atherosclerotic lesion formation in experimental models (14). In advanced lesions, SR-associated signaling contributes to macrophage death and necrotic core formation (15), but this proatherogenic role of SRs is balanced by their ability to recognize and clear apoptotic cells in a nonphlogistic manner. Ox-LDL also has many signaling functions on macrophages, which are mediated by TLRs—mainly by TLR2 and TLR4. Atherosclerosis-prone apolipoprotein E-deficient ($Apoe^{-/-}$) mice or low-density lipoprotein receptor knockout ($Ldlr^{-/-}$) mice lacking TLR2 or TLR4 demonstrate an impaired inflammatory response to hyperlipidemia, and thus are resistant to atherosclerosis (16, 17).

It is demonstrated herein that circulating IgE levels in patients with atherosclerosis associate with plaque instability. Furthermore, it was found that IgE is present in atherosclerotic plaques and co-localizes with lesion macrophages, SMCs, and ECs. It is further demonstrated herein that IgE activates $Na^+/H^+$ exchanger NHE1, which is followed by lowering of extracellular pH, thereby promoting macrophage and vascular cell inflammation and apoptosis. IgE activities require cooperative interaction between FcεR1 and TLR4—two receptors present on several cell types relevant to the development of atherosclerosis.

Results

Enhanced Serum IgE Levels in Patients with Unstable Plaques.

It is demonstrated herein that human serum IgE levels correlated with the degree of coronary heart disease (CHD) in two Chinese populations. Serum IgE levels were significantly higher in 709 patients with CHD than in 273 subjects without CHD (90.61±2.91 vs. 57.13±5.35 IU/mL, P<0.001) from Central China (Table 1). After classifying CHD patients into acute myocardial infarction (AMI), unstable angina pectoris (UAP), and stable angina pectoris (SAP) groups, it was found that AMI patients (n=207, 126.08±6.37 IU/mL) had the highest serum IgE levels, followed by UAP patients (n=255, 89.60±4.89 IU/mL) and SAP patients (n=247, 61.91±2.93 IU/mL) (Table 2). Pearson's correlation test and independent sample t test suggested that serum IgE correlated with smoking status (P=0.049), but not with age, sex, body-mass index, hypertension, diabetes mellitus, or serum lipid profiles (Table 3). Significantly increased serum IgE levels in patients with unstable atherosclerosis supported the hypothesis that IgE participates in human atherogenesis. To replicate these observations, an independent group of subjects with CHD (n=147) and without CHD (n=93) were obtained from Eastern China, and results similar to those in the patient groups from Central China were found (Tables 4 and 5). Serum IgE levels were significantly higher in CHD patients than in those without CHD (99.55±9.84 vs. 62.21±5.69 IU/mL, P=0.001). Pearson's correlation test and independent sample t test suggested that serum IgE correlated with fasting glucose (P=0.001), but not with smoking or other variables (Table 6). AMI patients (n=33, 133.63±26.28 IU/mL) had the highest serum IgE levels, followed by UAP patients (n=83, 97.72±12.41 IU/mL) and SAP patients (n=31, 68.18±15.76 IU/mL) (Table 5).

Increased Local IgE and FcεR1 Levels in Human Atherosclerotic Plaques.

Figure 1A:
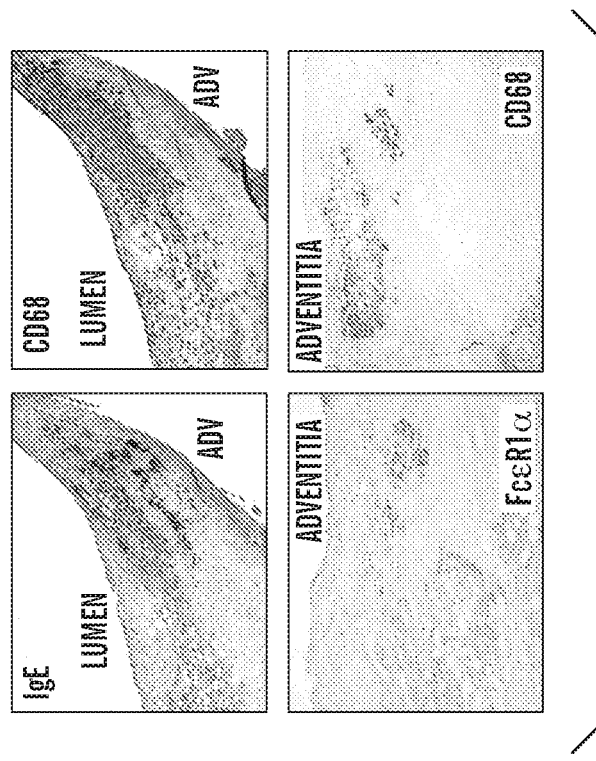
Figure 1D:
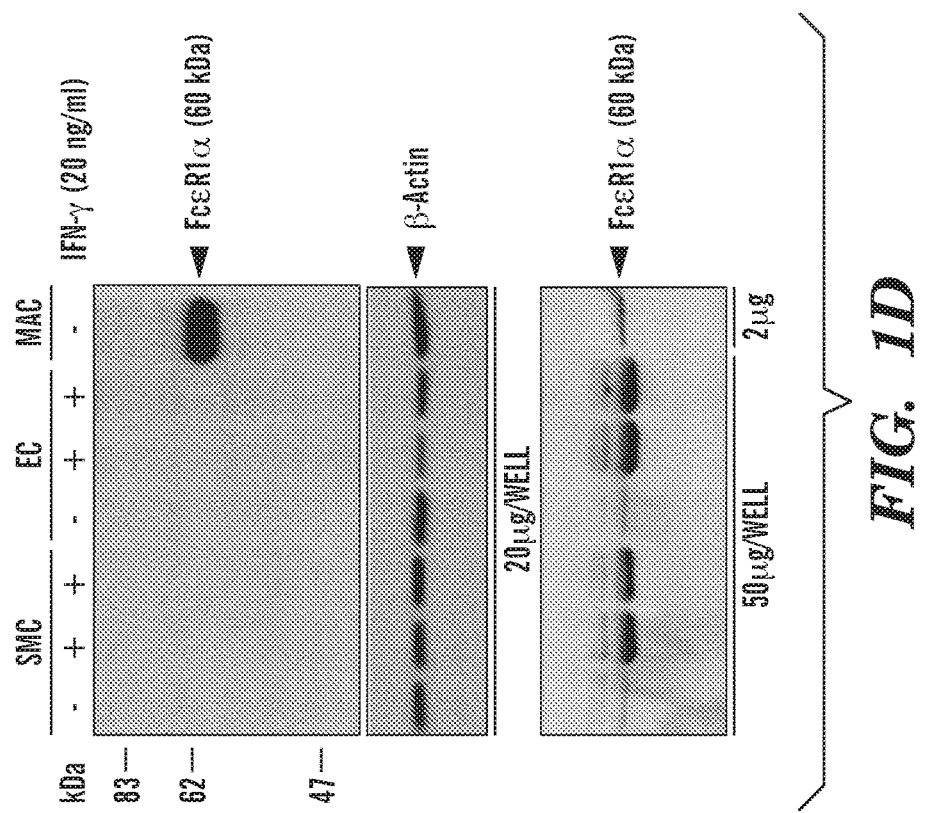
Figure 1C:
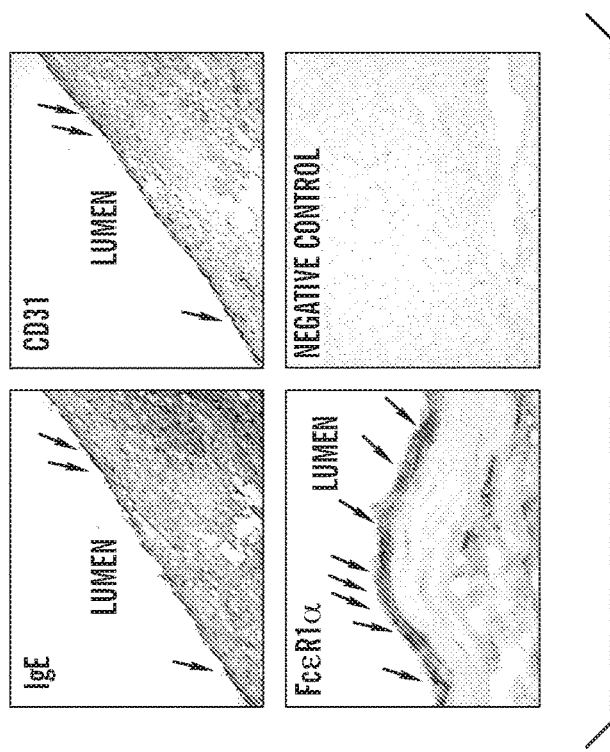

To examine further IgE involvement in atherosclerosis, parallel frozen sections of human atherosclerotic lesions were immunostained for IgE, its high-affinity receptor FcεR1α (1), and cell type-specific antibodies for macrophages (CD68), SMCs (α-actin), and ECs (CD31) (18). Enhanced atherosclerotic lesion IgE and FcεR1α immunoreactivities localized to CD68$^+$ macrophage-rich shoulder and adventitia regions, α-actin-positive SMC-rich fibrous caps, and CD31$^+$ ECs in the luminal surface (FIGS. 1A-1C), all of which outnumbered MCs in human and mouse atherosclerotic lesions (4, 19). Using immunoblot analysis, FcεR1α expression was confirmed in these cells. When 20 μg of cell lysates were used, FcεR1α expression was clearly visible in human monocyte-derived macrophages, but hardly visible in human aortic SMCs or ECs (FIG. 1D, top panel). Overexposure of the immunoblot film revealed expression of FcεR1α in SMCs and ECs after stimulation with the inflammatory cytokine IFN-γ, which operates in human atherosclerotic lesions (20) (data not shown). To enhance the FcεR1α signals from SMCs and ECs, 50 μg cell lysates from these cells were used, while 2 μg cell lysates from macrophages were sufficient. Under these loading conditions (FIG. 1D, bottom panel), increased FcεR1α expression was detected in IFN-□-treated SMCs (lanes 2 and 3) and ECs (lanes 5 and 6). Together, these data demonstrated that the expression of FcεR1α is high and constitutive in cultured macrophages, and it is low and inducible in cultured arterial SMCs and ECs. These results in cultured cells agree with those from immunohistochemistry analysis (FIG. 1A-1C). The majority of macrophage-rich areas contained FaR1α, whereas only a small portion of SMC-rich areas and ECs in the lumen contained IgE and FaR1α.

Reduced Atherosclerosis in FcεR1α-Deficient Mice.

As in CHD patients, serum IgE levels increased significantly in Apoe$^{-/-}$ mice after consuming a high-fat diet (Western diet) (FIG. 2A). To test a direct role of IgE in atherogenesis, FaR1α-deficient mice (Fcer1a$^{-/-}$) (21) were crossed with atherosclerosis-prone apolipoprotein E-deficient (Apoe$^{-/-}$) mice. After 12 weeks on a Western diet, Apoe$^{-/-}$ mice that were wild-type for FcεR1α (Apoe$^{-/-}$Fcer1a$^{+/+}$) developed atherosclerosis. The absence of FcεR1α (Apoe$^{-/-}$Fcer1a$^{-/-}$) significantly reduced aortic lipid deposition and aortic arch intima areas (FIGS. 2B and 2C), although media areas were not affected (FIG. 2D). Atherosclerotic lesion characterizations demonstrated that lesion contents of macrophages, T cells, and inflammatory cytokine interleukin-6 (IL6), as well as major histocompatibility class-II molecule levels (FIG. 2E), were significantly reduced in Apoe$^{-/-}$Fcer1a$^{-/-}$ mice, suggesting attenuated inflammation in the absence of FcεR1α. In addition to reduced inflammation, Apoe$^{-/-}$Fcer1a$^{-/-}$ mice showed significantly less apoptosis of lesional cells (FIG. 2G). In early lesions, macrophage apoptosis limits lesion cellularity and suppresses lesion progression. In advanced lesions, however, macrophage apoptosis promotes the development of the necrotic core a key factor of plaque vulnerability and acute luminal thrombosis and associates with plaque necrosis (22). Number of necrotic cores (FIG. 2G) as well as necrotic core areas from both aortic arches (0.016±0.005 mm$^2$ vs. 0.065±0.016 mm$^2$, P=0.021) and brachiocephalic arteries (0.025±0.004 mm$^2$ vs. 0.071±0.019 mm$^2$, P=0.044) were significantly smaller in Apoe$^{-/-}$Fcer1a$^{-/-}$ mice than in Apoe$^{-/-}$Fcer1a$^{+/+}$ mice.

Figure 8:
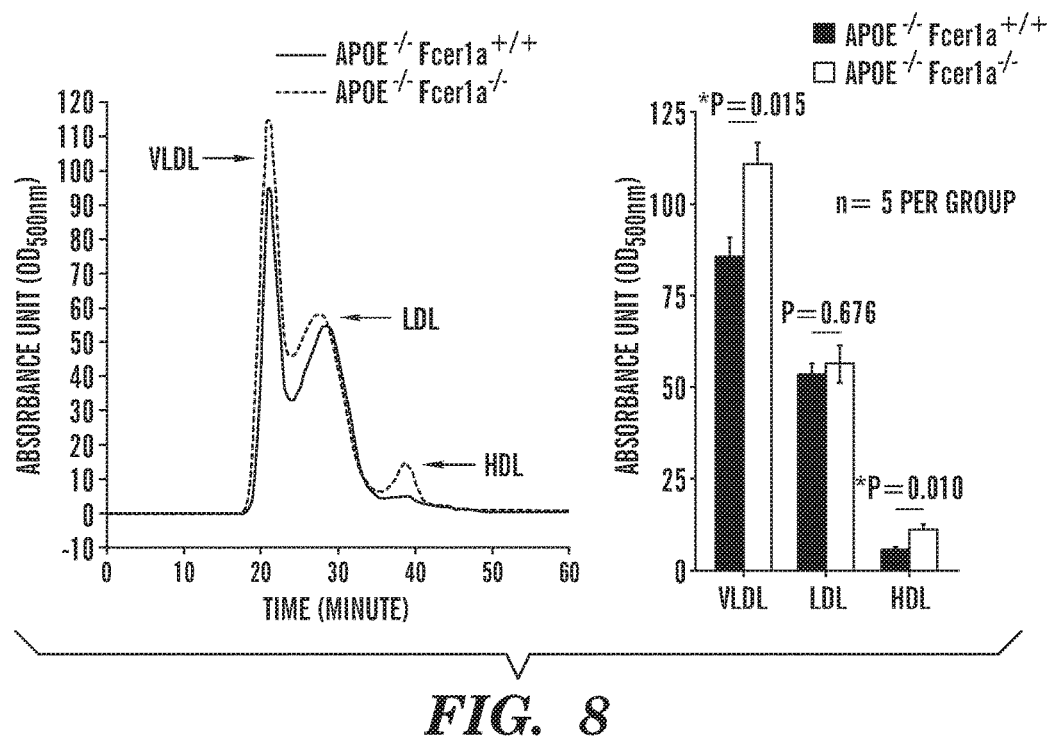
FIG. 8 depicts FPLC analysis of serum samples from $Apoe^{-/-}Fcer1a^{+/+}$ mice and $Apoe^{-/-}Fcer1a^{-/-}$ mice after 12 weeks on a Western diet. $P<0.05$ was considered statistically significant, Mann-Whitney U test. Representative data are shown to the left.

Reduced atherosclerosis in Apoe$^{-/-}$Fcer1a$^{-/-}$ mice did not affect serum total cholesterol or LDL levels, but increased serum triglyceride and high-density lipoprotein (HDL) levels (Table 7). Although triglyceride levels did not reach statistical significance (P=0.08), HDL levels were significantly higher in Apoe$^{-/-}$Fcer1a$^{-/-}$ mice than in Apoe$^{-/-}$ Fcer1a$^{-/-}$ mice (P=0.019). Serum fast performance liquid chromatography (FPLC) analysis from 5 Apoe$^{-/-}$Fcer1a$^{+/+}$ mice and 5 Apoe$^{-/-}$ Fcer1a$^{-/-}$ mice demonstrated similar lipid profiles. Both very low-density lipoprotein (VLDL) (P=0.015) and HDL (P=0.01) absorbance units were significantly higher in serum from Apoe$^{-/-}$ Fcer1a$^{-/-}$ mice than in serum from Apoe$^{-/-}$ Fcer1a$^{+/+}$mice, but LDL absorbance units from the two groups of mice were comparable (FIG. 8).

IgE Activities Require Interactions of FcεR1 and TLR4.

Figure 3C:
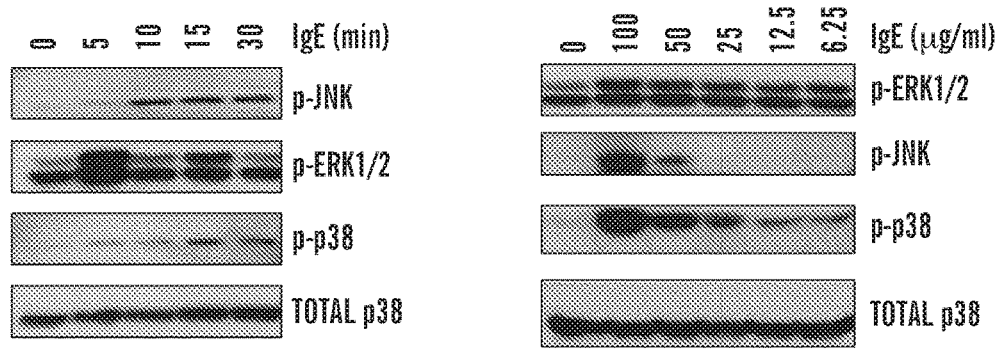
Figure 3C:
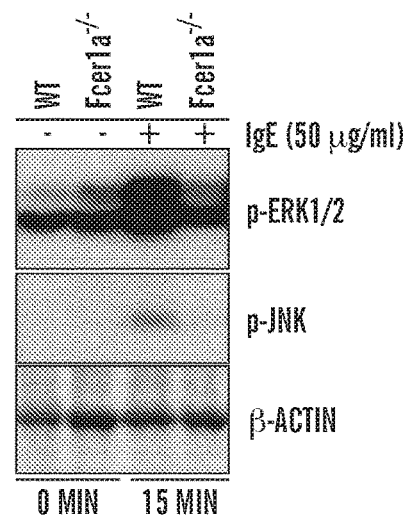
Figure 3F:
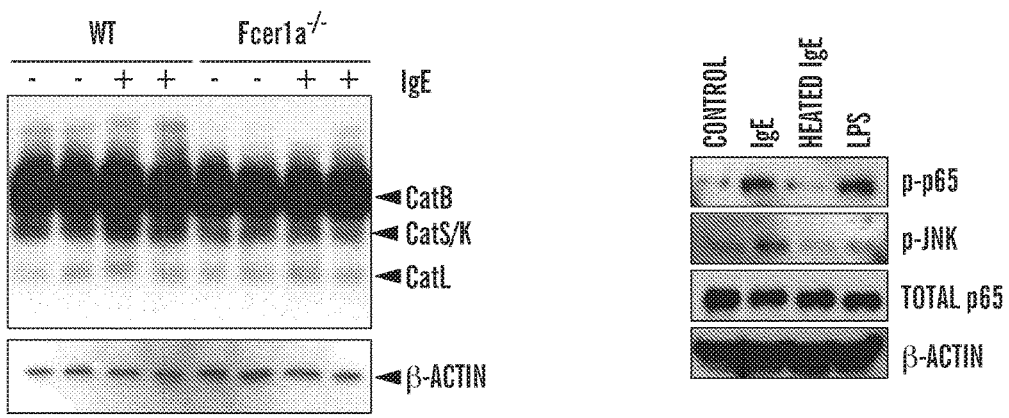
Figure 3F:
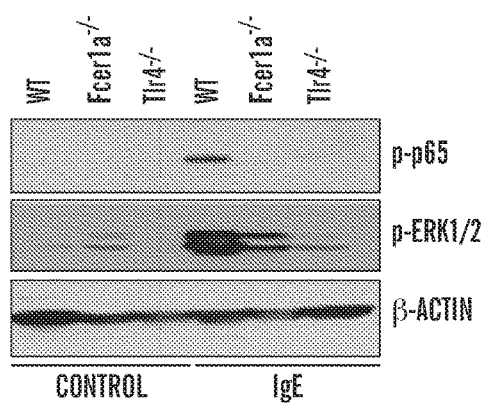
Figure 3G:
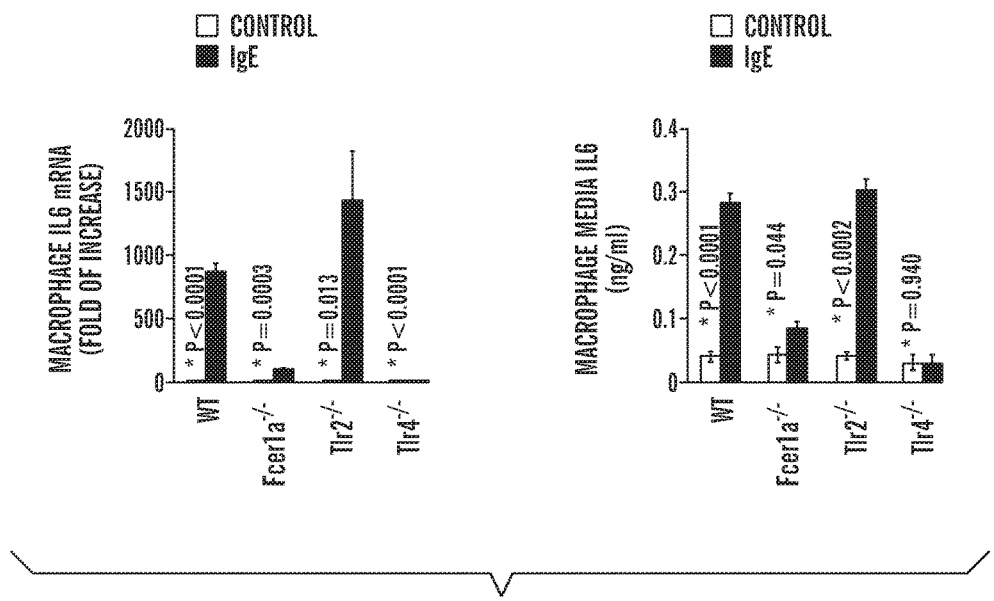
Figure 3H:
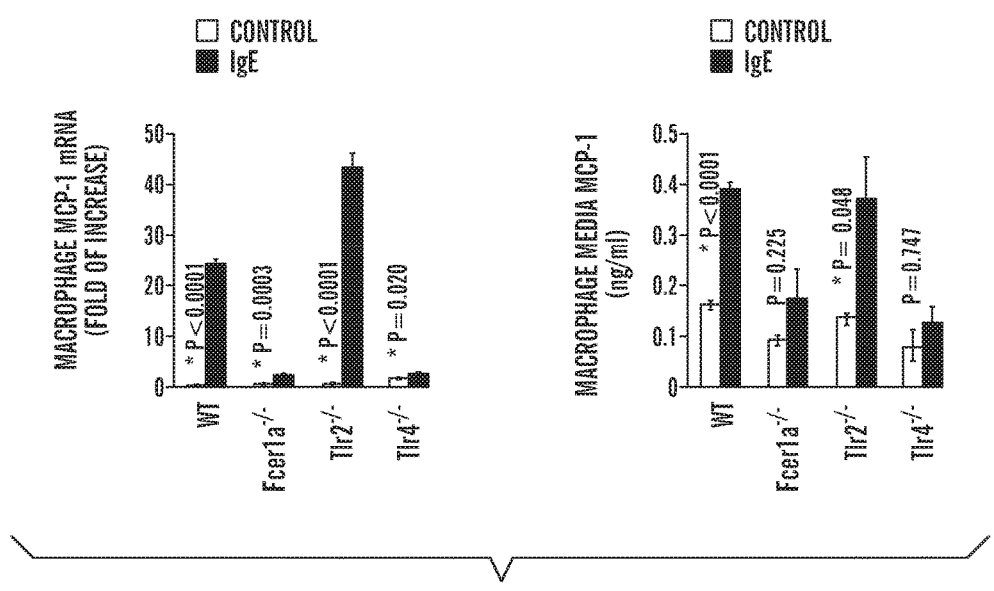

Abundant FcεR1α expression in macrophages (FIGS. 1A and 1D) suggests that IgE function in atherosclerosis reaches beyond MC activation. Exposure to purified IgE from mouse hybridoma (SPE-7) (23) elicited dose-dependent and time-dependent cell signaling molecule activation in mouse peritoneal macrophages—including the stress and inflammation signals Jun amino-terminal kinase (JNK) and mitogen-activated protein kinase (MAPK) (p38), and cell proliferation signal extracellular signal-regulated kinase (ERK) (FIGS. 3A and 3B). After 15 minutes of 50 μg/mL IgE treatment, macrophages from wild-type (WT) mice, but not those from Fcer1a$^{-/-}$ mice, showed increased phosphorylation of ERK1/2 and JNK (FIG. 3C), suggesting that IgE stimulates macrophage signal transduction via FcεR1. When macrophages from WT mice were stimulated with IgE for 2 days, activities of the proatherogenic cysteine proteases cathepsin S and cathepsin K (18, 24) increased, as detected by cysteinyl cathepsin active site labeling (18), an action of IgE not displayed by macrophages from Fcer1a$^{-/-}$ mice (FIG. 3D). To test whether IgE-mediated macrophage signaling and protease production were due to contamination of lipopolysaccharide (LPS), which remains active after boiling for 30 minutes (25), mouse IgE was heat-inactivated for 5 minutes at boiling, and it was found that heated IgE did not stimulate phosphorylation of JNK or p65 NF-κB, arguing against the possibility that LPS contamination accounted for the effects attributed to mouse IgE. As a positive control, LPS alone activated macrophage p65 NF-κB, likely via Toll-like receptor 4 (TLR4) (FIG. 3E) (26). No LPS contamination was detected (undetectable level) in the hybridoma-derived mouse IgE using the ToxinSensor™ Chromogenic LAL Endotoxin Assay Kit. To evaluate further the possibility of LPS contamination accounting for the effects of mouse hybridoma-derived IgE, macrophages from WT mice, Fcer1a$^{-/-}$ mice, and Tlr4$^{-/-}$ mice with IgE were stimulated and, surprisingly, IgE had a negligible effect on p65 and ERK phosphorylation in macrophages from both Fcer1a$^{-/-}$ mice and Tlr4$^{-/-}$ mice (FIG. 3F). Consistent with these findings, IgE induced both the mRNA (real-time PCR) and media protein levels (ELISA) of IL6 and of the chemokine monocyte chemotactic protein-1 (MCP-1) in 2 days, and apoptosis (in situ immunofluorescent TUNEL staining) in 3 days, in macrophages from WT mice and Tlr2$^{4-/-}$ mice—but the same cells from Fcer1a$^{-/-}$ mice and Tlr4$^{-/-}$ mice failed to respond to IgE (FIG. 3G-3I). If IgE did not contain LPS (FIG. 3E), loss of IgE-induced cell signaling, cytokine and chemokine expression, and apoptosis in Tlr4$^{-/-}$ and Fcer1a$^{-/-}$ macrophages suggested that IgE function requires both TLR4 and FcεR1. Thus, cell lysates were prepared from WT macrophages that were pre-treated with or without 50 μg/mL IgE for 15 minutes, and then co-immunoprecipitation was performed with anti-FcεR1α or TLR4 antibodies, followed by immunoblot analysis with antibodies to detect TLR4 or FcεR1α. IgE treatment did not increase total cellular TLR4, FcεR1α, or β-actin protein levels (FIG. 3J), but formed a complex between TLR4 and FcεR1α as confirmed by the co-immunoprecipitation for FcεR1α and then immunoblot for TLR4, or co-immunoprecipitation for TLR4 and immunoblot for FcεR1α (FIG. 3K). The same co-immunoprecipitation antibodies were used for immunoblot analysis to confirm equal antibody precipitation between the samples. Therefore, FcεR1α and TLR4 co-immunoprecipitated after IgE stimulation, which explains the observation that deficiency of FcεR1α or TLR4 inhibited IgE-mediated macrophage signaling, inflammatory molecule expression, and apoptosis (FIG. 3F-3I). The role of TLR4 in macrophage apoptosis in atherosclerotic lesions has been demonstrated in several studies. This pattern recognition receptor mediates type A SR (SRA)-induced apoptosis in endoplasmic reticulum (ER)-stressed macrophages. Macrophages from Myd88$^{-/-}$ mice or lacking TLR4 are resistant to SRA ligand fucoidan- and UPR (unfold protein response) activator thapsigargin-induced apoptosis (27). TLR2/TLR4 deficiency in bone marrow-derived cells suppresses atherosclerotic lesion macrophage apoptosis and plaque necrosis in Ldlr$^{-/-}$ mice after 10 weeks of an atherogenic diet (28).

To examine whether IgE may use its low-affinity receptor FcεR2 (CD23) to mediate macrophage biology, peritoneal macrophages from Cd23$^{-/-}$ mice (29) were stimulated, and no significant differences in apoptosis and IL6 production were found from those from Cd23$^{+/+}$ littermates (C57BL/6 background) (data not shown), suggesting that FcεR1 is the dominant receptor for IgE.

IgE Regulates NHE1 Activities in Macrophages.

Figure 4D:
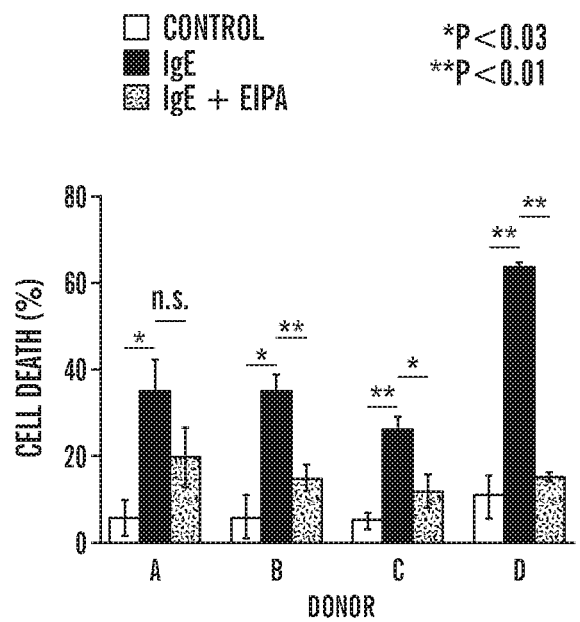
Figure 4E:
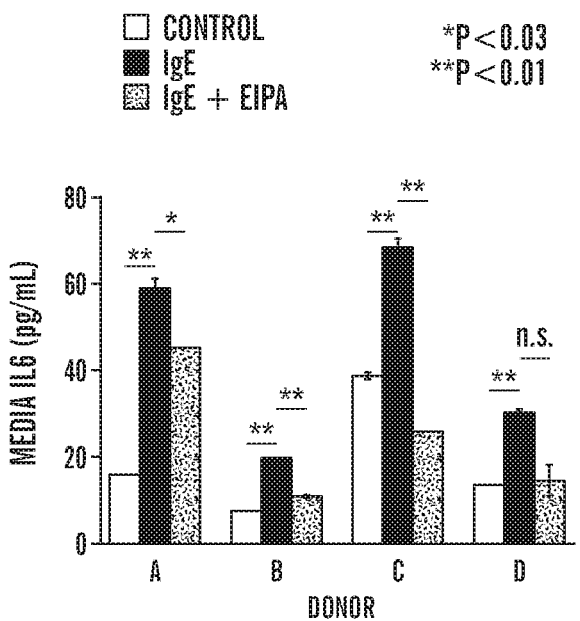
Figure 9:
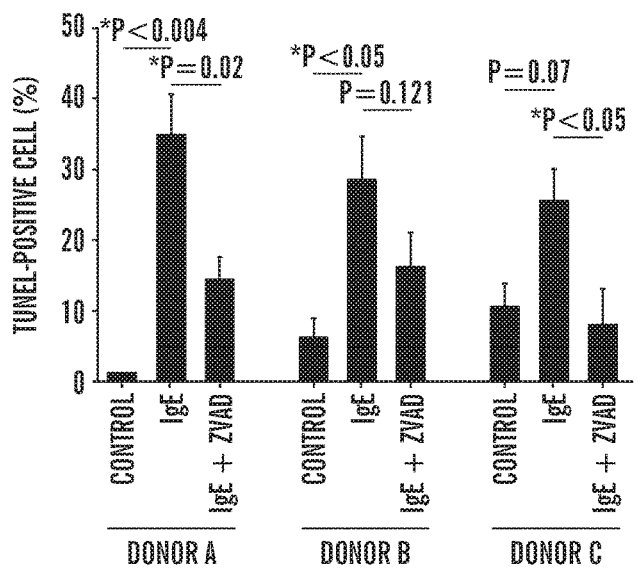
FIG. 9 depicts IgE induces human monocyte-derived macrophage apoptosis. Macrophages from three donors respond to IgE (SPE-7, 50 μg/mL) and undergo apoptosis. Caspase inhibitor ZVAD-FMK (20 μM) efficiently blocks IgE-induced macrophage apoptosis, although macrophages from different donors respond differently. *$P<0.05$ is considered statistically significant, non-parametric Mann-Whitney test.
Figure 10:
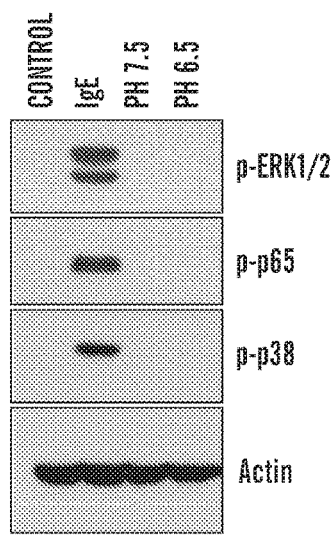
FIG. 10 depicts pH effects on macrophage signaling molecule activation. Culturing human macrophages in pH6.5 or pH7.5 media did not cause MAPK (ERK1/2 and p38) or MF-kB phosphorylation, as detected by immunoblot analysis. IgE (50 μg/mL) was used as a positive control, and actin blot was used as a protein loading control.

In human atherosclerotic lesions, areas with clusters of CD68$^+$ macrophages that also contained high amounts of IgE and FcεR1☐ were often highly positive for TUNEL staining (data not shown). In contrast, macrophage-rich regions that contained low levels of IgE and FcεR1☐ had only a few apoptotic cells (data not shown), suggesting a role of IgE in human macrophage apoptosis. As in mouse macrophages (FIG. 3I), immunoaffinity-purified human plasma IgE (50 µg/mL) (FIG. 4A) or mouse IgE (SPE-7, 50 µg/mL) (FIG. 9) induced human macrophage apoptosis, which could be blocked with a caspase inhibitor, ZVAD-FMK (20 µM), although there were some donor-to-donor variations among different human macrophage preparations. Surprisingly, IgE induced macrophage apoptosis by reducing extracellular pH with noticeable medium color change, and this activity depended on the Na$^+$/H$^+$ exchanger (NHE1) activity. NHE1 inhibition with 10 µM ethylisopropylamiloride (EIPA) completely blocked the IgE-induced medium color change and pH reduction (FIG. 4B), suggesting that reduced pH after IgE treatment was not caused by increased cell lysis or IgE contamination, but rather by enhanced NHE1 activity. EIPA treatment alone did not change pH (FIG. 4B) or cause cell death. When 100 ng/mL LPS induced human macrophage apoptosis by >50% in 2-3 days, 10 µM EIPA did not cause any cell death under the same condition (data not shown). Human macrophages underwent apoptosis within 3 days if they were cultured in acidic (pH 6.5) DMEM, but were resistant to apoptosis in neutral (pH 7.5) DMEM (FIG. 4C). The observations described herein agree with previous findings that advanced human and rabbit atherosclerotic lesions become acidic compared with healthy arterial intima (30), and that macrophages augment uptake of modified lipid and foam cell formation in an acidic environment (31), although a pH effect on macrophage apoptosis has not been noted. In contrast to macrophages in human atherosclerotic plaques exposed to IgE (data not shown) and acidic pH (30), cultured human macrophages undergo apoptosis at acidic pH, but pH changes (pH7.5 or pH6.5) without IgE did not affect MAPK (ERK1/2 and p38) or NF-κB (p65) phosphorylation (FIG. 10). When human macrophages underwent apoptosis and released IL6 to the media after IgE stimulation, EIPA significantly blocked cell death and IL6 secretion of macrophages from most donors (FIGS. 4D and 4E).

Figure 5A:
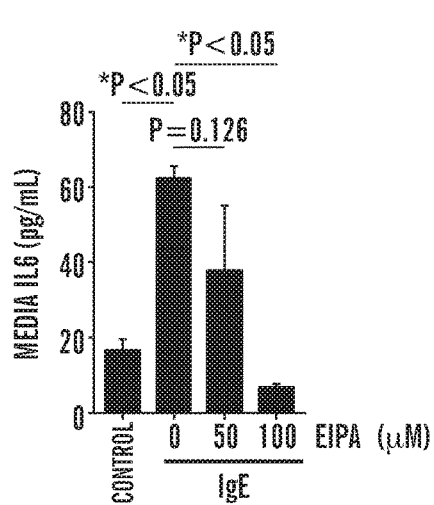
FIGS. 5A-5G depict NHE1 activity-dependent mouse peritoneal macrophage cytokine production and apoptosis.
Figure 5B:
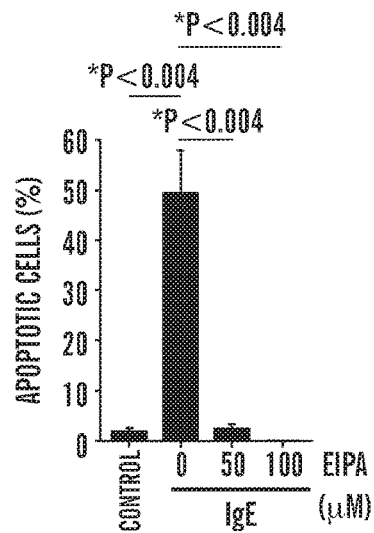
Figure 5C:
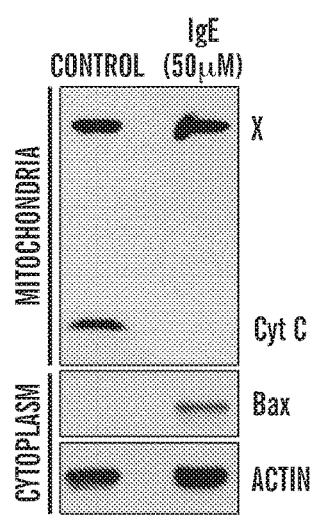
Figure 5D:
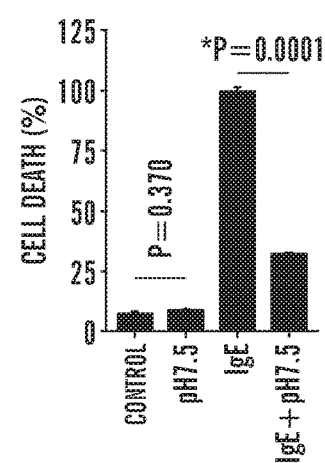
Figure 5E:
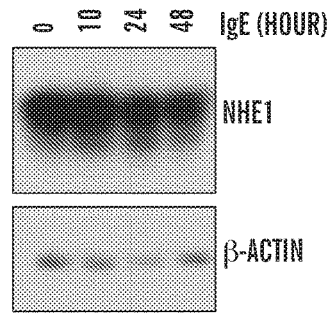
Figure 5F:
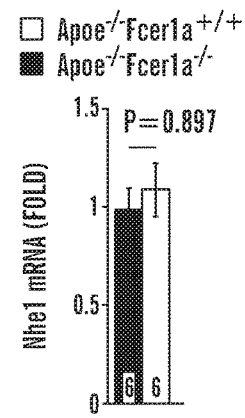
Figure 5G:
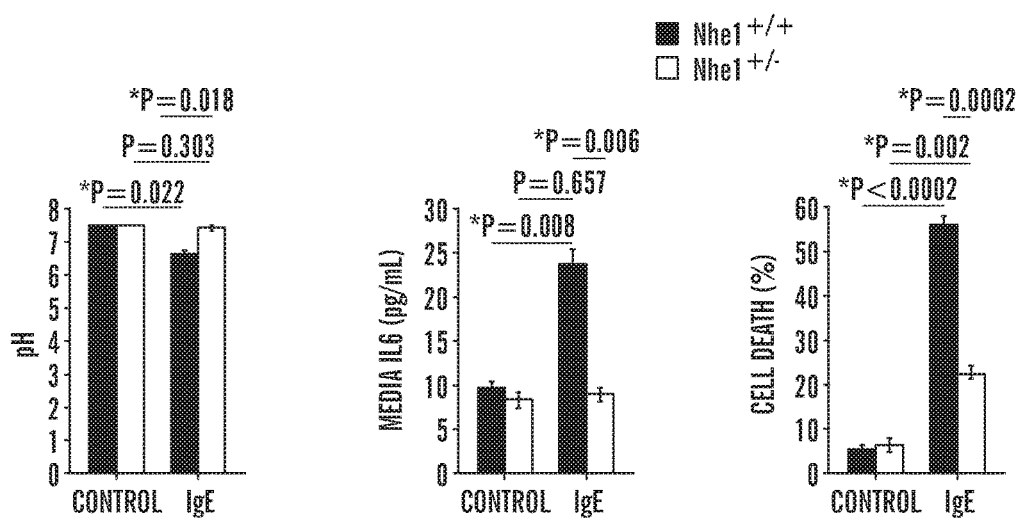

As the effects of IgE on IL6 production (FIG. 4E) or apoptosis (FIG. 4D and FIG. 8) in macrophages varied between donors, the IgE effects on macrophage pH changes and apoptosis were tested and affirmed in mouse peritoneal macrophages. As in human macrophages, IgE induced macrophage IL6 production (FIG. 5A) and apoptosis by activating NHE1 (FIG. 5B). Pharmacological inhibition of NHE-1 with 50-100 µM NHE-1 inhibitor EIPA blocked significantly IgE-induced macrophage secretion of IL6 or apoptosis. Mechanistically, IgE induced macrophage apoptosis by releasing cytochrome C from the mitochondria to the cytoplasm (32). Immunoblot analysis demonstrated the disappearance of cytochrome C in mitochondria preparation and enhanced cytoplasm Bax from IgE-stimulated macrophages (FIG. 5C). As in human macrophages, IgE-induced mouse macrophage death was also impaired significantly if cells were maintained under neutral (pH 7.5) condition (FIG. 5D). IgE activity-associated IL6 production (FIG. 5A) or apoptosis (FIG. 5B) of macrophages may affect NHE1 activity but not expression. Mouse macrophages showed no differences in NHE1 protein levels after IgE stimulation at different time points (FIG. 5E). Indeed, RT-PCR detected no aortic tissue NHE1 mRNA level changes in atherosclerotic lesions between Apoe$^{-/-}$Fcer1a$^{+/+}$ mice and Apoe$^{-/-}$Fcer1a$^{-/-}$ mice (FIG. 5F), but both IL6 (FIG. 2E) and apoptosis (FIG. 2F) differed significantly between the groups. To confirm further a role of NHE1 in IgE biology, peritoneal macrophages from Nhe1$^{+/-}$ mice (33) were stimulated and yielded results similar to those from EIPA-treated cells. Absence of one Nhe1 allele led to dramatic reduction in IL6 production and cell death, and did not change pH in IgE-treated macrophages (FIG. 5G).

Different Forms of IgE in Macrophage Activation.

Figure 6A:
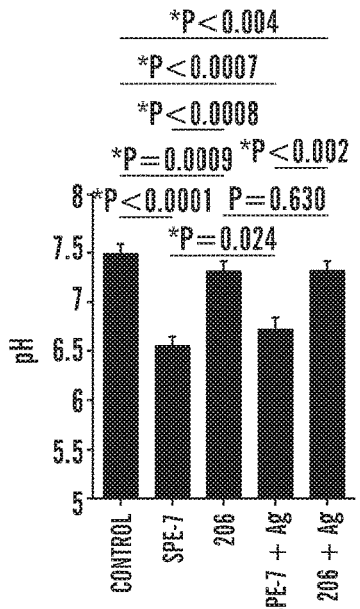
FIGS. 6A-6D demonstrate different IgE in macrophage activation. pH change (FIG. 6A), cell death (FIG. 6B), and IL6 production (FIG. 6C) in mouse macrophages treated with highly cytokinergic SPE-7 (50 μg/mL) or poorly cytokinergic H1 DNP-ε-206 (50 μg/mL) with or without antigen (10 ng/mL DNP-HSA).
Figure 6B:
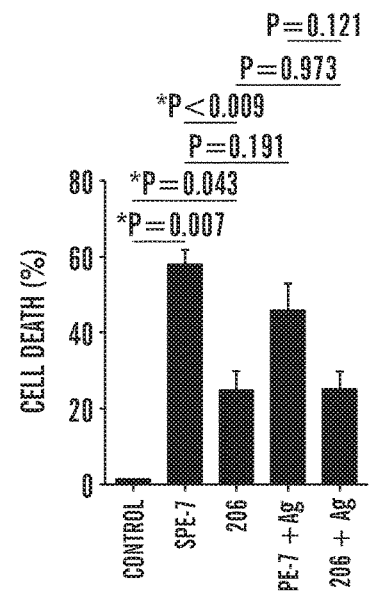
Figure 6C:
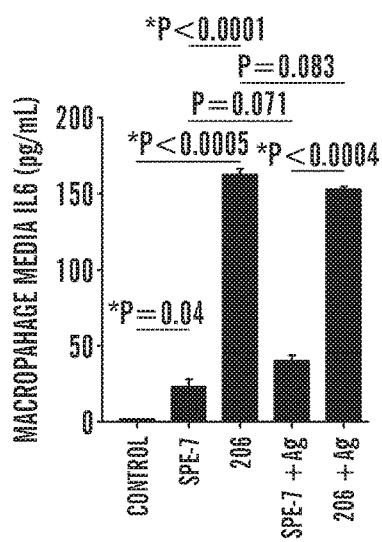

Aggregated forms of IgE are highly cytokinergic, while monomeric forms of IgE are poorly cytokinergic. The IgE used in the mouse macrophage study described herein was aggregated and cytokinergic (SPE-7)—usually more potent than monomeric, poorly cytokinergic IgE (e.g., H1 DNP-ε-206) in stimulating mast cells. While SPE-7 stimulates mast cell signal transduction, IL6 production, histamine release, or survival, H1 DNP-ε-206 appears to have much weaker activity or no activity (34). Antigens or anti-IgE antibodies often are needed to crosslink the IgE and thereby enhancing IgE activities (34, 35). Monomeric IgE H1 DNP-ε-206 may lose its ability to activate macrophages, and thus require IgE antigens. To test these possibilities, mouse macrophages were incubated with 50 µg/mL H1 DNP-ε-206 alone, or highly cytokinergic SPE-7 with and without 10 ng/mL antigen DNP-HSA (dinitrophenyl-human serum albumin). Both SPE-7 and H1 DNP-ε-206 significantly reduced pH (FIG. 6A) and promoted macrophage cell death, as determined by MTT assay (Millipore, FIG. 6B), but SPE-7 was much more potent than H1 DNP-ε-206. In contrast, H1 DNP-ε-206 more potently promoted macrophage IL6 release than SPE-7, as determined by ELISA (FIG. 6C). Lower IL6 production in SPE-7-treated macrophages than in those treated with H1 DNP-ε-206 may be due to more acidification and cell death in SPE-7-treated cells than in H1 DNP-ε-206-treated cells. DNP-HSA antigen showed no significant impact on SPE-7 or H1 DNP-ε-206 in any of these macrophage activity assays, suggesting that IgE activates macrophages independent of antibody cross-linking.

Figure 6D:
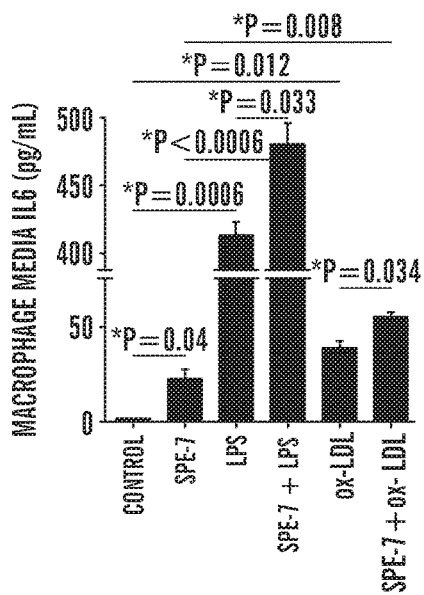

IgE induced a complex formation between FcεR1 and TLR4 (FIG. 3K), and absence of TLR and FcεR1a yielded the same defects of IgE-induced macrophage signaling transduction, chemokine/cytokine expression, and apoptosis (FIGS. 3F-3I). TLR4 ligand LPS demonstrated a synergistic effect with IgE on inducing mast cell IL6 production (36). Thus, IgE and LPS may have the same synergistic effect on macrophages. Ox-LDL-induced monocytic cell cytokine/chemokine expression and signal transduction are mediated partially by TLR4 (37). Ox-LDL induces coronary artery endothelial cell expression of atherosclerotic vascular calcification molecule bone morphogenetic protein-2 (BMP-2) via TLR4 (38). These observations suggest a synergistic effect of ox-LDL and IgE in macrophages. This hypothesis was tested by stimulating mouse peritoneal macrophages with 50 µg/mL SPE-7 with or without 100 ng/mL LPS or 50 µg/mL ox-LDL. Data presented in FIG. 6D indicate that SPE-7 increased further LPS-induced or ox-LDL-induced IL6 production.

Role of IgE in Vascular Cell Biology.

Figure 7A:
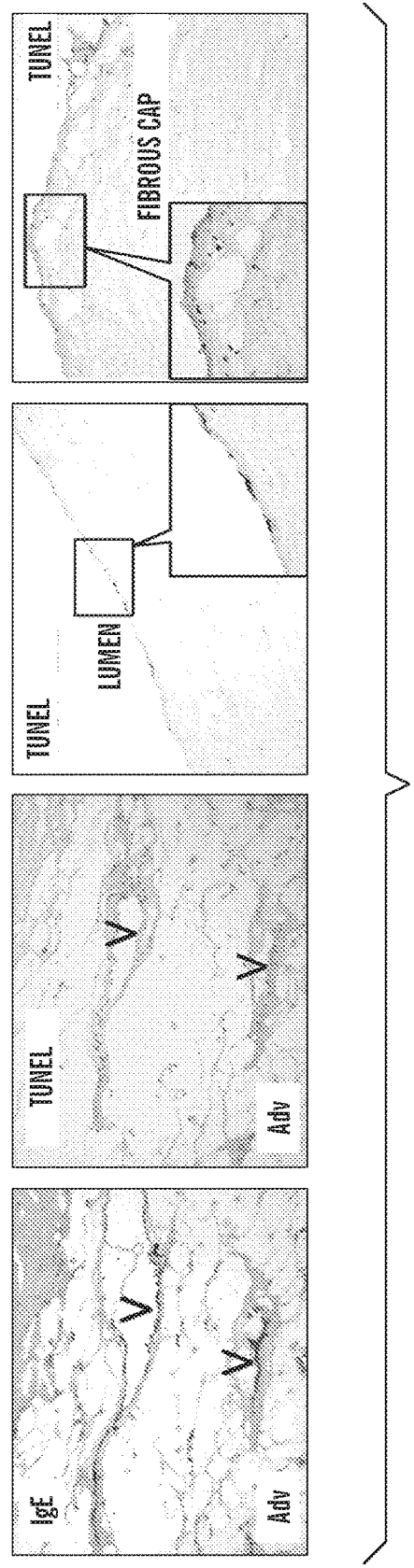
FIGS. 7A-7L demonstrate IgE effects on HuECs and HuSMCs.
Figure 7B:
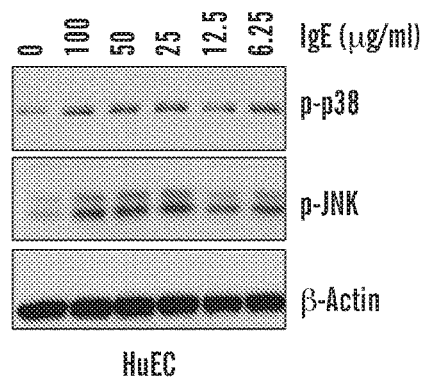
Figure 7C:
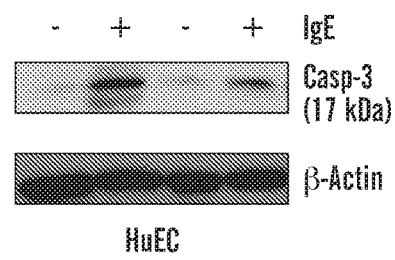
Figure 7D:
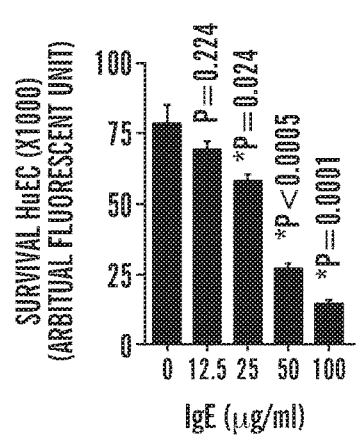
Figure 7E:
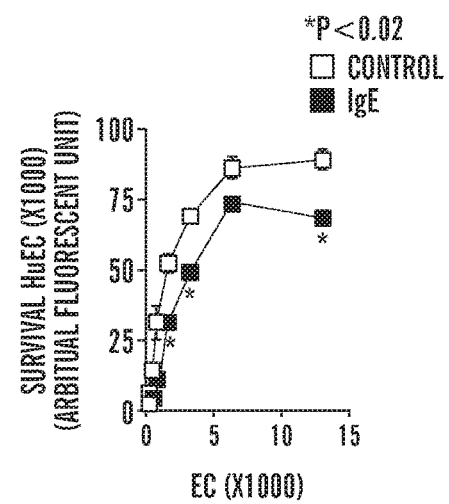
Figure 7F:
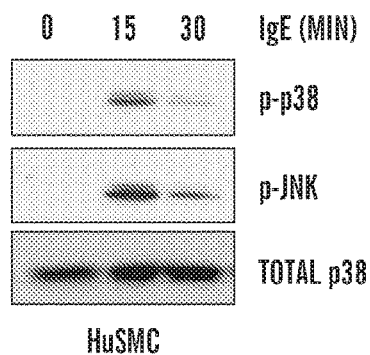
Figure 7G:
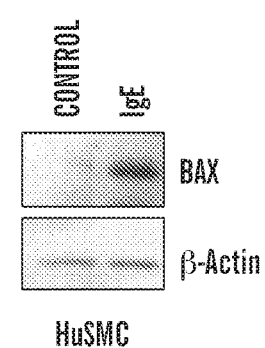
Figure 7H:
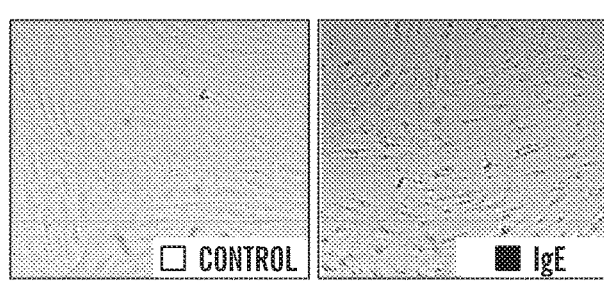
Figure 7H:
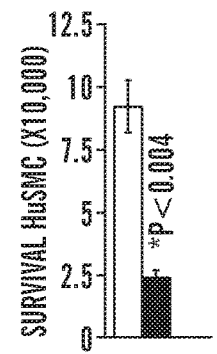
Figure 7I:
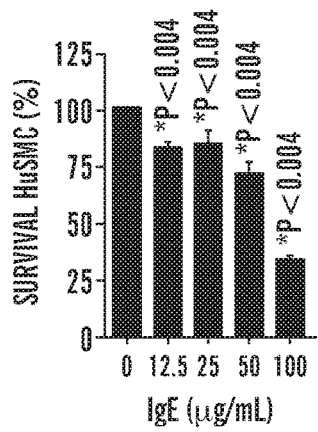
Figure 7J:
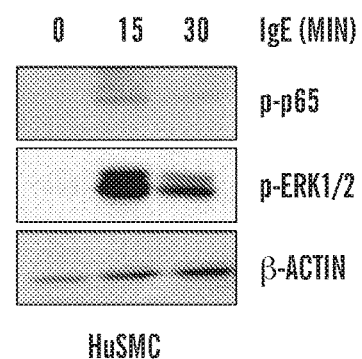
Figure 7K:
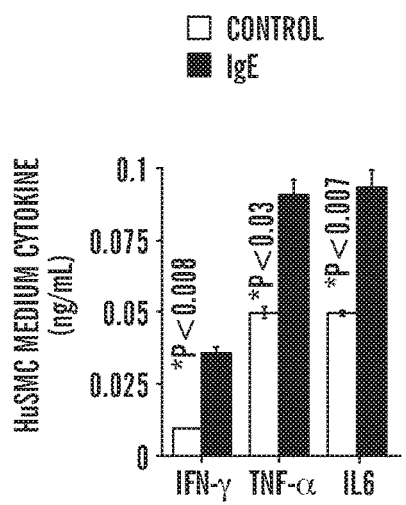
Figure 7L:
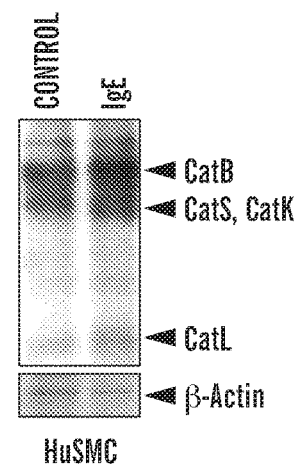
Figure 11A:
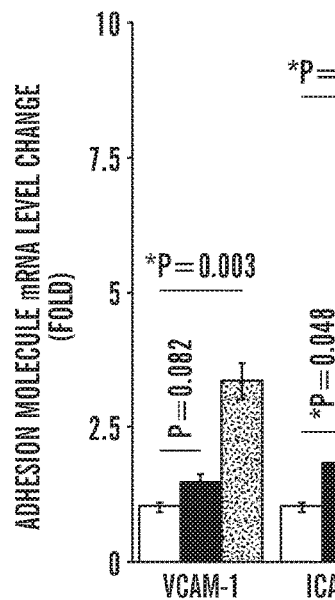
FIGS. 11A-11B depict human endothelial cell adhesion molecule expression after stimulation with purified IgE (50 μg/mL) or recombinant TNF-α (10 ng/mL).
Figure 11B:
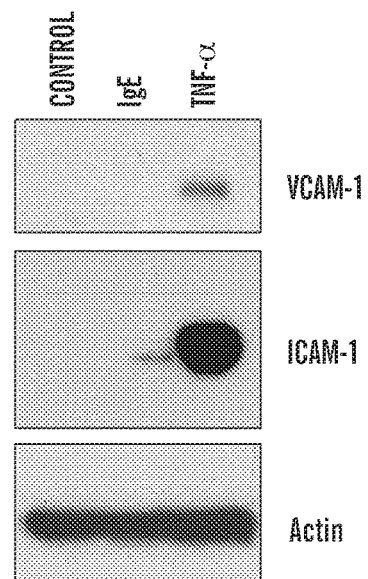

IgE and TUNEL activities localized to ECs in the adventitial microvessels and around the lumen, and to SMCs in the fibrous cap in human atherosclerotic lesions (FIG. 7A), suggesting that IgE interacts with these vascular cells. Cultured human ECs (HuECs) responded to purified human IgE by phosphorylation of p38 and JNK (FIG. 7B). Consistent with enhanced phospho-p38 and phospho-JNK, IgE increased levels of cleaved caspase-3 in HuECs (FIG. 7C, lanes 2 and 4) and promoted HuEC death in a concentration-dependent manner (FIGS. 7D and 7E). IgE had a minimal effect, however, on HuEC adhesion molecule expression. Both RT-PCR and immunoblot analysis demonstrated low levels of ICAM-1 expression and negligible VCAM-1 expression after IgE stimulation (FIGS. 11A-11B). Human aortic SMCs (HuSMCs) responded similarly to IgE. After 15 minutes of exposure to 100 µg/mL of human IgE, HuSMCs reached a peak for both p38 and JNK activation (FIG. 7F). Incubation of HuSMCs with IgE (100 µg/mL) for 3 days increased the expression of Bax, an inducer of apoptosis (39) (FIG. 7G), and provoked IgE concentration-dependent death of HuSMCs (FIGS. 7H and 7I). As in macrophages, after 15-30 minutes of treatment with 100 µg/mL of human IgE, HuSMCs produced high amounts of NF-κB phospho-p65 and phospho-ERK1/2 (FIG. 7J). Consistent with increased activation of these signaling molecules, IgE induced the expression of the HuSMC pro-inflammatory cytokines interferon-γ, TNF-α, and IL6 (FIG. 7K), and cysteinyl cathepsins B, S, L, and K (FIG. 7L). IgE may participate in atherogenesis by promoting apoptosis and by enabling cytokine, chemokine, and protease expression in macrophages, SMCs, ECs, and possibly other cells. IgE activity requires functional FcεR1 and TLR4, and IgE may be responsible for reduced pH which induces macrophage and vascular cell apoptosis in human atherosclerotic lesions.

Discussion

The results described herein establish a direct role of IgE in atherogenesis. As described herein, serum IgE levels were elevated in two independent Chinese coronary patient populations (from the Central and Eastern regions of the country). Prior to the experiments described herein, whether human atherosclerotic lesions also contain IgE and the receptor necessary for its cellular actions (the high-affinity FcεR1), and whether IgE directly affects the cellular pathways relevant to the pathogenesis of the disease, had not been studied. This study demonstrated that in human atherosclerotic lesions, IgE and its receptor FcεR1 localized to macrophages in the shoulder regions and lipid cores, to SMCs in the fibrous cap, and to ECs in the lumen and microvessels. Absence of the IgE receptor subunit FcεR1α reduced atherosclerotic lesion sizes in Apoe$^{-/-}$ mice by more than 75% in the thoracic-abdominal aorta, and by more than 55% at the aortic arch. More surprising discoveries came from the mechanistic studies: First, IgE induced macrophage MAPK activation, inflammatory cytokine and chemokine expression, and apoptosis via cooperative activities of FcεR1 and TLR4, but not TLR2. These two previously unrelated cell surface receptors formed complexes after IgE stimulation. IgE was inactive in the absence of either receptor. Second, a prior study (30) showed that the average pH in human atherosclerotic lesions (~pH 7.55) is higher than that in normal human umbilical arteries (~pH 7.24). The pH in macrophage-rich lipid cores, however, is significantly lower (~pH 7.15) than in any other areas in lesions from the same patients, including calcified areas with or without thrombosis (pH 7.73). Acidic pH in the lipid cores enhanced the binding of phospholipase A2-modified LDL particles to aortic proteoglycans and consequent uptake by macrophages for foam-cell formation (31). Further, macrophage apoptosis often appears at the edges of these lipid cores in human atherosclerotic lesions (42), though these observations remain unexplained. The current study links increased IgE and its receptor FcεR1 in macrophages from human atherosclerotic lesions with IgE-induced NHE1 activation of macrophages, which reduced extracellular pH and caused cell death (FIGS. 4A/4B).

As described herein, dose responses to mouse and human IgE of various cell types were tested. For example, as seen in FIG. 3B, phosphorylations of mouse macrophage ERK1/2, JNK, and p38 showed a clear dose curve in response to IgE from 6.25 µg/mL to 100 µg/mL. In human ECs, phosphorylation of the studied signaling molecules did not show clear dose responses (FIG. 7B), but 100 µg/mL human IgE yielded the lowest survival of ECs (FIG. 7D) and SMCs (FIG. 7I). 50 µg/mL of IgE was selected to induce mouse and human macrophage signal transduction, apoptosis, and inflammatory cytokine, chemokine, and protease expression, and 100 µg/mL human IgE to activate human SMCs and ECs. These observations prompted questions: For example, it is demonstrated herein that IgE stimulated the death of macrophages, ECs, and SMCs, but it promoted mast cell survival in several other studies (34, 43). Without wishing to be bound by theory, these different phenotypes between mast cells and macrophages, might be due to differences in expression of FcεR1 β-chain. Mast cells but not macrophages express FcεR1 β-chain (44). Although monocytes also express low levels of FcεR1 β-chain, this subunit completely disappeared after these cells mature and became macrophages, as detected by immunoblot analysis with anti-human CD20 monoclonal antibody (1:1000, Abcam, Cambridge, Mass.) (data not shown). Absence of FcεR1 β-chain in macrophages (7) may cause conformational differences of FcεR1 from those of mast cells, thereby leading to different responses to IgE.

Without wishing to be bound by theory, it is contemplated that in areas rich in macrophages and vascular ECs and SMCs within human atherosclerotic lesions (i.e., in an environment with multiple initiators of chronic inflammatory reactions), increased IgE levels (FIGS. 1A-1C) and enhanced FcεR1 expression (data not shown) may have adjuvant activity that further activates these cells that are pertinent to atherogenesis.

Vascular SMCs and ECs expressed FcεR1 under inflammatory conditions (FIG. 1D). IgE induced signal transduction, inflammatory cytokine production, and apoptosis in these vascular cells (FIG. 7), as it did in macrophages (FIG. 3), but the IgE and FcER1α immunoreactivities on ECs or SMCs in human atherosclerotic lesions were much weaker than those of macrophages (FIGS. 1A-1C and 7A). Although not tested, IgE functions (e.g., cytokine production and apoptosis) on these vascular cells may not be as profound as on macrophages within atherosclerotic lesions. Therefore, IgE may participate in EC and SMC inflammatory responses.

In the experiments described herein, age, serum HDL levels, sex, and history of diabetes mellitus were significantly different between non-CHD subjects and CHD patients in both populations. After adjustment for clinical presentation and HDL levels, sex, and history of diabetes mellitus, both fasting glucose levels and IgE were significantly higher in AMI and UAP patients than in SAP patients and non-CHD subjects. These clinical data support the in vivo relevance with the reduced atherosclerosis in Fcer1a$^{-/-}$ mice and mechanistic studies described herein.

Together, increased IgE levels in human atherosclerotic lesions and in serum from patients with unstable plaques support the concept that such "minor" immunoglobulin molecules may participate in the activation of not only MCs, but also of other blood-borne inflammatory cells, such as monocytes, macrophages, and dendritic cells, and even vascular ECs and SMCs, during the pathogenesis of human atherosclerosis.

Methods

Patient Selection.

From July to October 2008, 362 patients admitted consecutively to the Department of Cardiology at the Second Affiliated Hospital, College of Medicine, Zhejiang University, Hangzhou, China, were enrolled due to their clinical symptoms of chest pain, dyspnea, precordial discomfort, or cardiac dysfunction as defined by an ejection fraction less than 50% on echocardiography, or electrocardiogram abnormalities including ST-T changes and arrhythmia. Given the known association of IgE with allergic diseases, cancer, and autoimmunity, patients with the following conditions were excluded to limit potential confounding effects: asthma (n=22), allergic dermatitis (n=3), history of allergic diseases (n=25), arthritis (n=3), cancer (n=5), renal failure (n=34), chronic hepatic disease (n=25), rheumatic heart disease (n=2), valvular heart disease (n=2), or other cardiac diseases (n=1). The remaining 240 subjects were invited to have digital subtractive coronary angiography (DSA, FD 20, Phillips Medical Systems, Holland). Of these, 147 patients had coronary heart disease (CHD), defined by one or more main coronary arteries with ≥50% stenosis. Of the subjects with CHD, 116 had an acute coronary syndrome, including 33 with AMI, diagnosed by increasing levels of creatinine kinase-MB twofold more than the upper reference limit and troponin-I fivefold more than the upper reference limit, ischemic symptoms, or ST-T changes in electrocardiography indicative of ischemia and/or infarction; 83 with unstable angina pectoris (UAP), diagnosed with the progression of ischemic symptoms less than 3 months before admission to the hospital; and 31 with stable angina pectoris (SAP), diagnosed by predictable exertional chest discomfort more than 3 months before enrollment. A total of 93 patients with no or <50% luminal narrowing of the coronary artery were selected as non-CHD controls.

The same patient selection method was used at the College of Life Science and Technology and Center for Human Genome Research, Huazhong University of Science and Technology, Wuhan, China. The study enrolled 1413 patients from several hospitals in Central China (individuals enrolled in hospitals in Wuhan city were from Hubei province, Hunan province, Anhui province, and Henan province). 431 patients were excluded due to asthma (n=79), allergic dermatitis (n=18), history of allergic diseases (n=124), arthritis (n=8), cancer (n=13), renal failure (n=89), chronic hepatic disease (n=45), rheumatic heart disease (n=36), valvular heart disease (n=13), or other cardiac diseases (n=6). Of the remaining 982 subjects, 709 were diagnosed with CHD, and 273 with no or <50% luminal narrowing of the coronary artery were selected as non-CHD controls. Among the 709 patients with CHD, 462 had acute coronary syndrome, including 207 with AMI, 255 with UAP, and 247 with SAP.

Patient Information Recording and Sample Collection.

Patient information was recorded, including age, sex, height, weight, body-mass index (BMI), history of hypertension, history of diabetes, and smoking (consuming tobacco for >3 years). Blood samples were extracted from the sheath in the radial or femoral artery during the procedure for IgE measurement. Blood samples were prepared from the vein for serum total cholesterol (TC), triglyceride (TG), low-density lipoprotein (LDL), high-density lipoprotein (HDL), and fasting glucose levels, which were determined using standard laboratory procedures (Olympus AU5400 automated analyzer) at the clinical laboratory of the Second Affiliated Hospital, College of Medicine, Zhejiang University, Hangzhou, China, or the clinical laboratory of Union Hospital, Tongji Medical College of Huazhong University of Science and Technology, Wuhan, China. Venous blood was collected after a fast of at least 12 hours. Serum sample aliquots were stored at −80° C.

IgE Chemiluminescent Determination.

Human serum IgE levels were detected using a chemiluminescent immunoassay (Unicel DXI800, Beckman Coulter), according to the manufacturer's instructions. IgE levels of arterial and venous blood were not significantly different.

Immunohistology.

Atherosclerotic and nonatherosclerotic human carotid arteries were obtained from transplantation donors at endarterectomy or at autopsy, according to protocols pre-approved by the Human Investigative Review Committee of Harvard Medical School. Serial cryostat sections (6 μm) were prepared and stained for CD68 (macrophages, 1:500, Dako, Carpinteria, Calif.), CD31 (ECs, 1:35, Dako), α-actin (SMCs, 1:40, Enzo Diagnostics, Farmingdale, N.Y.), IgE (1:50, Novus Biologicals, Littleton, Colo.), and FcεR1α (1:50, Santa Cruz Biotechnology, Inc., Santa Cruz, Calif.) antibodies. Apoptotic cells in human atherosclerotic lesions were detected using ApopTag® Plus Peroxidase In Situ Apoptosis Detection Kit, according to the manufacturer's instructions (Millipore, Billerica, Mass.).

Animal Protocols and Atherosclerotic Lesion Characterization.

Fcer1a$^{-/-}$ mice (C57BL/6, N9,) (21) were crossbred with Apoe$^{-/-}$ mice (C57BL/6, N11, The Jackson Laboratory, Bar Harbor, Me.) to generate Apoe$^{-/-}$Fcer1a$^{-/-}$ and Apoe$^{-/-}$Fcer1a$^{+/+}$ control mice. All mice used in this study were littermates and syngeneic in the C57BL/6 background. To induce atherosclerosis, 10-week-old males from each group were fed a Western diet (Research Diets, Inc., New Brunswick, N.J.) for 12 weeks. Lesion characterizations, including thoracic-abdominal aorta oil-red O staining, aortic arch lesion intima and media areas, lesion macrophages (Mac-3), T cells (CD4 and CD3; both antibodies yielded similar staining), IL6 (Abcam), MHC class-II-positive cells, and TUNEL-positive apoptotic cells (ApopTag® Plus Peroxidase In Situ Apoptosis Kit; Millipore), were performed as previously described (18). Images were captured by a digital system, the staining area was measured using computer-assisted image quantification (Image-Pro Plus software), and immunopositive cells were counted manually. All mouse experiments were performed, and data were analyzed in a blinded fashion, by at least three observers.

Cell Culture.

Human macrophages were prepared by differentiating Ficoll gradient-separated monocytes from human blood in RPMI with 10% human serum (Gemini Bio-Products, West Sacramento, Calif.) for 10 days on Falcon PRIMARIA™ tissue culture dishes (Becton Dickinson Labware, Franklin Lakes, N.J.) without coating. Mouse thioglycolate (3%, Sigma, St. Louis, Mo.)-stimulated peritoneal macrophages were prepared from WT C57BL/6 mice (Jackson Laboratory), Fcer1a$^{-/-}$ mice (congenic C57BL/6, N>8) (21), Tlr2$^{-/-}$ mice (Jackson Laboratory, N16), and Tlr4 mice (Jackson Laboratory, C57BL/6, N8). Cells were cultured in RPMI-1640 with 10% fetal bovine serum (FBS). Human aortic SMCs and ECs were obtained from human donor aortas and subcultured at passages 2-5 in DMEM containing 10% FBS (for SMCs), or in medium 199 containing 20% FBS (for ECs).

Cytokine Production and Protease Expression.

To detect cytokine production, cells were starved in corresponding media containing 0.5% FBS overnight, then incubated for 2 days in starvation media containing IgE (50 µg/mL for macrophages; 100 µg/mL for SMCs and ECs). Mouse poorly cytokinergic monomeric IgE H1 DNP-ε-206 (50 µg/mL) (34) and highly cytokinergic aggregated IgE SPE-7 (50 µg/mL) (Sigma) with or without LPS (100 ng/mL), ox-LDL (50 µg/mL), or DNP-HSA (10 ng/mL) were used to stimulate mouse macrophages. Human IgE was obtained from Immunology Consultants Laboratory, Inc. (Newberg, Oreg., RA-80E). Unless otherwise indicated, all mouse macrophages were treated with SPE-7. Both cells and culture media were collected to detect IL6 and MCP-1 by real-time PCR (Bio-Rad, Hercules, Calif.) and ELISA (BD Biosciences, San Jose, Calif.), according to the manufacturer's instructions. Cells were lysed in a pH 5.5 lysis buffer containing 1% Triton X-100, 40 mM sodium acetate, and 1 mM EDTA to detect active cysteine proteases by active site JPM labeling, according to a protocol reported previously (18).

Immunoprecipitation and Immunoblot Analysis.

For immunoprecipitation, mouse macrophages were starved overnight in RPMI containing 0.5% FBS, followed by the addition of purified mouse IgE (50 µg/mL, Sigma) for 15 minutes. Cells were lysed in a RIPA buffer containing 50 mM Tris, pH 7.4, 150 mM NaCl, 2 mM EDTA, 1% NP-40, 0.1% SDS, 5 µg/mL aprotinin, 5 µg/mL leupeptin, and 1 mM phenylmethanesulfonyl fluoride. Lysates were pre-cleared for 1 hour with protein A/G agarose (Santa Cruz), followed by incubation overnight with 1 µg mouse FcεR1α or TLR4 polyclonal antibody (Santa Cruz), and protein A/G agarose for 1 additional hour. Immunoprecipitates were then washed with 4×1 mL cell lysis buffer, followed by separation on 8% SDS-PAGE for immunoblot analysis with rabbit anti-mouse TLR4 or FcεR1α polyclonal antibody (1:1000, Santa Cruz).

For immunoblot analysis, an equal amount of protein from each cell type preparation was separated by SDS-PAGE, blotted, and detected with different antibodies, including FcεR1α (1:1000, Santa Cruz), phospho-ERK1/2 (rabbit anti-mouse ERK1/2 Thr$^{202}$/Thr$^{204}$, 1:1000, Cell Signaling Technology, Inc., Danvers, Mass.), phospho-JNK (rabbit anti-mouse phospho-Thr/Pro/Tyr-JNK, 1:1000, Promega, Madison, Wis.), β-actin (goat anti-mouse β-actin, 1:3000, Santa Cruz), phospho-p38 MAPK (Thr$^{180}$/Tyr$^{182}$, 1:1000, Cell Signaling), and phospho-JNK antibodies (phospho-Thr/Pro/Tyr-JNK, 1:1000, Cell Signaling), phospho-p65 (NF-κB p65 Ser$^{536}$, 1:1000, Cell Signaling), cleaved caspase-3 (1:1000, Cell Signaling), Bax (1:1000, Santa Cruz), TLR4 (1:1000, Santa Cruz), NHE1 (1:1000, Millipore), and β-actin (1:3000, Santa Cruz).

Cell Death Analysis.

To detect IgE-induced apoptosis, human and mouse macrophages and HuSMC were cultured on 8-well chamber slides, 96-well plates, or 6-well plate pre-coated with 1% gelatin. After overnight starvation, cells were stimulated with IgE (50 µg/mL for macrophages and 100 µg/mL for HuSMC) for 3~4 days before detecting apoptotic cells using TUNEL staining (IN SITU CELL DEATH DETECTION KIT™, Roche Diagnostics Corp., Indianapolis, Ind.), MTT cell proliferation assay (Millipore), or CyQUANT™ cell proliferation assay (Invitrogen, Carlsbad, Calif.), according to the manufacturer's instructions. To detect mitochondria cytochrome C release, IgE-stimulated macrophages were lysed in a cytosol extraction buffer mix, homogenized, supernatant cytosol fraction separated by centrifugation, and pellet resuspended in a mitochondria extraction buffer mix, according to the manufacturer's instructions (Abcam, Cat# AB65311). Cytosol and mitochondria fractions were separated and immunoblotted for cytochrome C (1:1000, Abcam) and Bax (1:1000, Santa Cruz). In pH experiments, we used custom-made acidic (pH6.5) and neutral (pH7.5) pH DMEM (Hyclone) for human macrophages and HEPES-balanced RPMI-1640 medium for mouse macrophages.

Statistical Analysis.

All data were expressed as mean±SEM. For patient serum sample chemiluminescent immunoassay data, those with normal distribution and homogeneity of variance, independent two-tailed Student's t test, and one-way analysis of variance (ANOVA) LSD test were used for the comparison between two groups and among multiple groups, respectively. Non-parametric Kruskal-Wallis H test was used for multiple group comparisons with skewed data distribution or heterogeneity of variance. For the ranked data, Fisher's exact test and Pearson chi-square test were used for the comparison between two groups and among multiple groups, respectively. To analyze the correlation of serum IgE and other values, we used Pearson's correlation test and an independent two-tailed Student's t test. To examine the influence of potential confounders to serum IgE levels, we adjusted for age, sex, BMI, hypertension, smoking, diabetes mellitus, fasting glucose, and serum lipid levels, using a multiple linear regression model. All in vitro cell culture or animal data were analyzed using non-parametric Mann-Whitney test due to the small sample size and abnormal data distribution. SPSS16 version was used for analysis, and P<0.05 were considered statistically significant.

REFERENCES

1. Kinet JR The high-affinity IgE receptor (Fc epsilon RI): from physiology to pathology. *Annu Rev Immunol.* 1999; 17:931-972.
2. Gould H J, Sutton B J. IgE in allergy and asthma today. *Nat Rev Immunol.* 2008; 8(3):205-217.
3. Leslie M. Mast cells show their might. *Science.* 2007; 317(5838):614-616.
4. Sun J, Sukhova G K, Wolters P J, Yang M, Kitamoto S, Libby P, MacFarlane L A, Mallen-St Clair J, Shi GP. Mast cells promote atherosclerosis by releasing proinflammatory cytokines. *Nat Med.* 2007; 13(6):719-724.
5. Grayson M H, Cheung D, Rohlfing M M, Kitchens R, Spiegel D E, Tucker J, Battaile J T, Alevy Y, Yan L, Agapov E, Kim E Y, Holtzman M J. Induction of high-affinity IgE receptor on lung dendritic cells during viral infection leads to mucous cell metaplasia. *J Exp Med.* 2007; 204(11):2759-2769.

6. Le T, Tversky J, Chichester K L, Bieneman A P, Huang S K, Wood R A, Schroeder J T. Interferons modulate Fc epsilon RI-dependent production of autoregulatory IL-10 by circulating human monocytoid dendritic cells. *J Allergy Clin Immunol.* 2009; 123(1):217-223.
7. Dombrowicz D, Quatannens B, Papin J P, Capron A, Capron M. Expression of a functional Fc epsilon RI on rat eosinophils and macrophages. *J Immunol.* 2000; 165(3):1266-1271.
8. Katoh N, Kraft S, Wessendorf J H, Bieber T. The high-affinity IgE receptor (FcepsilonRI) blocks apoptosis in normal human monocytes. *J Clin Invest.* 2000 January; 105(2):183-190.
9. Mancardi D A, Iannascoli B, Hoos S, England P, Daeron M, Bruhns P. FcgammaRIV is a mouse IgE receptor that resembles macrophage FcepsilonRI in humans and promotes IgE-induced lung inflammation. *J Clin Invest.* 2008; 118(11):3738-3750.
10. Bieber T. Fc epsilon RI on human epidermal Langerhans cells: an old receptor with new structure and functions. *Int Arch Allergy Immunol.* 1997; 113(1-3):30-34.
11. Laukkanen J, Lehtolainen P, Gough P J, Greaves D R, Gordon S, Ylä-Herttuala S. Adenovirus-mediated gene transfer of a secreted form of human macrophage scavenger receptor inhibits modified low-density lipoprotein degradation and foam-cell formation in macrophages. *Circulation.* 2000; 101(10):1091-1096.
12. Jalkanen J, Leppänen P, Närvänen O, Greaves D R, Ylä-Herttuala S. Adenovirus-mediated gene transfer of a secreted decoy human macrophage scavenger receptor (SR-AI) in LDL receptor knock-out mice. *Atherosclerosis.* 2003; 169(1):95-103.
13. Moore K J, Kunjathoor V V, Koehn S L, Manning J J, Tseng A A, Silver J M, McKee M, Freeman M W. Loss of receptor-mediated lipid uptake via scavenger receptor A or CD36 pathways does not ameliorate atherosclerosis in hyperlipidemic mice. *J Clin Invest.* 2005; 115(8):2192-2201.
14. Jalkanen J, Leppänen P, Närvänen O, Greaves D R, Ylä-Herttuala S. Adenovirus-mediated gene transfer of a secreted decoy human macrophage scavenger receptor (SR-AI) in LDL receptor knock-out mice. *Atherosclerosis.* 2003; 169(1):95-103.
15. Devries-Seimon T, Li Y, Yao P M, Stone E, Wang Y, Davis R J, Flavell R, Tabas I. Cholesterol-induced macrophage apoptosis requires ER stress pathways and engagement of the type A scavenger receptor. *J Cell Biol.* 2005; 171(1):61-73.
16. Michelsen K S, Wong M H, Shah P K, Zhang W, Yano J, Doherty T M, Akira S, Rajavashisth T B, Arditi M. Lack of Toll-like receptor 4 or myeloid differentiation factor 88 reduces atherosclerosis and alters plaque phenotype in mice deficient in apolipoprotein E. *Proc Natl Acad Sci USA.* 2004; 101(29):10679-10684.
17. Mullick A E, Tobias P S, Curtiss L K. Modulation of atherosclerosis in mice by Toll-like receptor 2. *J Clin Invest.* 2005; 115(11):3149-3156.
18. Sukhova G K, Zhang Y, Pan J H, Wada Y, Yamamoto T, Naito M, Kodama T, Tsimikas S, Witztum J L, Lu M L, Sakara Y, Chin M T, Libby P, Shi G P. Deficiency of cathepsin S reduces atherosclerosis in LDL receptor-deficient mice. *J Clin Invest.* 2003; 111(6):897-906.
19. Kovanen P T, Kaartinen M, Paavonen T. Infiltrates of activated mast cells at the site of coronary atheromatous erosion or rupture in myocardial infarction. *Circulation.* 1995; 92(5):1084-1088.
20. Leon M L, Zuckerman S H. Gamma interferon: a central mediator in atherosclerosis. *Inflamm Res.* 2005; 54(10):395-411.
21. Dombrowicz D, Flamand V, Brigman K K, Koller B H, Kinet J P. Abolition of anaphylaxis by targeted disruption of the high affinity immunoglobulin E receptor alpha chain gene. *Cell.* 1993; 75(5):969-976.
22. Tabas I. Consequences and therapeutic implications of macrophage apoptosis in atherosclerosis: the importance of lesion stage and phagocytic efficiency. *Arterioscler Thromb Vasc Biol.* 2005; 25(11):2255-2264.
23. Eshhar Z, Ofarim M, Waks T. Generation of hybridomas secreting murine reaginic antibodies of anti-DNP specificity. *J Immunol.* 1980; 124(2):775-780.
24. Lutgens E, Lutgens S P, Faber B C, Heeneman S, Gijbels M M, de Winther M P, Frederik P, van der Made I, Daugherty A, Sijbers A M, Fisher A, Long C J, Saftig P, Black D, Daemen M J, Cleutjens K B. Disruption of the cathepsin K gene reduces atherosclerosis progression and induces plaque fibrosis but accelerates macrophage foam cell formation. *Circulation.* 2006; 113(1):98-107.
25. Gao B, Wang Y, Tsan M F. The heat sensitivity of cytokine-inducing effect of lipopolysaccharide. *J Leukoc Biol.* 2006; 80(2):359-366.
26. Akira S, Takeda K. Toll-like receptor signalling. *Nat Rev Immunol.* 2004; 4(7):499-511.
27. Seimon T A, Obstfeld A, Moore K J, Golenbock D T, Tabas I. Combinatorial pattern recognition receptor signaling alters the balance of life and death in macrophages. *Proc Natl Acad Sci USA.* 2006; 103(52):19794-19799.
28. Seimon T A, Nadolski M J, Liao X, Magallon J, Nguyen M, Feric N T, Koschinsky M L, Harkewicz R, Witztum J L, Tsimikas S, Golenbock D, Moore K J, Tabas I. Atherogenic lipids and lipoproteins trigger CD36-TLR2-dependent apoptosis in macrophages undergoing endoplasmic reticulum stress. *Cell Metab.* 2010; 12(5):467-482.
29. Yu L C, Montagnac G, Yang P C, Conrad D H, Benmerah A, Perdue M H. Intestinal epithelial CD23 mediates enhanced antigen transport in allergy: evidence for novel splice forms. *Am J Physiol Gastrointest Liver Physiol.* 2003; 285(1):G223-G234.
30. Naghavi M, John R, Naguib S, Siadaty M S, Grasu R, Kurian K C, van Winkle W B, Soller B, Litovsky S, Madjid M, Willerson J T, Casscells W. pH Heterogeneity of human and rabbit atherosclerotic plaques; a new insight into detection of vulnerable plaque. *Atherosclerosis.* 2002; 164(1):27-35.
31. Lähdesmäki K, Plihtari R, Soininen P, Hurt-Camejo E, Ala-Korpela M, Oörni K, Kovanen P T. Phospholipase A(2)-modified LDL particles retain the generated hydrolytic products and are more atherogenic at acidic pH. *Atherosclerosis.* 2009; 207(2):352-359.
32. Yang J, Liu X, Bhalla K, Kim C N, Ibrado A M, Cai J, Peng T I, Jones D P, Wang X. Prevention of apoptosis by Bcl-2: release of cytochrome c from mitochondria blocked. *Science.* 1997; 275(5303):1129-1132.
33. Yu L, Quinn D A, Garg H G, Hales C A. Deficiency of the NHE1 gene prevents hypoxia-induced pulmonary hypertension and vascular remodeling. *Am J Respir Crit Care Med.* 2008; 177(11):1276-1284.
34. Kitaura J, Song J, Tsai M, Asai K, Maeda-Yamamoto M, Mocsai A, Kawakami Y, Liu F T, Lowell C A, Barisas B G, Galli S J, Kawakami T. Evidence that IgE molecules mediate a spectrum of effects on mast cell survival and activation via aggregation of the FcepsilonRI. *Proc Natl Acad Sci USA.* 2003; 100(22):12911-12916.

35. Matsuda K, Piliponsky A M, Iikura M, Nakae S, Wang E W, Dutta S M, Kawakami T, Tsai M, Galli S J. Monomeric IgE enhances human mast cell chemokine production: IL-4 augments and dexamethasone suppresses the response. *J Allergy Clin Immunol.* 2005; 116(6):1357-1363.

36. Takenaka H, Ushio H, Niyonsaba F, Jayawardana S T, Hajime S, Ikeda S, Ogawa H, Okumura K. Synergistic augmentation of inflammatory cytokine productions from murine mast cells by monomeric IgE and toll-like receptor ligands. *Biochem Biophys Res Commun.* 2010; 391(1):471-476.

37. Geng H, Wang A, Rong G, Zhu B, Deng Y, Chen J, Thong R. The effects of ox-LDL in human atherosclerosis may be mediated in part via the toll-like receptor 4 pathway. *Mol Cell Biochem.* 2010; 342(1-2):201-206.

38. Su X, Ao L, Shi Y, Johnson T R, Fullerton D A, Meng X. Oxidized Low Density Lipoprotein Induces Bone Morphogenetic Protein-2 in Coronary Artery Endothelial Cells via Toll-like Receptors 2 and 4. *J Biol Chem.* 2011; 286(14):12213-12220.

39. Gavathiotis E, Suzuki M, Davis M L, Pitter K, Bird G H, Katz S G, Tu H C, Kim H, Cheng E H, Tjandra N, Walensky L D. BAX activation is initiated at a novel interaction site. *Nature.* 2008; 455(7216):1076-1081.

40. Szczeklik A, Sladek K, Szczerba A, Dropinski J. Serum immunoglobulin E response to myocardial infarction. *Circulation.* 1988; 77(6):1245-1249.

41. Kovanen P T, Manttari M, Palosuo T, Manninen V, Aho K. Prediction of myocardial infarction in dyslipidemic men by elevated levels of immunoglobulin classes A, E, and G, but not M. *Arch Intern Med.* 1998; 158(13):1434-1439.

42. Hegyi L, Skepper J N, Cary N R, Mitchinson M J. Foam cell apoptosis and the development of the lipid core of human atherosclerosis. *J Pathol.* 1996; 180(4):423-429.

43. Asai K, Kitaura J, Kawakami Y, Yamagata N, Tsai M, Carbone D P, Liu F T, Galli S J, Kawakami T. Regulation of mast cell survival by IgE. *Immunity.* 2001; 14(6):791-800.

44. Donnadieu E, Jouvin M H, Kinet J P. A second amplifier function for the allergy-associated Fc(epsilon)RI-beta subunit. *Immunity.* 2000; 12(5):515-523.

45. Shin M H, Min H K. Effects of anti-IgE mAb on serum IgE, Fc epsilon RII/CD23 expression on splenic B cells and worm burden in mice infected with *Paragonimus westermani*. *Korean J Parasitol.* 1997; 35(1):47-54.

46. King C L, Gallin J I, Malech H L, Abramson S L, Nutman T B. Regulation of immunoglobulin production in hyperimmunoglobulin E recurrent-infection syndrome by interferon gamma. *Proc Natl Acad Sci USA.* 1989; 86(24):10085-10089.

47. Yavuz H, Chee R. A review on the vascular features of the hyperimmunoglobulin E syndrome. *Clin Exp Immunol.* 2010; 159(3):238-244.

48. Lee W H, Lee Y, Kim J R, Chu J A, Lee S Y, Jung J O, Kim J S, Kim S, Seo J D, Rhee S S, Park J R. Activation of monocytes, T-lymphocytes and plasma inflammatory markers in angina patients. *Exp Mol Med.* 1999; 31(3):159-164.

49. Abramson J, Pecht I. Regulation of the mast cell response to the type 1 Fc epsilon receptor. *Immunol Rev.* 2007; 217:231-254.

50. Bot I, de Jager S C, Bot M, van Heiningen S H, de Groot P, Veldhuizen R W, van Berkel T J, von der Thilsen J H, Biessen E A. The neuropeptide substance P mediates adventitial mast cell activation and induces intraplaque hemorrhage in advanced atherosclerosis. *Circ Res.* 2010; 106(1):89-92.

51. Bot I, de Jager S C, Zernecke A, Lindstedt K A, van Berkel T J, Weber C, Biessen E A. Perivascular mast cells promote atherogenesis and induce plaque destabilization in apolipoprotein E-deficient mice. *Circulation.* 2007; 115(19):2516-2525.

52. Sukhova G K, Shi G P, Simon D I, Chapman H A, Libby P. Expression of the elastolytic cathepsins S and K in human atheroma and regulation of their production in smooth muscle cells. *J Clin Invest.* 1998; 102(3):576-583.

53. Geng Y J, Wu Q, Muszynski M, Hansson G K, Libby P. Apoptosis of vascular smooth muscle cells induced by in vitro stimulation with interferon-gamma, tumor necrosis factor-alpha, and interleukin-1 beta. *Arterioscler Thromb Vasc Biol.* 1996; 16(1):19-27.

54. Li J H, Pober J S. The cathepsin B death pathway contributes to TNF plus IFN-gamma-mediated human endothelial injury. *J Immunol.* 2005; 175(3):1858-1866.

55. Sun J, Zhang J, Lindholt J S, Sukhova G K, Liu J, He A, Abrink M, Pejler G, Stevens R L, Thompson R W, Ennis T L, Gurish M F, Libby P, Shi G P. Critical role of mast cell chymase in mouse abdominal aortic aneurysm formation. *Circulation.* 2009; 120(11):973-982.

56. Zhou X, Hansson G K. Detection of B cells and proinflammatory cytokines in atherosclerotic plaques of hypercholesterolaemic apolipoprotein E knockout mice. *Scand J Immunol.* 1999; 50(1):25-30.

57. Moos M P, John N, Grabner R, Nossmann S, Günther B, Vollandt R, Funk C D, Kaiser B, Habenicht A J. The lamina adventitia is the major site of immune cell accumulation in standard chow-fed apolipoprotein E-deficient mice. *Arterioscler Thromb Vasc Biol.* 2005; 25(11):2386-2391.

58. Roselaar S E, Kakkanathu P X, Daugherty A. Lymphocyte populations in atherosclerotic lesions of apoE−/− and LDL receptor−/− mice. Decreasing density with disease progression. *Arterioscler Thromb Vasc Biol.* 1996; 16(8):1013-1018.

59. Young J L, Libby P, Schonbeck U. Cytokines in the pathogenesis of atherosclerosis. *Thromb Haemost.* 2002; 88(4):554-567.

TABLE 1

Clinical data and serum IgE comparison between patients with and without coronary heart disease (CHD) from Central China.

| Variables | non-CHD (n = 273) | CHD (n = 709) | P value |
|---|---|---|---|
| Age (years) | 56.48 ± 0.71 | 60.84 ± 0.37 | 0.000[a] |
| Body-mass index (kg/mm$^2$) | 23.43 ± 0.16 | 23.75 ± 0.08 | 0.050[a] |
| Fasting glucose (mg/dL) | 93.51 ± 1.13 | 96.98 ± 0.86 | 0.197[a] |
| Total cholesterol (mg/dL) | 182.84 ± 1.66 | 195.86 ± 1.04 | 0.000[a] |
| Triglyceride (mg/dL) | 144.10 ± 5.35 | 137.87 ± 2.44 | 0.401[a] |
| High-density lipoprotein (mg/dL) | 49.29 ± 0.74 | 47.28 ± 0.41 | 0.044[a] |
| Low-density lipoprotein (mg/dL) | 102.58 ± 1.38 | 115.28 ± 0.90 | 0.000[a] |
| Immunoglobulin E (IU/mL) | 57.13 ± 5.35 | 90.61 ± 2.91 | 0.000[a] |
| Sex (male, %) | 47.99 | 52.19 | 0.238[b] |
| Smoking (%) | 28.94 | 35.68 | 0.045[b] |
| Hypertension (%) | 15.02 | 64.74 | 0.000[b] |
| Diabetes mellitus (%) | 10.62 | 16.78 | 0.016[b] |

Data are presented as mean ± SEM or a percentage.
[a]Mann-Whitney U test.
[b]Pearson chi-square test.
P < 0.05 was considered statistically significant.

TABLE 2

Clinical data and serum IgE comparison among CHD subgroups and non-CHD subjects from Central China.

| Variables | non-CHD (n = 273) | AMI (n = 207) | UAP (n = 255) | SAP (n = 247) | P value |
|---|---|---|---|---|---|
| Age (years) | 56.48 ± 0.71 | 61.87 ± 0.70** | 61.69 ± 0.66**▲ | 59.03 ± 0.57**# | 0.000$^a$ |
| Body-mass index (kg/mm$^2$) | 23.43 ± 0.16 | 23.88 ± 0.16* | 23.64 ± 0.14 | 23.76 ± 0.15 | 0.194$^a$ |
| Fasting glucose (mg/dL) | 93.51 ± 1.13 | 95.22 ± 1.50 | 99.38 ± 1.61 | 95.98 ± 1.32 | 0.402$^a$ |
| Total cholesterol (mg/dL) | 182.84 ± 1.66 | 194.98 ± 1.89** | 202.11 ± 1.64**##▲▲ | 189.21 ± 1.76*# | 0.000$^a$ |
| Triglyceride (mg/dL) | 144.10 ± 5.35 | 129.36 ± 3.37 | 141.44 ± 4.50 | 143.61 ± 4.77 | 0.052$^a$ |
| High-density lipoprotein (mg/dL) | 49.29 ± 0.74 | 45.86 ± 0.75** | 48.89 ± 0.64## | 47.04 ± 0.75* | 0.001$^a$ |
| Low-density lipoprotein (mg/dL) | 102.58 ± 1.38 | 109.16 ± 1.55** | 120.79 ± 1.46**##▲▲ | 114.70 ± 1.57**# | 0.000$^a$ |
| Immunoglobulin E (IU/mL) | 57.13 ± 5.35 | 126.08 ± 6.37** | 89.60 ± 4.89**##▲▲ | 61.91 ± 2.93 | 0.000$^a$ |
| Sex (male, %) | 47.99 | 57.49 | 50.20 | 49.80 | 0.196$^b$ |
| Smoking (%) | 28.94 | 30.43 | 47.06**##▲▲ | 28.34 | 0.000$^b$ |
| Hypertension (%) | 15.02 | 58.45** | 70.20**# | 64.37** | 0.000$^b$ |
| Diabetes mellitus (%) | 10.62 | 14.00 | 21.57*#▲ | 14.17 | 0.005$^b$ |

Data are presented as mean ± SEM or a percentage.
$^a$Kruskal-Wallis test;
$^b$Pearson Chi-Square test;
*P < 0.05 vs. non-CHD;
**P < 0.01 vs. non-CHD;
P < 0.05 vs. AMI;
P < 0.01 vs. AMI;
▲P < 0.05 vs. SAP and
▲▲P < 0.01 vs. SAP.
P < 0.05 was considered statistically significant between the groups.

TABLE 3

Variables associated with serum IgE in all subjects (n = 982).

| Variables | Correlation Coefficient | t value | P value$^a$ |
|---|---|---|---|
| Age (years) | 0.053 | | 0.243$^a$ |
| Sex | 0.131 | 0.094$^b$ | |
| Body-mass index (kg/mm$^2$) | 0.042 | | 0.188$^a$ |
| Hypertension | 0.052 | 0.106$^b$ | |
| Smoking | 0.063 | 0.049$^b$ | |
| Diabetes mellitus | 0.096 | 0.730$^b$ | |
| Fasting glucose (mg/dL) | −0.023 | | 0.476$^a$ |
| Total cholesterol (mg/dL) | 0.019 | | 0.557$^a$ |
| Triglyceride (mg/dL) | 0.051 | | 0.113$^a$ |
| High-density lipoprotein (mg/dL) | −0.020 | | 0.538$^a$ |
| Low-density lipoprotein (mg/dL) | 0.012 | | 0.700$^a$ |

$^a$Pearson's correlation test;
$^b$Independent sample t test.

TABLE 4

Clinical data and serum IgE comparisons between patients with and without coronary heart disease (CHD) from Eastern China.

| Variables | non-CHD (n = 93) (Mean ± S.E.) | CHD (n = 147) (Mean ± S.E.) | t value | P value* |
|---|---|---|---|---|
| Age (year) | 58.45 ± 1.12 | 65.79 ± 0.81 | 5.408 | <0.001 |
| Body-mass index (kg/mm$^2$) | 23.28 ± 0.41 | 23.70 ± 0.26 | 0.591 | 0.357 |
| Fasting glucose (mg/dL) | 98.02 ± 2.03 | 101.17 ± 2.37 | 1.011 | 0.313 |
| Total cholesterol (mg/dL) | 161.60 ± 3.28 | 163.01 ± 3.80 | 0.281 | 0.779 |
| Triglyceride (mg/dL) | 156.94 ± 10.84 | 170.63 ± 12.46 | 0.765 | 0.445 |
| High-density lipoprotein (mg/dL) | 51.05 ± 1.41 | 47.24 ± 1.01 | −2.245 | 0.026 |
| Low-density lipoprotein (mg/dL) | 91.15 ± 2.81 | 94.48 ± 3.06 | 0.803 | 0.423 |
| Immunoglobulin E (IU/mL) | 62.21 ± 5.69 | 99.55 ± 9.84 | 3.286 | 0.001 |

| | Non-CHD (n = 93) | | CHD (n = 147) | | |
|---|---|---|---|---|---|
| | 0*** | 1*** | 0*** | 1*** | P value** |
| Sex | 40 | 53 | 42 | 105 | 0.026 |
| Smoking | 62 | 31 | 91 | 56 | 0.493 |
| Hypertension | 34 | 59 | 48 | 99 | 0.577 |
| Diabetes mellitus | 84 | 9 | 116 | 31 | 0.022 |

*Independent sample t test.
**Fisher's exact test.
P < 0.05 was considered statistically significant.
***Sex: 0-female, 1-male; Smoking: 0-non-smoker, 1-smoker; Hypertension: 0-no, 1-yes; Diabetes mellitus: 0-no, 1-yes.

TABLE 5

Clinical data and serum IgE comparisons among CHD subgroups and non-CHD subjects from Eastern China

| Variables | non-CHD (n = 93) | AMI (n = 33) | UAP (n = 83) | SAP (n = 31) | P value[d] |
|---|---|---|---|---|---|
| Age (year) | 58.45 ± 1.12 | 69.88 ± 1.83** | 65.23 ± 0.96**[#] | 62.94 ± 1.95*[##] | 0.000[a] |
| Body-mass index (kg/mm$^2$) | 23.45 ± 0.35 | 22.75 ± 0.53 | 23.63 ± 0.34 | 24.92 ± 0.60 | 0.059[a] |
| Fasting glucose (mg/dL) | 98.02 ± 2.03 | 116.17 ± 6.52 | 97.23 ± 2.57[#] | 95.06 ± 4.58[#] | 0.004[b] |
| Total cholesterol (mg/dL) | 161.60 ± 3.28 | 155.85 ± 5.27 | 164.55 ± 5.49 | 167.18 ± 9.27 | 0.843[b] |
| Triglyceride (mg/dL) | 156.94 ± 10.84 | 129.88 ± 8.42 | 176.21 ± 13.01 | 203.11 ± 48.81 | 0.233[a] |
| High-density lipoprotein (mg/dL) | 51.05 ± 1.41 | 47.64 ± 2.07 | 46.65 ± 1.30 | 48.39 ± 2.54 | 0.145[a] |
| Low-density lipoprotein (mg/dL) | 91.15 ± 2.81 | 90.85 ± 4.45 | 96.14 ± 4.45 | 94.14 ± 7.20 | 0.889[a] |
| Immunoglobulin E (IU/mL) | 62.21 ± 5.69 | 133.63 ± 26.28** | 97.72 ± 12.41*▲ | 68.18 ± 15.76[##] | 0.003[a] |

| | non-CHD (n = 93) | | AMI (n = 33) | | UAP (n = 83) | | SAP (n = 31) | | P value[c,d] |
|---|---|---|---|---|---|---|---|---|---|
| | 0 | 1 | 0 | 1 | 0 | 1 | 0 | 1 | |
| Sex | 40 | 53 | 13 | 20 | 21 | 62 | 8 | 23 | 0.058 |
| Smoking | 62 | 31 | 19 | 14 | 52 | 31 | 20 | 11 | 0.816 |
| Hypertension | 34 | 59 | 12 | 21 | 26 | 57 | 10 | 21 | 0.884 |
| Diabetes mellitus | 84 | 9 | 25 | 8 | 67 | 16 | 24 | 7 | 0.121 |

[a]one way ANOVA LSD test (normal distribution and homogeneity of variance);
[b]Kruskal-Wallis test (abnormal distribution or heterogeneity of variance);
[c]Pearson Chi-Square test.
[d]$P < 0.05$ was considered statistically significant between the groups.
*$P < 0.05$ vs. non-CHD;
**$P < 0.01$ vs. non-CHD;
[#]$P < 0.05$ vs. AMI;
[##]$P < 0.01$ vs. AMI;
▲$P < 0.05$, vs. SAP

TABLE 6

Variables associated with serum IgE in all subjects (n = 240) from Eastern China.

| | Correlation Coefficient | t value | P value |
|---|---|---|---|
| Age (year) | 0.027 | | 0.676* |
| Sex | | -1.669 | 0.096** |
| Body-mass index (kg/mm$^2$) | 0.000 | | 0.996* |
| Hypertension | | 0.334 | 0.739** |
| Diabetes mellitus | | -1.292 | 0.203** |
| Smoking | | -0.772 | 0.441** |
| Fasting glucose (mg/dL) | 0.218 | | 0.001* |
| Total cholesterol (mg/dL) | 0.108 | | 0.104* |
| Triglyceride (mg/dL) | -0.037 | | 0.575* |
| High-density lipoprotein (mg/dL) | 0.027 | | 0.686* |
| Low-density lipoprotein (mg/dL) | 0.121 | | 0.068* |

*Pearson's correlation test;
**Independent sample t test.

TABLE 7

Mouse serum lipid profiles

| Genotype | Total cholesterol (mg/dL) | HDL (mg/dL) | Triglyceride (mg/dL) | LDL (mg/dL) |
|---|---|---|---|---|
| Apoe$^{-/-}$ Fcer1a$^{+/+}$ (n = 18) | 1449.49 ± 85.65 | 35.38 ± 1.33 | 230.77 ± 17.89 | 1367.96 ± 82.69 |
| Apoe$^{-/-}$ Fcer1a$^{-/-}$ (n = 11) | 1512.44 ± 140.25 | 41.08 ± 1.85 | 282.42 ± 30.57 | 1414.88 ± 135.61 |
| P value* | 0.589 | 0.019* | 0.080 | 0.653 |

*Mann-Whitney U test,
$P < 0.05$ is considered statistically significant.

Example 2: Role of IgE in Human and Experimental Abdominal Aortic Aneurysm (AAA)

IgE and its receptor FceR1 on CD68$^+$ macrophages in human AAA lesions induce apoptosis of macrophages, smooth muscle cells, and endothelial cells. SMCs were protected from apoptosis in areas without IgE.

Plasma IgE levels were found to be higher in AAA patients than in age-matched controls (Table 8). In mice, serum IgE levels are increased after Apoe$^{-/-}$ mice develop AAA (FIG. 12A). Absence of IgE receptor FceR1 protected Apoe$^{-/-}$ mice from AAA formation (FIG. 12B-12I).

In human AAA lesions, co-localization of IgE to macrophages induces pH reduction, essential to cause macrophage apoptosis (*J Clin Invest.* 2011; 121:3564). In contrast, areas without macrophages or IgE do not show pH changes. pHrodo was used as a pH indicator to detect tissue pH reductions (data not shown).

In AAA lesions from Apoe$^{-/-}$ mice, areas rich in macrophages (Mac-3) and IgE are prone to pH reductions and apoptosis (data not shown).

Figure 13A:
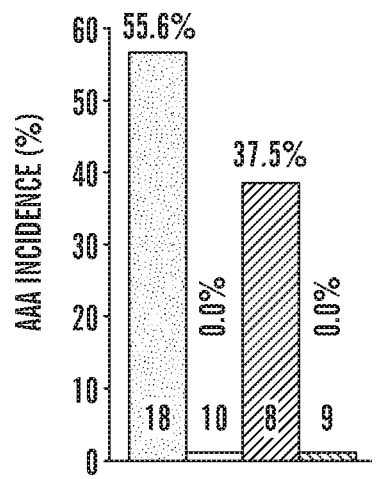
FIGS. 13A-13C demonstrate that macrophage activation by IgE is essential to experimental AAA formation in Apoe$^{-/-}$ mice. Reduced AAA formation in Apoe-/-Fcer1a$^{-/-}$ mice can be partially recovered after recipient mice receiving macrophages from Apoe$^{-/-}$ mice but not those from Apoe-/-Fcer1a$^{-/-}$ mice. The first bar on each graph represents Apoe$^{-/-}$ mice, the second bar represents Apoe-/-Fcε1a-/- mice, the third bar represents Apoe-/-Fcε1a-/- +Apoe-/- macrophage mice, and the fourth bar represents Apoe-/-Fcε1a-/- +Apoe-/-Fcε1a-/- macrophage mice.
Figure 13B:
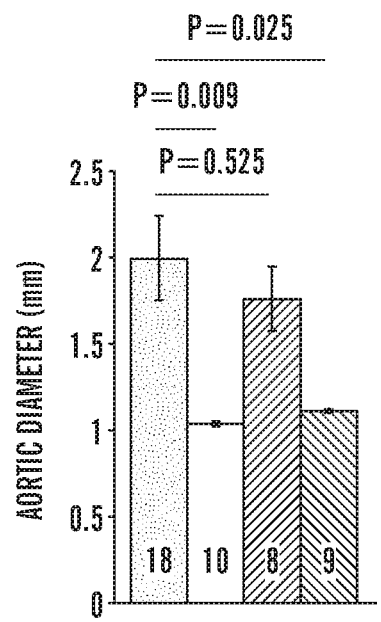
Figure 13C:
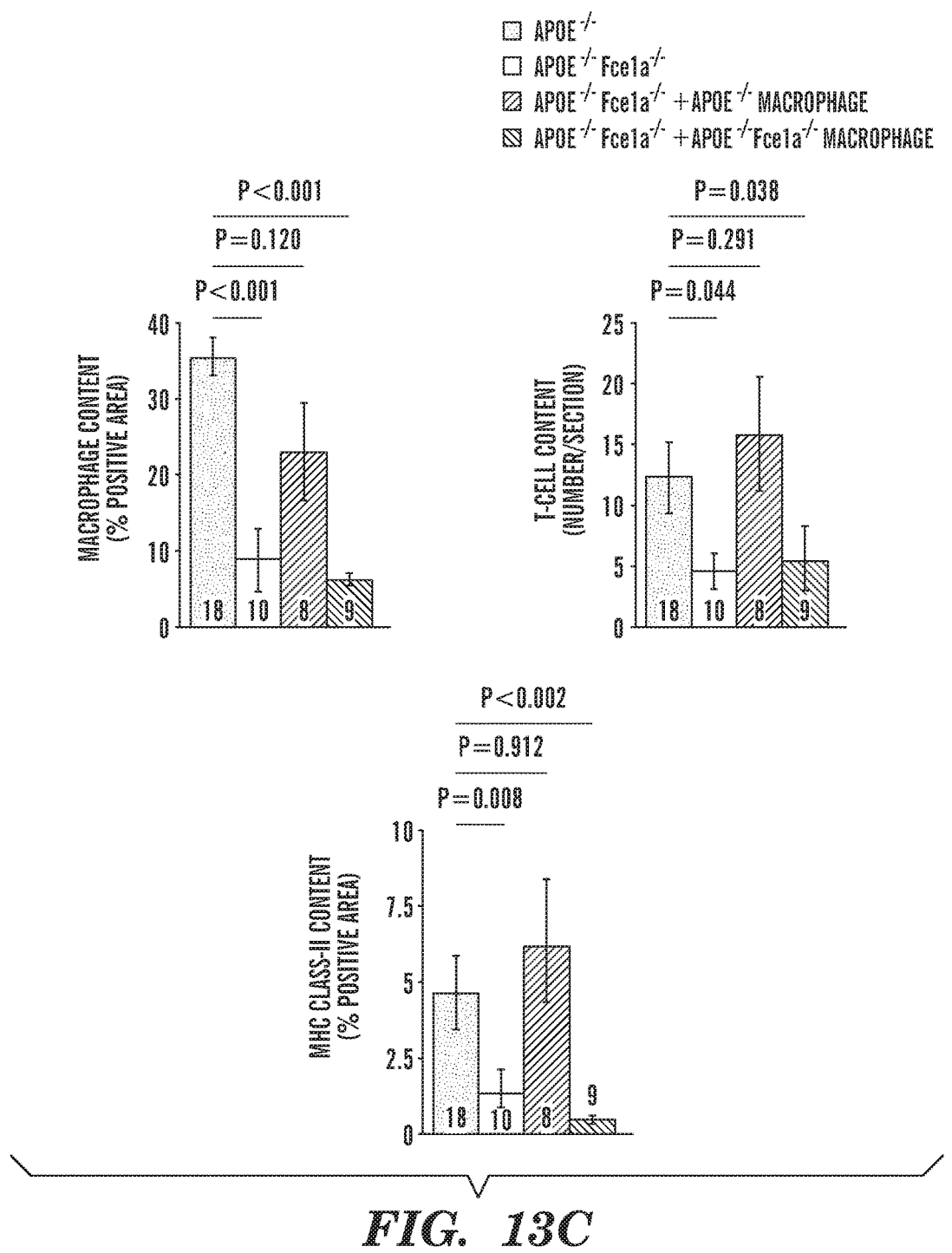

Macrophage activation by IgE is essential to experimental AAA formation in Apoe$^{-/-}$ mice (FIGS. 13A-13C). FcεR1 immunostaining was performed to detect macrophages in Apoe$^{-/-}$ mice or Apoe-/-Fcer1a$^{-/-}$ mice receiving adoptive transfer of macrophages from Apoe$^{-/-}$ mice (data not shown). Reduced AAA formation in Apoe-/-Fcer1a$^{-/-}$ mice can be partially recovered after recipient mice receiving macrophages from Apoe$^{-/-}$ mice but not those from Apoe-/-Fcer1α$^{-/-}$ mice (FIGS. 13A-13C).

Figure 14A:
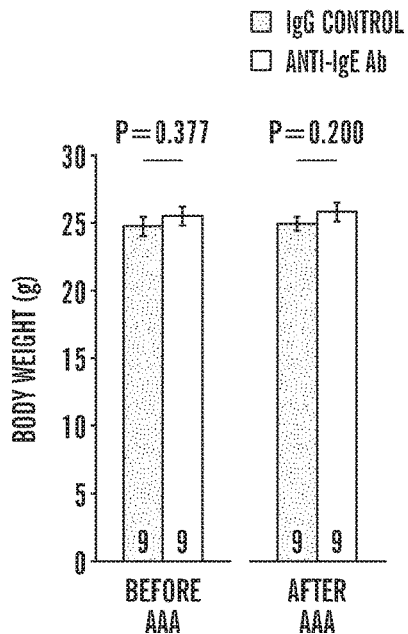
FIGS. 14A-14E demonstrate that in experimental AAA mice, anti-IgE antibody (one dose per two weeks) did not affect body weight (FIG. 14A), but significantly suppressed AAA lesion formation and associated inflammation (FIGS. 14B-14E).
Figure 14B:
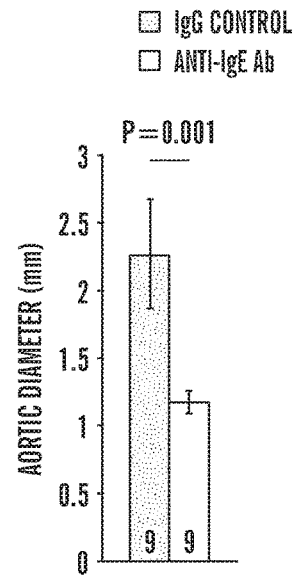
Figure 14C:
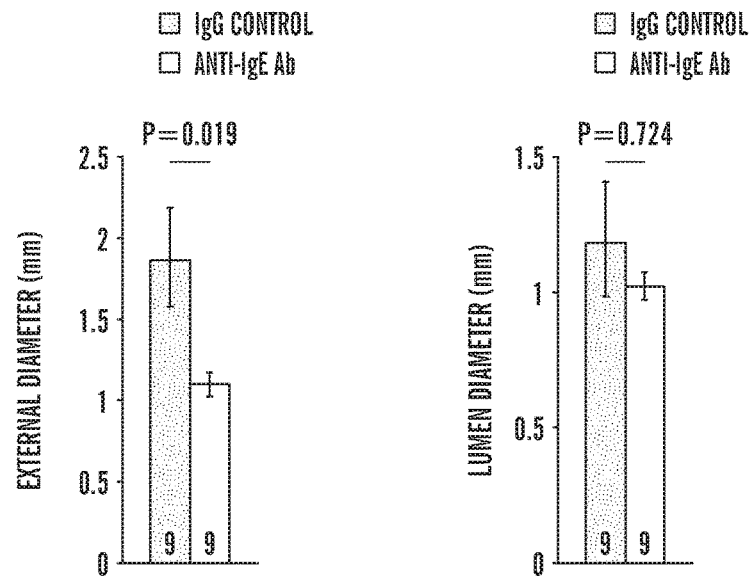
Figure 14D:
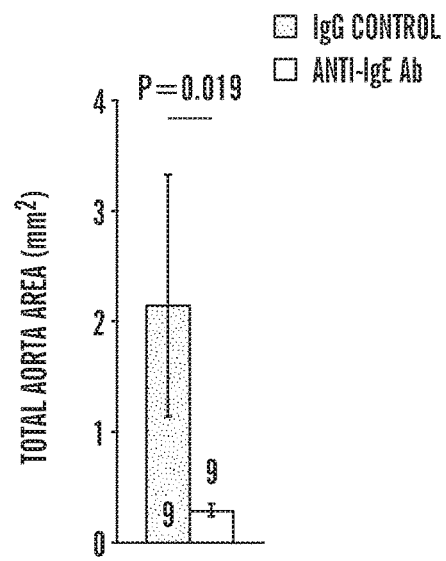
Figure 14E:
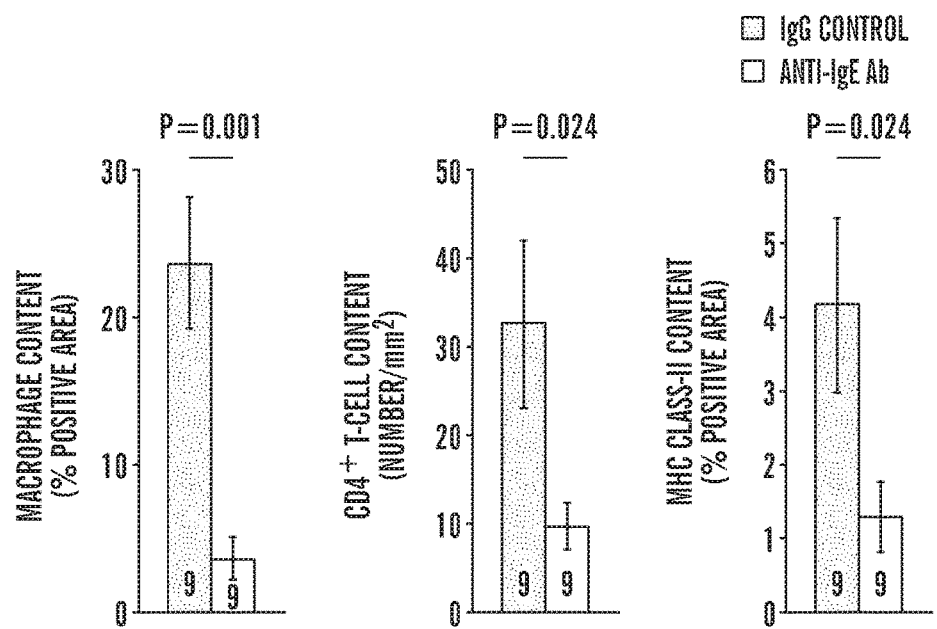

In experimental AAA mice, anti-IgE antibody (one dose per two weeks) did not affect body weight (FIG. 14A), but significantly suppressed AAA lesion formation and associated inflammation (FIGS. 14B-14E).

It is described herein that in patients with atherosclerosis, plasma IgE levels correlate with the plaque stability. Further, the inventors have demonstrated that patients with acute myocardial infarction have double the IgE levels in patients with stable angina pectoris or those without coronary heart disease. In human atherosclerotic lesions, IgE accumulates in macrophage-rich area, whereas normal human aortas do not contain IgE. In patients with abdominal aortic aneurysm, serum IgE levels correlate with later surgical repair. In patients with pre-diabetes and type-2 diabetes, plasma IgE levels significantly associated with the status of diabetes and plasma glucose levels.

Using mice deficient in IgE high affinity receptor Fc epsilon R1, it was demonstrated that these mice were protected from Western diet-induced atherosclerosis in Apoe-/- mice. Compared with control mice, these mice showed 50~75% reduction of atherosclerotic lesions throughout the aortas. Mechanistically, IgE induces cell signaling, inflammatory cytokine and chemokine expression (IL6 and MCP-1), and apoptosis.

It is further demonstrated that IgE induces formation of a novel complex between Fc epsilon receptor-1 and Toll-like receptor 4. IgE induces macrophage apoptosis by activating proton pump NHE1, thereby reducing extracellular pH. Indeed, in human atherosclerotic lesions, TUNEL-positive macrophage-rich areas are positive for IgE and have low pH.

plasma levels of chymase (P=0.030) or IgE (P=0.022) and diabetes mellitus. Ordinal logistic regression analysis showed that IgE was a significant risk factor of pre-diabetes and diabetes mellitus (odds ratio [OR]: 1.674, P=0.034). After adjustment for common diabetes risk factors, including age, sex, hypertension, body-mass index, cholesterol, homeostatic model assessment (HOMA) index, high-sensitivity C-reactive protein (hs-CRP), and mast cell chymase and tryptase, IgE remained a significant risk factor (OR: 1.866, P=0.015). Two-variable ordinal logistic analysis indicated that interactions between hs-CRP and IgE, or between IgE and chymase, increased further the risks of developing pre-diabetes and diabetes mellitus before (OR: 2.204, P=0.044; OR: 2.479, P=0.033) and after (OR: 2.251, P=0.040; OR: 2.594, P=0.026) adjustment for common diabetes risk factors (data not shown). These data demonstrate that both IgE and chymase associate with diabetes status. While IgE and hs-CRP are individual risk factors of pre-diabetes and diabetes mellitus, interactions of IgE with hs-CRP or with chymase further increased the risk of pre-diabetes and diabetes mellitus (Wang et al. PLOS One 6(12): e28962; which is incorporated by reference herein in its entirety.)

Example 4: Immunoglobulin E and Mast Cell Proteases are Potential Risk Factors of Impaired Fasting Glucose and Impaired Glucose Tolerance in Humans A total of 260 subjects 55-75 years of age were grouped as normal glucose tolerance (NGT), isolated impaired fasting glucose (I-IFG), isolated impaired glucose tolerance (I-IGT) and mixed IFG/IGT. There were significant differences in plasma levels of hsCRP (high-sensitivity C-reactive protein, P<0.001) and IgE (P=0.003) among all subgroups of pre-diabetes, and chymase in I-IGT (P=0.043) and mixed IFG/IGT (P=0.037) subgroups compared with NGT group. HsCRP was a risk factor in all subgroups of pre-diabetes; IgE was a risk factor of mixed IFG/IGT; and chymase was a risk factor of I-IGT and mixed IFG/IGT. Interactions between hsCRP and high waist circumference (WC), waist-to-hip ratio (WHR), or HOMA-β index, and interactions between IgE and high WC or tryptase levels all increased

TABLE 8

Plasma IgE levels are significantly higher in AAA patients (n = 487) than in age-matched non-AAA controls (n = 200).

| | AAA | N | Mean | Std. Deviation | Std. Error Mean | t-test P-value | Mann Whithney p-value |
|---|---|---|---|---|---|---|---|
| IgE | No | 200 | 7.0986 | 24.01648 | 1.69822 | | |
| | Yes | 487 | 81.7928 | 1367.01730 | 61.94547 | 0.44 | <0.001 |
| TransIgE | No | 200 | 1.1492 | 1.12675 | .07967 | | |
| | Yes | 487 | 1.5566 | 1.40268 | .06356 | <0.001 | <0.001 |

Example 3: Immunoglobulin E and Mast Cell Proteases are Potential Risk Factors of Human Pre-Diabetes and Diabetes Mellitus A total of 340 subjects 55 to 75 years of age were grouped according to the American Diabetes Association 2003 (ADA 2003) criteria of normal glucose tolerance, pre-diabetes, and diabetes mellitus. The Kruskal-Wallis test demonstrated significant differences in plasma IgE levels (P=0.008) among groups with different glucose tolerance status. Linear regression analysis revealed significant correlations between further the risk of developing I-IFG, I-IGT, or mixed IFG/IGT (data not shown). Plasma hsCRP, IgE, and chymase levels associate with pre-diabetes status. While hsCRP, IgE, and chymase are individual risk factors of pre-diabetes, interactions with metabolic parameters increased further the risk of pre-diabetes. Plasma levels of hsCRP, IgE, and mast cell protease chymase are significantly higher in patients with pre-diabetes than in those with normal blood glucose levels. Plasma levels of hsCRP, IgE, and chymase are significant risk factors of human pre-diabetes before and after adjustment for common diabetes risk factors. Interactions between plasma hsCRP and IgE levels with metabolic parameters increase further the risk of pre-diabetes.

What is claimed herein is:

1. A method comprising, administering a therapeutically effective amount of an IgE signaling inhibitor to a subject in need of a treatment for atherosclerosis, wherein the IgE inhibitor binds to IgE and inhibits the binding of IgE to a receptor molecule.

2. A method comprising, administering a therapeutically effective amount of an IgE signaling inhibitor to a subject in need of a treatment for abdominal aortic aneurysm, wherein the IgE inhibitor binds to IgE and inhibits the binding of IgE to a receptor molecule.

3. The method of claim 1, wherein the IgE inhibitor is selected from the group consisting of; an IgE monoclonal antibody; omalizumab; and talizumab.

4. The method of claim 2, wherein the IgE inhibitor is selected from the group consisting of; an anti-IgE monoclonal antibody; omalizumab; and talizumab.

* * * * *

SEQUENCE LISTING

<160> NUMBER OF SEQ ID NOS: 14

<210> SEQ ID NO 1
<211> LENGTH: 1488
<212> TYPE: DNA
<213> ORGANISM: Homo sapiens

<400> SEQUENCE: 1

| | | | | | |
|---|---|---|---|---|---|
| aacggcttca | gctagggagc | ggggagccca | atagagtcag | aggccaaata | gaacaggaac | 60 |
| ttggaacaag | cagaatttag | cataatgaat | cctccaagcc | aggagatcga | ggagcttccc | 120 |
| aggaggcggt | gttgcaggcg | tgggactcag | atcgtgctgc | tggggctggt | gaccgccgct | 180 |
| ctgtgggctg | gctgctgac | tctgcttctc | ctgtggcact | gggacaccac | acagagtcta | 240 |
| aaacagctgg | aagagagggc | tgcccggaac | gtctctcaag | tttccaagaa | cttggaaagc | 300 |
| caccacggtg | accagatggc | gcagaaatcc | cagtccacgc | agatttcaca | ggaactggag | 360 |
| gaacttcgag | ctgaacagca | gagattgaaa | tctcaggact | tggagctgtc | ctggaacctg | 420 |
| aacgggcttc | aagcagatct | gagcagcttc | aagtcccagg | aattgaacga | gaggaacgaa | 480 |
| gcttcagatt | tgctggaaag | actccgggag | gaggtgacaa | agctaaggat | ggagttgcag | 540 |
| gtgtccagcg | gctttgtgtg | caacacgtgc | cctgaaaagt | ggatcaattt | ccaacggaag | 600 |
| tgctactact | tcggcaaggg | caccaagcag | tgggtccacg | cccggtatgc | ctgtgacgac | 660 |
| atggaagggc | agctggtcag | catccacagc | ccggaggagc | aggacttcct | gaccaagcat | 720 |
| gccagccaca | ccggctcctg | gattggcctt | cggaacttgg | acctgaaggg | ggagtttatc | 780 |
| tgggtggatg | ggagccacgt | ggactacagc | aactgggctc | caggggagcc | caccagccgg | 840 |
| agccagggcg | aggactgcgt | gatgatgcgg | ggctccggtc | gctggaacga | cgccttctgc | 900 |
| gaccgtaagc | tgggcgcctg | ggtgtgcgac | cggctggcca | catgcacgcc | gccagccagc | 960 |
| gaaggttccg | cggagtccat | gggacctgat | tcaagaccag | accctgacgg | ccgcctgccc | 1020 |
| accccctctg | cccctctcca | ctcttgagca | tggatacagc | caggcccaga | gcaagaccct | 1080 |
| gaagaccccc | aaccacggcc | taaaagcctc | tttgtggctg | aaaggtccct | gtgacatttt | 1140 |
| ctgccaccca | aacggaggca | gctgacacat | ctcccgctcc | tctatggccc | ctgccttccc | 1200 |
| aggagtacac | cccaacagca | ccctctccag | atgggagtgc | cccaacagc | accctctcca | 1260 |
| gatgagagta | caccccaaca | gcaccctctc | cagatgagag | tacaccccaa | cagcaccctc | 1320 |
| tccagatgag | agtacacccc | aacagcaccc | tctccagatg | cagccccatc | tcctcagcac | 1380 |
| cccaggacct | gagtatcccc | agctcaggtg | gtgagtcctc | ctgtccagcc | tgcatcaata | 1440 |
| aaatggggca | gtgatggcct | cccacatttg | tccccttctt | ggaaaaaa | | 1488 |

<210> SEQ ID NO 2
<211> LENGTH: 1624
<212> TYPE: DNA
<213> ORGANISM: Homo sapiens

<400> SEQUENCE: 2

| | | | | | |
|---|---|---|---|---|---|
| agtggctcta | ctttcagaag | aaagtgtctc | tcttcctgct | taaacctctg | tctctgacgg | 60 |
| tccctgccaa | tcgctctggt | cgaccccaac | acactaggag | gacagacaca | ggctccaaac | 120 |
| tccactaagt | gaccagagct | gtgattgtgc | ccgctgagtg | gactgcgttg | tcagggagtg | 180 |
| agtgctccat | catcgggaga | atccaagcag | gaccgccatg | gaggaaggtc | aatattcaga | 240 |
| gatcgaggag | cttcccagga | ggcggtgttg | caggcgtggg | actcagatcg | tgctgctggg | 300 |
| gctggtgacc | gccgctctgt | gggctgggct | gctgactctg | cttctcctgt | ggcactggga | 360 |

```
caccacacag agtctaaaac agctggaaga gagggctgcc cggaacgtct ctcaagtttc    420
caagaacttg gaaagccacc acggtgacca gatggcgcag aaatcccagt ccacgcagat    480
ttcacaggaa ctggaggaac ttcgagctga acagcagaga ttgaaatctc aggacttgga    540
gctgtcctgg aacctgaacg ggcttcaagc agatctgagc agcttcaagt cccaggaatt    600
gaacgagagg aacgaagctt cagatttgct ggaaagactc cgggaggagg tgacaaagct    660
aaggatggag ttgcaggtgt ccagcggctt tgtgtgcaac acgtgccctg aaaagtggat    720
caatttccaa cggaagtgct actacttcgg caagggcacc aagcagtggg tccacgcccg    780
gtatgcctgt gacgacatgg aagggcagct ggtcagcatc acagcccgg aggagcagga    840 cttcctgacc aagcatgcca gccacaccgg ctcctggatt ggccttcgga acttggacct    900 gaaggggag tttatctggg tggatgggag ccacgtggac tacagcaact gggctccagg    960
ggagcccacc agccggagcc agggcgagga ctgcgtgatg atgcggggct ccggtcgctg   1020 gaacgacgc ttctgcgacc gtaagctggg cgcctgggtg tgcgaccggc tggccacatg   1080
cacgccgcca gccagcgaag gttccgcgga gtccatggga cctgattcaa gaccagaccc   1140
tgacggccgc ctgcccaccc cctctgcccc tctccactct tgagcatgga tacagccagg   1200
cccagagcaa gaccctgaag acccccaacc acggcctaaa agcctctttg tggctgaaag   1260
gtccctgtga cattttctgc cacccaaacg gaggcagctg acacatctcc cgctcctcta   1320
tggcccctgc cttcccagga gtacacccca acagcaccct ctccagatgg gagtgccccc   1380
aacagcaccc tctccagatg agagtacacc ccaacagcac cctctccaga tgagagtaca   1440
ccccaacagc accctctcca gatgagagta caccccaaca gcaccctctc cagatgcagc   1500
cccatctcct cagcaccca ggacctgagt atccccagct caggtggtga gtcctcctgt   1560
ccagcctgca tcaataaaat ggggcagtga tggcctccca catttgtccc cttcttggaa   1620
aaaa                                                                1624

<210> SEQ ID NO 3
<211> LENGTH: 1620
<212> TYPE: DNA
<213> ORGANISM: Homo sapiens

<400> SEQUENCE: 3
agtggctcta ctttcagaag aaagtgtctc tcttcctgct taaacctctg tctctgacgg     60
tccctgccaa tcgctctggt cgaccccaac acactaggag gacagacaca ggctccaaac    120
tccactaacc agagctgtga ttgtgcccgc tgagtggact gcgttgtcag ggagtgagtg    180
ctccatcatc gggagaatcc aagcaggacc gccatggagg aaggtcaata ttcagagatc    240
gaggagcttc ccaggaggcg tgttgcagg cgtgggactc agatcgtgct gctgggctg    300 gtgaccgccg ctctgtgggc tgggctgctg actctgcttc tcctgtggca ctgggacacc    360
acacagagtc taaaacagct ggaagagagg gctgccgga cgtctctca gtttccaag    420 aacttggaaa gccaccacgg tgaccagatg gcgcagaaat cccagtccac gcagatttca    480
caggaactgg aggaacttcg agctgaacag cagagattga atctcagga cttggagctg    540 tcctggaacc tgaacgggct tcaagcagat ctgagcagct tcaagtccca ggaattgaac    600
gagaggaacg aagcttcaga tttgctggaa agactccggg aggaggtgac aaagctaagg    660
atggagttgc aggtgtccag cggctttgtg tgcaacacgt gccctgaaaa gtggatcaat    720
ttccaacgga agtgctacta cttcggcaag ggcaccaagc agtgggtcca cgcccggtat    780
```

```
gcctgtgacg acatggaagg gcagctggtc agcatccaca gcccggagga gcaggacttc    840
ctgaccaagc atgccagcca caccggctcc tggattggcc ttcggaactt ggacctgaag    900
ggggagttta tctgggtgga tgggagccac gtggactaca gcaactgggc tccaggggag    960
cccaccagcc ggagccaggg cgaggactgc gtgatgatgc ggggctccgg tcgctggaac   1020
gacgccttct gcgaccgtaa gctgggcgcc tgggtgtgcg accggctggc cacatgcacg   1080
ccgccagcca gcgaaggttc gcggagtcc atgggacctg attcaagacc agaccctgac    1140
ggccgcctgc ccacccccctc tgcccctctc cactcttgag catggataca gccaggccca   1200
gagcaagacc ctgaagaccc ccaaccacgg cctaaaagcc tctttgtggc tgaaaggtcc   1260
ctgtgacatt ttctgccacc caaacggagg cagctgacac atctcccgct cctctatggc   1320
ccctgccttc ccaggagtac accccaacag caccctctcc agatgggagt gccccccaaca  1380 gcaccctctc cagatgagag tacaccccaa cagcaccctc tccagatgag agtacacccc   1440
aacagcaccc tctccagatg agtacacacc caacagcac cctctccaga tgcagcccca    1500
tctcctcagc accccaggac ctgagtatcc ccagctcagg tggtgagtcc tcctgtccag   1560
cctgcatcaa taaatgggg cagtgatggc ctcccacatt tgtcccctc ttggaaaaaa    1620
```

<210> SEQ ID NO 4
<211> LENGTH: 320
<212> TYPE: PRT
<213> ORGANISM: Homo sapiens

<400> SEQUENCE: 4

```
Met Asn Pro Pro Ser Gln Glu Ile Glu Glu Leu Pro Arg Arg Arg Cys
1               5                   10                  15

Cys Arg Arg Gly Thr Gln Ile Val Leu Leu Gly Leu Val Thr Ala Ala
            20                  25                  30

Leu Trp Ala Gly Leu Leu Thr Leu Leu Leu Leu Trp His Trp Asp Thr
        35                  40                  45

Thr Gln Ser Leu Lys Gln Leu Glu Glu Arg Ala Ala Arg Asn Val Ser
    50                  55                  60

Gln Val Ser Lys Asn Leu Glu Ser His His Gly Asp Gln Met Ala Gln
65                  70                  75                  80

Lys Ser Gln Ser Thr Gln Ile Ser Gln Glu Leu Glu Glu Leu Arg Ala
                85                  90                  95

Glu Gln Gln Arg Leu Lys Ser Gln Asp Leu Glu Leu Ser Trp Asn Leu
            100                 105                 110

Asn Gly Leu Gln Ala Asp Leu Ser Ser Phe Lys Ser Gln Glu Leu Asn
        115                 120                 125

Glu Arg Asn Glu Ala Ser Asp Leu Leu Glu Arg Leu Arg Glu Glu Val
    130                 135                 140

Thr Lys Leu Arg Met Glu Leu Gln Val Ser Ser Gly Phe Val Cys Asn
145                 150                 155                 160

Thr Cys Pro Glu Lys Trp Ile Asn Phe Gln Arg Lys Cys Tyr Tyr Phe
                165                 170                 175

Gly Lys Gly Thr Lys Gln Trp Val His Ala Arg Tyr Ala Cys Asp Asp
            180                 185                 190

Met Glu Gly Gln Leu Val Ser Ile His Ser Pro Glu Glu Gln Asp Phe
        195                 200                 205

Leu Thr Lys His Ala Ser His Thr Gly Ser Trp Ile Gly Leu Arg Asn
    210                 215                 220

Leu Asp Leu Lys Gly Glu Phe Ile Trp Val Asp Gly Ser His Val Asp
```

```
                  225                 230                 235                 240
        Tyr Ser Asn Trp Ala Pro Gly Glu Pro Thr Ser Arg Ser Gln Gly Glu
                        245                 250                 255

Asp Cys Val Met Met Arg Gly Ser Gly Arg Trp Asn Asp Ala Phe Cys
                        260                 265                 270

Asp Arg Lys Leu Gly Ala Trp Val Cys Asp Arg Leu Ala Thr Cys Thr
                        275                 280                 285

Pro Pro Ala Ser Glu Gly Ser Ala Glu Ser Met Gly Pro Asp Ser Arg
                        290                 295                 300

Pro Asp Pro Asp Gly Arg Leu Pro Thr Pro Ser Ala Pro Leu His Ser
        305                 310                 315                 320

<210> SEQ ID NO 5
<211> LENGTH: 321
<212> TYPE: PRT
<213> ORGANISM: Homo sapiens

<400> SEQUENCE: 5

Met Glu Glu Gly Gln Tyr Ser Glu Ile Glu Glu Leu Pro Arg Arg Arg
1               5                   10                  15

Cys Cys Arg Arg Gly Thr Gln Ile Val Leu Gly Leu Val Thr Ala
                20                  25                  30

Ala Leu Trp Ala Gly Leu Leu Thr Leu Leu Leu Trp His Trp Asp
            35                  40                  45

Thr Thr Gln Ser Leu Lys Gln Leu Glu Glu Arg Ala Ala Arg Asn Val
    50                  55                  60

Ser Gln Val Ser Lys Asn Leu Glu Ser His His Gly Asp Gln Met Ala
65                  70                  75                  80

Gln Lys Ser Gln Ser Thr Gln Ile Ser Gln Glu Leu Glu Glu Leu Arg
                85                  90                  95

Ala Glu Gln Gln Arg Leu Lys Ser Gln Asp Leu Glu Leu Ser Trp Asn
            100                 105                 110

Leu Asn Gly Leu Gln Ala Asp Leu Ser Ser Phe Lys Ser Gln Glu Leu
        115                 120                 125

Asn Glu Arg Asn Glu Ala Ser Asp Leu Leu Glu Arg Leu Arg Glu Glu
    130                 135                 140

Val Thr Lys Leu Arg Met Glu Leu Gln Val Ser Ser Gly Phe Val Cys
145                 150                 155                 160

Asn Thr Cys Pro Glu Lys Trp Ile Asn Phe Gln Arg Lys Cys Tyr Tyr
                165                 170                 175

Phe Gly Lys Gly Thr Lys Gln Trp Val His Ala Arg Tyr Ala Cys Asp
            180                 185                 190

Asp Met Glu Gly Gln Leu Val Ser Ile His Ser Pro Glu Glu Gln Asp
        195                 200                 205

Phe Leu Thr Lys His Ala Ser His Thr Gly Ser Trp Ile Gly Leu Arg
    210                 215                 220

Asn Leu Asp Leu Lys Gly Glu Phe Ile Trp Val Asp Gly Ser His Val
225                 230                 235                 240

Asp Tyr Ser Asn Trp Ala Pro Gly Glu Pro Thr Ser Arg Ser Gln Gly
                245                 250                 255

Glu Asp Cys Val Met Met Arg Gly Ser Gly Arg Trp Asn Asp Ala Phe
            260                 265                 270

Cys Asp Arg Lys Leu Gly Ala Trp Val Cys Asp Arg Leu Ala Thr Cys
        275                 280                 285
```

```
Thr Pro Pro Ala Ser Glu Gly Ser Ala Glu Ser Met Gly Pro Asp Ser
    290                 295                 300

Arg Pro Asp Pro Asp Gly Arg Leu Pro Thr Pro Ser Ala Pro Leu His
305                 310                 315                 320

Ser

<210> SEQ ID NO 6
<211> LENGTH: 321
<212> TYPE: PRT
<213> ORGANISM: Homo sapiens

<400> SEQUENCE: 6

Met Glu Glu Gly Gln Tyr Ser Glu Ile Glu Glu Leu Pro Arg Arg Arg
1               5                   10                  15

Cys Cys Arg Arg Gly Thr Gln Ile Val Leu Leu Gly Leu Val Thr Ala
                20                  25                  30

Ala Leu Trp Ala Gly Leu Leu Thr Leu Leu Leu Trp His Trp Asp
            35                  40                  45

Thr Thr Gln Ser Leu Lys Gln Leu Glu Glu Arg Ala Ala Arg Asn Val
    50                  55                  60

Ser Gln Val Ser Lys Asn Leu Glu Ser His His Gly Asp Gln Met Ala
65                  70                  75                  80

Gln Lys Ser Gln Ser Thr Gln Ile Ser Gln Glu Leu Glu Glu Leu Arg
                85                  90                  95

Ala Glu Gln Gln Arg Leu Lys Ser Gln Asp Leu Glu Leu Ser Trp Asn
                100                 105                 110

Leu Asn Gly Leu Gln Ala Asp Leu Ser Ser Phe Lys Ser Gln Glu Leu
            115                 120                 125

Asn Glu Arg Asn Glu Ala Ser Asp Leu Leu Glu Arg Leu Arg Glu Glu
    130                 135                 140

Val Thr Lys Leu Arg Met Glu Leu Gln Val Ser Ser Gly Phe Val Cys
145                 150                 155                 160

Asn Thr Cys Pro Glu Lys Trp Ile Asn Phe Gln Arg Lys Cys Tyr Tyr
                165                 170                 175

Phe Gly Lys Gly Thr Lys Gln Trp Val His Ala Arg Tyr Ala Cys Asp
            180                 185                 190

Asp Met Glu Gly Gln Leu Val Ser Ile His Ser Pro Glu Glu Gln Asp
    195                 200                 205

Phe Leu Thr Lys His Ala Ser His Thr Gly Ser Trp Ile Gly Leu Arg
210                 215                 220

Asn Leu Asp Leu Lys Gly Glu Phe Ile Trp Val Asp Gly Ser His Val
225                 230                 235                 240

Asp Tyr Ser Asn Trp Ala Pro Gly Glu Pro Thr Ser Arg Ser Gln Gly
                245                 250                 255

Glu Asp Cys Val Met Met Arg Gly Ser Gly Arg Trp Asn Asp Ala Phe
            260                 265                 270

Cys Asp Arg Lys Leu Gly Ala Trp Val Cys Asp Arg Leu Ala Thr Cys
    275                 280                 285

Thr Pro Pro Ala Ser Glu Gly Ser Ala Glu Ser Met Gly Pro Asp Ser
    290                 295                 300

Arg Pro Asp Pro Asp Gly Arg Leu Pro Thr Pro Ser Ala Pro Leu His
305                 310                 315                 320

Ser
```

-continued

<210> SEQ ID NO 7
<211> LENGTH: 1198
<212> TYPE: DNA
<213> ORGANISM: Homo sapiens

<400> SEQUENCE: 7

```
tactaagagt ctccagcatc ctccacctgt ctaccaccga gcatgggcct atatttgaag      60
ccttagatct ctccagcaca gtaagcacca ggagtccatg aagaagatgg ctcctgccat     120
ggaatcccct actctactgt gtgtagcctt actgttcttc gctccagatg gcgtgttagc     180
agtccctcag aaacctaagg tctccttgaa ccctccatgg aatagaatat ttaaaggaga     240
gaatgtgact cttacatgta atgggaacaa tttctttgaa gtcagttcca ccaaatggtt     300
ccacaatggc agcctttcag aagagacaaa ttcaagtttg aatattgtga atgccaaatt     360
tgaagacagt ggagaataca atgtcagca ccaacaagtt aatgagagtg aacctgtgta     420
cctggaagtc ttcagtgact ggctgctcct tcaggcctct gctgaggtgg tgatggaggg     480
ccagcccctc ttcctcaggt gccatggttg gaggaactgg gatgtgtaca aggtgatcta     540
ttataaggat ggtgaagctc tcaagtactg gtatgagaac cacaacatct ccattacaaa     600
tgccacagtt gaagacagtg gaacctacta ctgtacgggc aaagtgtggc agctggacta     660
tgagtctgag ccccctcaaca ttactgtaat aaaagctccg cgtgagaagt actggctaca     720
attttttatc ccattgttgg tggtgattct gtttgctgtg gacacaggat tatttatctc     780
aactcagcag caggtcacat ttctcttgaa gattaagaga accaggaaag gcttcagact     840
tctgaaccca catcctaagc caaaccccaa aaacaactga tataattact caagaaatat     900
ttgcaacatt agttttttc cagcatcagc aattgctact caattgtcaa acacagcttg     960
caatatacat agaaacgtct gtgctcaagg atttatagaa atgcttcatt aaactgagtg    1020
aaactggtta agtggcatgt aatagtaagt gctcaattaa cattggttga ataaatgaga    1080
gaatgaatag attcatttat tagcatttgt aaaagagatg ttcaatttca ataaataaa    1140
tataaaacca tgtaacagaa tgcttctgag taaaaaaaaa aaaaaaaaa aaaaaaaa      1198
```

<210> SEQ ID NO 8
<211> LENGTH: 257
<212> TYPE: PRT
<213> ORGANISM: Homo sapiens

<400> SEQUENCE: 8

```
Met Ala Pro Ala Met Glu Ser Pro Thr Leu Leu Cys Val Ala Leu Leu
1               5                   10                  15

Phe Phe Ala Pro Asp Gly Val Leu Ala Val Pro Gln Lys Pro Lys Val
            20                  25                  30

Ser Leu Asn Pro Pro Trp Asn Arg Ile Phe Lys Gly Glu Asn Val Thr
        35                  40                  45

Leu Thr Cys Asn Gly Asn Asn Phe Phe Glu Val Ser Ser Thr Lys Trp
    50                  55                  60

Phe His Asn Gly Ser Leu Ser Glu Glu Thr Asn Ser Ser Leu Asn Ile
65                  70                  75                  80

Val Asn Ala Lys Phe Glu Asp Ser Gly Glu Tyr Lys Cys Gln His Gln
                85                  90                  95

Gln Val Asn Glu Ser Glu Pro Val Tyr Leu Glu Val Phe Ser Asp Trp
            100                 105                 110

Leu Leu Leu Gln Ala Ser Ala Glu Val Val Met Glu Gly Gln Pro Leu
        115                 120                 125
```

```
Phe Leu Arg Cys His Gly Trp Arg Asn Trp Asp Val Tyr Lys Val Ile
130                 135                 140
Tyr Tyr Lys Asp Gly Glu Ala Leu Lys Tyr Trp Tyr Glu Asn His Asn
145                 150                 155                 160
Ile Ser Ile Thr Asn Ala Thr Val Glu Asp Ser Gly Thr Tyr Tyr Cys
                165                 170                 175
Thr Gly Lys Val Trp Gln Leu Asp Tyr Glu Ser Glu Pro Leu Asn Ile
            180                 185                 190
Thr Val Ile Lys Ala Pro Arg Glu Lys Tyr Trp Leu Gln Phe Phe Ile
            195                 200                 205
Pro Leu Leu Val Val Ile Leu Phe Ala Val Asp Thr Gly Leu Phe Ile
210                 215                 220
Ser Thr Gln Gln Gln Val Thr Phe Leu Leu Lys Ile Lys Arg Thr Arg
225                 230                 235                 240
Lys Gly Phe Arg Leu Leu Asn Pro His Pro Lys Pro Asn Pro Lys Asn
                245                 250                 255
Asn
```

<210> SEQ ID NO 9
<211> LENGTH: 3658
<212> TYPE: DNA
<213> ORGANISM: Homo sapiens

<400> SEQUENCE: 9

```
aacccatttc aactgcctat tcagagcatg cagtaagagg aaatccacca agtctcaata      60
taataatatt ctttattcct ggacagctcg gttaatgaaa aatggacac  agaaagtaat    120
aggagagcaa atcttgctct cccacaggag ccttccagtg tgcctgcatt tgaagtcttg    180
gaaatatctc cccaggaagt atcttcaggc agactattga agtcggcctc atccccacca    240
ctgcatacat ggctgacagt tttgaaaaaa gagcaggagt tcctgggggt aacacaaatt    300
ctgactgcta tgtatgcct  ttgttttgga acagttgtct gctctgtact tgatatttca    360
cacattgagg gagacatttt ttcatcattt aaagcaggtt atccattctg gggagccata    420
ttttttttcta tttctggaat gttgtcaatt atatctgaaa ggagaaatgc aacatatctg    480
gtgagaggaa gcctgggagc aaacactgcc agcagcatag ctgggggaac gggaattacc    540
atcctgatca tcaacctgaa gaagagcttg gcctatatcc acatccacag ttgccagaaa    600
tttttttgaga ccaagtgctt tatggcttcc ttttccactg aaattgtagt gatgatgctg    660
tttctcacca ttctgggact tggtagtgct gtgtcactca caatctgtgg agctggggaa    720
gaactcaaag gaaacaaggt tccagaggat cgtgtttatg aagaattaaa catatattca    780
gctacttaca gtgagttgga agacccaggg gaaatgtctc ctcccattga tttataagaa    840
tcacgtgtcc agaacactct gattcacagc caaggatcca aaggccaag  gtcttgttaa    900
ggggctactg gaaaaattc  tattctctcc acagcctgct ggtttacat  tagatttatt    960
cgcctgataa gaatattttg tttctgctgc ttctgtccac cttaatattc tccttctatt   1020
tgtagatatg atagactcct attttttcttg ttttatatta tgaccacaca catctctgct   1080
ggaaagtcaa catgtagtaa gcaagattta actgtttgat tataactgtg caaatacaga   1140
aaaaagaag  gctggctgaa agttgagtta aactttgaca gtttgataat atttggttct   1200
tagggttttt ttttttttt  agcattctta atagttacag ttgggcatga tttgtaccat   1260
ccacccatac ccacacagtc acagtcacac acacatatgt attacttaca ctatatataa   1320
cttcctatgc aaatatttta ccaccagtca ataatacatt tttgccaaga catgaagttt   1380
```

-continued

```
tataaagatc tgtataattg cctgaatcac cagcacattc actgacatga tattatttgc    1440
agattgacaa gtaggaagtg gggaatttta ttaagttact cgttgtctgg ggaggtaaat    1500
aggttaaaaa cagggaaatt ataagtgcag agattaacat tcacaaatg tttagtgaaa     1560 catttgtgaa aaaagaagac taaattaaga cctgagctga aataaagtga gtggaaatgg    1620
aaataatggt tatatctaaa acatgtagaa aaagagtaac tggtagattt tgttaacaaa    1680
ttaaagaata aagttagaca agcaactggt tgactaatac attaagcgtt tgagtctaag    1740
atgaaaggag aacactggtt atgttgatag aatgataaaa agggtcgggc gcggaggctc    1800
acgcctgtaa tcccagccct tgggaggcc gaggtgggca gatcacgaag tcagtagttt     1860
gagaccagcc tggccaacat agtgaaaccc cgtctctact aaaaatacaa aaaaaaatt     1920 agctgggtgt ggtggcagtc acctgtagtc ccagctactt gggaggctga ggcaggagaa    1980
tcgcttcaac ctgggaggcg gaggttgcag tgagccgaga tcgcaccagt gcactccagc    2040
cttggtgaca atgggagact ccatctcaaa aaaaaaaaaa aaaaaaaaaa agataaaaag    2100
tcagaaatct gaaaagtgga ggaagagtac aaatagacct aaattaagct cattttagg     2160 ctttgatttt ggggagacaa agggaaatgc agccatagag ggcctgatga catccaatac    2220
agagttctgg taaagataaa atttgataca ggtttggtgt cattataaga gaaatcatta    2280
ttaaatgaag caagttaaca ctctaagaga attattttga gatagaagtg aagctaagct    2340
aaacttcaca tgcctataat tggagggaaa aactaaggat aaaatctagc ctagaagata    2400
caataattag tcataaacat gcattgtgaa actgtagaga gcaggtagcc caaaatagag    2460
aaagattaga taaagagaaa ataagtatcc atcagagaca gtatctctag gcttgggcaa    2520
gagaaaagtc cacagtgata agcaactcca cctaaggcat gaatatgcgg cagagaaaac    2580
agcaatagtg aatgaatgca aaaggtgctg agaaattcca cacatgagta ttgtgatgag    2640
taaatgaata aaacatttgc aaagacctt agagaaagag aatgggagca tatgtgagaa     2700
ataagatagt tgattatgaa tagaaggtag tgaagaaaag caagctaaga aaaaattctg    2760
tttataaaag aaggaaaaga tagtttatgt ttttagccta agtataagag tcctacagat    2820
ggactgaaaa aaatcagtct gagagtatta gtcacaatta atgaaataat tacatttat     2880 gtattgagga tgccaagatt aaaaggtgac aggtagatgt taatttccct agattgtgaa    2940
agtgatcacg acaatcacac aacaaataat taagtgactt ggtatgcttt atttaattgt    3000
agggcctgag gttttccatt ctcatttttc taaaatacaa ttttgtttct ccaaatttga    3060
cagcagaata aaaccctac cctttcactg tgtatcatgc taagctgcat ctctactctt     3120
gatcatctgt aggtattaat cacatcactt ccatggcatg gatgttcaca tacagactct    3180
taaccctggt ttaccaggac ctctaggagt ggatccaatc tatatcttta cagttgtata    3240
gtatatgata tctctttat ttcactcaat ttatattttc atcattgact acatatttct     3300
tatacacaac acacaattta tgaatttttt ctcaagatca ttctgagagt tgccccaccc    3360
tacctgcctt ttatagtatg cccacctcag gcagacacag agcacaatgc tggggttctc    3420
ttcacactat cactgcccca aattgtcttt ctaaatttca acttcaatgt catcttctcc    3480
atgaagacca ctgaatgaac accttttcat ccagccttaa tttcttgctc cataactact    3540
ctatcccacg atgcagtatt gtatcattaa ttattagtgt gcttgtgacc tccttatgta    3600
ttctcaatta cctgtatttg tgcaataaat tggaataatg taacttgaaa aaaaaaa      3658
```

<210> SEQ ID NO 10

<211> LENGTH: 3529
<212> TYPE: DNA
<213> ORGANISM: Homo sapiens

<400> SEQUENCE: 10

| | | | | | |
|---|---|---|---|---|---|
| aacccatttc | aactgcctat | tcagagcatg | cagtaagagg | aaatccacca | agtctcaata | 60 |
| taataatatt | ctttattcct | ggacagctcg | gttaatgaaa | aatggacac | agaaagtaat | 120 |
| aggagagcaa | atcttgctct | cccacaggag | ccttccagtg | tgcctgcatt | tgaagtcttg | 180 |
| gaaatatctc | cccaggaagt | atcttcaggc | agactattga | agtcggcctc | atccccacca | 240 |
| ctgcatacat | ggctgacagt | tttgaaaaaa | gagcaggagt | tcctgggtt | ttctatttct | 300 |
| ggaatgttgt | caattatatc | tgaaaggaga | aatgcaacat | atctggtgag | aggaagcctg | 360 |
| ggagcaaaca | ctgccagcag | catagctggg | ggaacgggaa | ttaccatcct | gatcatcaac | 420 |
| ctgaagaaga | gcttggccta | tatccacatc | cacagttgcc | agaaattttt | tgagaccaag | 480 |
| tgctttatgg | cttccttttc | cactgaaatt | gtagtgatga | tgctgtttct | caccattctg | 540 |
| ggacttggta | gtgctgtgtc | actcacaatc | tgtggagctg | gggaagaact | caaaggaaac | 600 |
| aaggttccag | aggatcgtgt | ttatgaagaa | ttaaacatat | attcagctac | ttacagtgag | 660 |
| ttggaagacc | caggggaaat | gtctcctccc | attgattat | aagaatcacg | tgtccagaac | 720 |
| actctgattc | acagccaagg | atccagaagg | ccaaggtctt | gttaaggggc | tactggaaaa | 780 |
| atttctattc | tctccacagc | ctgctggttt | tacattagat | ttattcgcct | gataagaata | 840 |
| ttttgtttct | gctgcttctg | tccaccttaa | tattctcctt | ctatttgtag | atatgataga | 900 |
| ctcctatttt | tcttgtttta | tattatgacc | acacacatct | ctgctgggaaa | gtcaacatgt | 960 |
| agtaagcaag | atttaactgt | ttgattataa | ctgtgcaaat | acagaaaaaa | agaaggctgg | 1020 |
| ctgaaagttg | agttaaactt | tgacagtttg | ataatatttg | gttcttaggg | ttttttttt | 1080 |
| tttttagcat | tcttaatagt | tacagttggg | catgatttgt | accatccacc | catacccaca | 1140 |
| cagtcacagt | cacacacaca | tatgtattac | ttacactata | tataacttcc | tatgcaaata | 1200 |
| ttttaccacc | agtcaataat | acattttgc | caagacatga | agttttataa | agatctgtat | 1260 |
| aattgcctga | atcaccagca | cattcactga | catgatatta | tttgcagatt | gacaagtagg | 1320 |
| aagtggggaa | ttttattaag | ttactcgttg | tctggggagg | taaataggtt | aaaaacaggg | 1380 |
| aaattataag | tgcagagatt | aacatttcac | aaatgtttag | tgaaacattt | gtgaaaaaag | 1440 |
| aagactaaat | taagacctga | gctgaaataa | agtgagtgga | aatggaaata | atggttatat | 1500 |
| ctaaaacatg | tagaaaaaga | gtaactggta | gattttgtta | acaaattaaa | gaataaagtt | 1560 |
| agacaagcaa | ctggttgact | aatacattaa | gcgtttgagt | ctaagatgaa | aggagaacac | 1620 |
| tggttatgtt | gatagaatga | taaaaagggt | cgggcgcgga | ggctcacgcc | tgtaatccca | 1680 |
| gcccttgggg | aggccgaggt | gggcagatca | cgaagtcagt | agtttgagac | cagcctggcc | 1740 |
| aacatagtga | aaccccgtct | ctactaaaaa | tacaaaaaaa | aaattagctg | ggtgtggtgg | 1800 |
| cagtcacctg | tagtcccagc | tacttgggag | gctgaggcag | gagaatcgct | tcaacctggg | 1860 |
| aggcggaggt | tgcagtgagc | cgagatcgca | ccagtgcact | ccagccttgg | tgacaatggg | 1920 |
| agactccatc | tcaaaaaaa | aaaaaaaaa | aaaaagata | aaaagtcaga | aatctgaaaa | 1980 |
| gtggaggaag | agtacaaata | gacctaaatt | aagctcattt | ttaggctttg | attttgggga | 2040 |
| gacaaaggga | aatgcagcca | tagagggcct | gatgacatcc | aatacagagt | tctggtaaag | 2100 |
| ataaaatttg | atacaggttt | ggtgtcatta | taagagaaat | cattattaaa | tgaagcaagt | 2160 |
| taacactcta | agagaattat | tttgagatag | aagtgaagct | aagctaaact | tcacatgcct | 2220 |

```
ataattggag ggaaaaacta aggataaaat ctagcctaga agatacaata attagtcata    2280
aacatgcatt gtgaaactgt agagagcagg tagcccaaaa tagagaaaga ttagataaag    2340
agaaaataag tatccatcag agacagtatc tctaggcttg ggcaagagaa aagtccacag    2400
tgataagcaa ctccacctaa ggcatgaata tgcggcagag aaaacagcaa tagtgaatga    2460
atgcaaaagg tgctgagaaa ttccacacat gagtattgtg atgagtaaat gaataaaaca    2520
tttgcaaaga cctttagaga aagagaatgg gagcatatgt gagaaataag atagttgatt    2580
atgaatagaa ggtagtgaag aaaagcaagc taagaaaaaa ttctgtttat aaaagaagga    2640
aaagatagtt tatgttttta gcctaagtat aagagtccta cagatggact gaaaaaaatc    2700
agtctgagag tattagtcac aattaatgaa ataattacat tttatgtatt gaggatgcca    2760
agattaaaag gtgacaggta gatgttaatt tccctagatt gtgaaagtga tcacgacaat    2820
cacacaacaa ataattaagt gacttggtat gctttattta attgtagggc ctgaggtttt    2880
ccattctcat ttttctaaaa tacaattttg tttctccaaa tttgacagca gaataaaaac    2940
cctacccttt cactgtgtat catgctaagc tgcatctcta ctcttgatca tctgtaggta    3000
ttaatcacat cacttccatg gcatggatgt tcacatacag actcttaacc ctggtttacc    3060
aggacctcta ggagtggatc caatctatat ctttacagtt gtatagtata tgatatctct    3120
tttatttcac tcaatttata ttttcatcat tgactacata tttcttatac acaacacaca    3180
atttatgaat tttttctcaa gatcattctg agagttgccc caccctacct gccttttata    3240
gtatgcccac ctcaggcaga cacagagcac aatgctgggg ttctcttcac actatcactg    3300
ccccaaattg tctttctaaa tttcaacttc aatgtcatct tctccatgaa gaccactgaa    3360
tgaacacctt ttcatccagc cttaatttct tgctccataa ctactctatc ccacgatgca    3420
gtattgtatc attaattatt agtgtgcttg tgacctcctt atgtattctc aattacctgt    3480
atttgtgcaa taaattggaa taatgtaact tgaaaaaaaa aaaaaaaa               3529
```

<210> SEQ ID NO 11
<211> LENGTH: 244
<212> TYPE: PRT
<213> ORGANISM: Homo sapiens

<400> SEQUENCE: 11

```
Met Asp Thr Glu Ser Asn Arg Arg Ala Asn Leu Ala Leu Pro Gln Glu
1               5                   10                  15

Pro Ser Ser Val Pro Ala Phe Glu Val Leu Glu Ile Ser Pro Gln Glu
                20                  25                  30

Val Ser Ser Gly Arg Leu Leu Lys Ser Ala Ser Ser Pro Pro Leu His
            35                  40                  45

Thr Trp Leu Thr Val Leu Lys Lys Glu Gln Glu Phe Leu Gly Val Thr
        50                  55                  60

Gln Ile Leu Thr Ala Met Ile Cys Leu Cys Phe Gly Thr Val Val Cys
65                  70                  75                  80

Ser Val Leu Asp Ile Ser His Ile Glu Gly Asp Ile Phe Ser Ser Phe
                85                  90                  95

Lys Ala Gly Tyr Pro Phe Trp Gly Ala Ile Phe Phe Ser Ile Ser Gly
                100                 105                 110

Met Leu Ser Ile Ile Ser Glu Arg Arg Asn Ala Thr Tyr Leu Val Arg
            115                 120                 125

Gly Ser Leu Gly Ala Asn Thr Ala Ser Ser Ile Ala Gly Gly Thr Gly
        130                 135                 140
```

Ile Thr Ile Leu Ile Ile Asn Leu Lys Lys Ser Leu Ala Tyr Ile His
145                 150                 155                 160

Ile His Ser Cys Gln Lys Phe Phe Glu Thr Lys Cys Phe Met Ala Ser
            165                 170                 175

Phe Ser Thr Glu Ile Val Val Met Met Leu Phe Leu Thr Ile Leu Gly
        180                 185                 190

Leu Gly Ser Ala Val Ser Leu Thr Ile Cys Gly Ala Gly Glu Glu Leu
    195                 200                 205

Lys Gly Asn Lys Val Pro Glu Asp Arg Val Tyr Glu Glu Leu Asn Ile
210                 215                 220

Tyr Ser Ala Thr Tyr Ser Glu Leu Glu Asp Pro Gly Glu Met Ser Pro
225                 230                 235                 240

Pro Ile Asp Leu

<210> SEQ ID NO 12
<211> LENGTH: 199
<212> TYPE: PRT
<213> ORGANISM: Homo sapiens

<400> SEQUENCE: 12

Met Asp Thr Glu Ser Asn Arg Arg Ala Asn Leu Ala Leu Pro Gln Glu
1               5                   10                  15

Pro Ser Ser Val Pro Ala Phe Glu Val Leu Glu Ile Ser Pro Gln Glu
            20                  25                  30

Val Ser Ser Gly Arg Leu Leu Lys Ser Ala Ser Ser Pro Pro Leu His
        35                  40                  45

Thr Trp Leu Thr Val Leu Lys Lys Glu Gln Glu Phe Leu Gly Phe Ser
    50                  55                  60

Ile Ser Gly Met Leu Ser Ile Ile Ser Glu Arg Arg Asn Ala Thr Tyr
65                  70                  75                  80

Leu Val Arg Gly Ser Leu Gly Ala Asn Thr Ala Ser Ser Ile Ala Gly
            85                  90                  95

Gly Thr Gly Ile Thr Ile Leu Ile Ile Asn Leu Lys Lys Ser Leu Ala
        100                 105                 110

Tyr Ile His Ile His Ser Cys Gln Lys Phe Phe Glu Thr Lys Cys Phe
    115                 120                 125

Met Ala Ser Phe Ser Thr Glu Ile Val Val Met Met Leu Phe Leu Thr
130                 135                 140

Ile Leu Gly Leu Gly Ser Ala Val Ser Leu Thr Ile Cys Gly Ala Gly
145                 150                 155                 160

Glu Glu Leu Lys Gly Asn Lys Val Pro Glu Asp Arg Val Tyr Glu Glu
            165                 170                 175

Leu Asn Ile Tyr Ser Ala Thr Tyr Ser Glu Leu Glu Asp Pro Gly Glu
        180                 185                 190

Met Ser Pro Pro Ile Asp Leu
    195

<210> SEQ ID NO 13
<211> LENGTH: 591
<212> TYPE: DNA
<213> ORGANISM: Homo sapiens

<400> SEQUENCE: 13
cagaacggcc gatctccagc ccaagatgat tccagcagtg gtcttgctct tactcctttt      60
ggttgaacaa gcagcggccc tgggagagcc tcagctctgc tatatcctgg atgccatcct     120

```
gtttctgtat ggaattgtcc tcaccctcct ctactgtcga ctgaagatcc aagtgcgaaa    180
ggcagctata accagctatg agaaatcaga tggtgtttac acgggcctga gcaccaggaa    240
ccaggagact tacgagactc tgaagcatga gaaaccacca cagtagcttt agaatagatg    300
cggtcatatt cttctttggc ttctggttct tccagccctc atggttggca tcacatatgc    360
ctgcatgcca ttaacaccag ctggccctac ccctataatg atcctgtgtc ctaaattaat    420
atacaccagt ggttcctcct ccctgttaaa gactaatgct cagatgctgt ttacggatat    480
ttatattcta gtctcactct cttgtcccac ccttcttctc ttccccattc ccaactccag    540
ctaaaatatg ggaagggaga accccccaata aaactgccat ggactggact c            591
```

<210> SEQ ID NO 14
<211> LENGTH: 86
<212> TYPE: PRT
<213> ORGANISM: Homo sapiens

<400> SEQUENCE: 14

```
Met Ile Pro Ala Val Val Leu Leu Leu Leu Val Glu Gln Ala
1               5                   10                  15

Ala Ala Leu Gly Glu Pro Gln Leu Cys Tyr Ile Leu Asp Ala Ile Leu
                20                  25                  30

Phe Leu Tyr Gly Ile Val Leu Thr Leu Leu Tyr Cys Arg Leu Lys Ile
            35                  40                  45

Gln Val Arg Lys Ala Ala Ile Thr Ser Tyr Glu Lys Ser Asp Gly Val
        50                  55                  60

Tyr Thr Gly Leu Ser Thr Arg Asn Gln Glu Thr Tyr Glu Thr Leu Lys
65                  70                  75                  80

His Glu Lys Pro Pro Gln
                85
```